(12) United States Patent
Lu et al.

(10) Patent No.: US 11,873,535 B2
(45) Date of Patent: Jan. 16, 2024

(54) AUTHENTICATION OF BOTANICAL DNA ISOLATED FROM DIETARY SUPPLEMENTS

(71) Applicant: Herbalife International of America, Inc., Los Angeles, CA (US)

(72) Inventors: Zhengfei Lu, Alhambra, CA (US); Silva Babajanian, Porter Ranch, CA (US); Yanjun Zhang, Reseda, CA (US); Peter Chang, Newbury Park, CA (US); Gary Swanson, Mission Viejo, CA (US); Maria Rubinsky, Redondo Beach, CA (US)

(73) Assignee: HERBALIFE INTERNATIONAL OF AMERICA, INC., Los Angeles, CA (US)

( * ) Notice: Subject to any disclaimer, the term of this patent is extended or adjusted under 35 U.S.C. 154(b) by 182 days.

(21) Appl. No.: 16/048,091

(22) Filed: Jul. 27, 2018

(65) Prior Publication Data

US 2019/0032153 A1 Jan. 31, 2019

Related U.S. Application Data

(60) Provisional application No. 62/562,101, filed on Sep. 22, 2017, provisional application No. 62/538,423, filed on Jul. 28, 2017.

(51) Int. Cl.
*C12Q 1/6895* (2018.01)
*C12Q 1/6855* (2018.01)

(52) U.S. Cl.
CPC ......... *C12Q 1/6895* (2013.01); *C12Q 1/6855* (2013.01)

(58) Field of Classification Search
CPC ............................ C12Q 1/6895; C12Q 1/6855
See application file for complete search history.

(56) References Cited

U.S. PATENT DOCUMENTS

2003/0050470 A1* 3/2003 An ..................... C07H 21/00
435/6.14

FOREIGN PATENT DOCUMENTS

WO    WO 02/36805 A2    5/2002

OTHER PUBLICATIONS

O'Malley, An adapter ligation-mediated PCR method for high-throughput mapping of T-DNA inserts in the *Arabidopsis* genome, Nature Protocols, 2, 2910-2917, 2007. (Year: 2007).*
Ruzicka, Identification of Verbena officinalis Based on ITS Sequence Analysis and RAPD-Derived Molecular Markers, Planta Med, 75(11): 1271-1276, 2009. (Year: 2009).*
Parkinson, Preparation of high-quality next-generation sequencing libraries from picogram quantities of target DNA, Genome Res., 22(1): 125-133, 2012. (Year: 2012).*
Lowe, A computer program for selection of oligonucleotide primers for polymerase chain reactions, Nucleic Acids Research, 18(7): 1757-1761, 1990.I (Year: 1990).*
Lo, Identification of constituent herbs in ginseng decoctions by DNA marker, Chin. Med., 10(1): 1-8, 2015. (Year: 2015).*
Coregenomics, Troubleshooting DNA ligation in NGS library prep, 2015. (Year: 2015).*
Little, DNA Barcode Authentication of Saw Palmetto Herbal Dietary Supplements, Sci Rep, 3, 3518, 2013. (Year: 2013).*
Liu, LM-PCR Permits Highly Representative Whole Genome Amplification of DNA Isolated From Small Number of Cells and Paraffin-Embedded Tumor Tissue Sections, Diagn Mol Pathol, 13(2): 105-115, 2004. (Year: 2004).*
Pirker, Whole Genome Amplification for CGH Analysis: Linker—Adapter PCR as the Method of Choice for Difficult and Limited Samples, Cytometry Part A, 61A:26-34, 2004. (Year: 2004).*
Parveen, DNA Barcoding for the Identification of Botanicals in Herbal Medicine and Dietary Supplements: Strengths and Limitations, Planta Med, 82: 1225-1235, 2016. (Year: 2016).*
Avula, et al. (2014). J Pharm Biomed Anal, 88, 278-288.
Bauer et al. (2004). Environmental biosafety research, 3(4), 215-223.
Calixto, J. (2000). Brazilian Journal of Medical and Biological Research, 33(2), 179-189.
CBOL Plant Working Group. PNAS 106(31), (2009), p. 12794-12797.
Chen, et al. (2010). Validation of the ITS2 region as a novel DNA barcode for identifying medicinal plant species. PLOS One, 5(1), e8613.
Cheng et al., "Biological ingredient analysis of traditional Chinese medicine preparation based on high-throughput sequencing: the story for Liuwei Dihuang Wan", Scientific Reports, vol. 4, No. 1, Jun. 3, 2014 (Jun. 3, 2014), XP055541613.
Chiou et al: "Authentication of Medicinal Herbs using PCR-amplified ITS21 with Specific Primer s", Planta Medica, Oct. 1, 2007 (Oct. 1, 2007), pp. 1421-1426, Retrieved from the Internet: URL: https://www.thieme-connect.de/products/ejournals/pdf/10.1055/s-2007-990227.pdf.
Chung et al: "The minimal amount of starting DNA for Agilent's hybrid capture-based targeted massively parallel sequencing", Scientific Reports, vol. 6, No. 1, May 25, 2016 (May 25, 2016).
Cimino, M. T. (2010). Planta Med, 76(5), 495-497.
Gryson et al. (2002). Journal of the American Oil Chemists' Society, 79(2), 171.
Gryson, N. (2010). Anal Bioanal Chem, 396(6), 2003-2022.
Guan et al. (2013). Applied Biochemistry and Biotechnology, 169(2), 368-379.
Hellebrand et al. (1998). Zeitschrift für Lebensmitteluntersuchung und-Forschung A, 206(4), 237.
Henriques, et al. (2012). BMC Res Notes, 5, 637.
Heubl, G. (2010). Planta Med. 76(17), 1963-1974.
Ivanova et al.: "Authentication of Herbal Supplements Using Next-Generation Sequencing", PLOS ONE, vol. 11, No. 5, May 26, 2016 (May 25, 2016), p. e0156426.

(Continued)

Primary Examiner — Samuel C Woolwine
Assistant Examiner — Carolyn L Greene
(74) Attorney, Agent, or Firm — Knobbe, Martens, Olson & Bear LLP

(57) ABSTRACT

Described herein are methods and kits for authentication of botanical DNA fragments isolated from processed botanical products, including dietary supplements or nutraceutical compositions including botanical extracts.

18 Claims, 34 Drawing Sheets

Specification includes a Sequence Listing.

(56) References Cited

OTHER PUBLICATIONS

Kirsten et al: "The potential of three different PCR-related approaches for the authentication of mixtures of herbal substances and finished herbal medicinal products", Phytomedicine, Elsevier, Amsterdam, NL, vol. 43, Mar. 21, 2018 (Mar. 21, 2018), pp. 60-67.
Little, D. P. (2014). Genome, 57(9), 513-516.
Mishra et al., "DNA barcoding: an efficient tool to overcome authentication challenges in the herbal market", Plant Biotechnology Journal, vol. 14, No. 1, Jan. 1, 2016 (Jan. 1, 2016), pp. 8-21, XP055541607.
Morales, et al. (2009). Appl Environ Microbiol, 75(9), 2677-2683.
Newmaster et al. BMC medicine 11.1 (2013), p. 222.
Novak et al., "DNA-based authentication of plant extracts", Food Research Internati, Elsevier, Amsterdam, Nl, vol. 40, No. 3, Jan. 23, 2007 (Jan. 23, 2007), pp. 388-392, XP005856108.
Parveen et al. (2016). Planta Medica, 82(14), 1225-1235.
Sagi, et al. (2014). J Sep Sci, 37(19), 2797-2804.
Sarma, N. (2015). DNA Testing of Herbal Supplements-Does it Work or Doesn't It ?.
Seguin-Orlando: "Ligation Bias in Illumina Next-Generation DNA Libraries: Implications for Sequencing Ancient Genomes", Plos One, vol. 8, No. 10, Oct. 29, 2013 (Oct. 29, 2013), p. e78575.
Sgamma et al., "DNA barcoding for Industrial Quality Assurance", Planta Medica, vol. 83, No. 14/15, Jun. 29, 2017 (Jun. 29, 2017), pp. 1117-1129, XP055523874.
Xanthopoulou et al., "Multiplex HRM analysis as a tool for rapid molecular authentication of nine herbal teas", Food Control., vol. 60, Jul. 17, 2015 (Jul. 17, 2015), pp. 113-116, XP055540690.
Zheng et al., "A Comprehensive Quality Evaluation System for Complex Herbal Medicine Using PacBio Sequencing, PCR-Denaturing Gradient Gel Electrophoresis , and Several Chemical Approaches", Frontiers in Plant Science, vol. 8, Sep. 13, 2017 (Sep. 13, 2017), XP055523876.
Partial Search Report issued in application No. PCT/US2018/044211, dated Nov. 29, 2018.
Search Report issued in application No. PCT/US2018/044211, dated Feb. 5, 2019.
O'Malley et al., An adapter ligation-mediated PCR method for high-throughput mapping of T-DNA inserts in the Arabidopsis genome, Nature Protocol 2:11, 2910-2917 (2007).
First Office Action in Chinese Patent Application No. 201880061546.4 dated Feb. 10, 2023, which is related to the present application.

* cited by examiner

1. *Matricaria recutita* specific primer
2. *Tanacetum parthenium* specific primer
3. *Chamaemelum nobile* specific primer
4. *Chrysanthemum spp.* specific primer

AUTHENTICATION OF BOTANICAL DNA ISOLATED FROM DIETARY SUPPLEMENTS

CROSS-REFERENCE TO RELATED APPLICATIONS

This application claims the benefit of priority to U.S. Provisional Application Nos. 62/538,423, filed Jul. 28, 2017, and 62/562,101, filed Sep. 22, 2017, the disclosures of which are hereby expressly incorporated by reference in their entireties.

FIELD

The present disclosure relates to authentication of processed botanical materials, such as powders and extracts in dietary supplements. In particular, the present disclosure relates to methods and kits for assessing botanical DNA fragments in dietary supplements.

BACKGROUND

DNA-based methods have gained recognition as a tool for botanical authentication in herbal medicine; however, the low quality of DNA both in terms of DNA size and also DNA quantity in botanical extracts limit the effectiveness of these methods.

Industrial processing of botanicals for use in herbal medicines or in dietary supplements leads to the damage of the DNA. The size of DNA in dried botanical tissue decreases from around 600 base pairs (bp) or greater to less than 200 bp. This makes botanical DNA undetectable in processed botanicals (e.g., in botanical extracts or sterilized powders) with current DNA detection methods, such as traditional DNA barcoding.

Botanical dietary supplements are prepared using plants or plant parts for their medicinal or therapeutic properties and flavor or scent. With consumers' increasing awareness of the link between a healthy diet and its potential health benefits, the botanical dietary supplements market is growing rapidly. According to a report published by Persistence Market Research, the global botanical supplement market is projected to reach a valuation of US $37,950 million by the end of 2017. In terms of revenue, the market is set to witness a Compound Annual Growth Rate (CAGR) of 6.9% during the forecast period (Research, P. M. *Global Market Study on Botanical Supplements: Drugs Application Segment to Hold Maximum Value Share During 2017-2025*; 2017, incorporated by reference herein in its entirety).

With the growth of global botanical dietary supplement consumption also comes the increased incidence of substitution or adulteration of herbal products with lower-cost species. Botanical substitution or adulteration may lead to less healthy benefits or even unexpected health risks. To maximize health benefits and customer safety, it is necessary to correctly identify the target botanical and detect adulterants. Multiple methods for botanical identification have been proposed in many pharmacopoeias and are currently being used in the quality control process of dietary supplements manufacture. These methods include morphological (macroscopic and microscopic) and chemical methods. However, these methods are challenged by the loss of physical features in the processed product and variation of botanical chemical profile due to seasonal and geographical differences. In addition, both types of methods have a limited ability to detect adulterants in practice, especially in the setting of global trading.

SUMMARY

It is therefore an aspect of this disclosure to provide methods and kits for analyzing DNA fragments in processed botanical samples, such as in herbal medicine, dietary supplements, botanical extracts, or processed botanical powders. Specifically, provided herein are methods and kits that use adapter-ligation and amplification of the adapter-ligated DNA to confirm the existence of amplifiable botanical DNA and develop assays for authentication of the target botanical DNA.

Some embodiments provided herein relate to a method of authenticating processed botanical material. In one embodiment, the method includes isolating genomic DNA from a sample, ligating adapters to the botanical DNA fragments to generate adapter-ligated DNA fragments, amplifying the adapter-ligated DNA fragments to detect the botanical DNA fragments and to determine a size range of the botanical DNA fragments, hybridizing PCR-based primers to a target nucleic acid sequence in the botanical DNA fragments, and amplifying the target nucleic acid sequence. In some embodiments, the genomic DNA isolated from the sample includes botanical DNA fragments. In some embodiments, detecting the botanical DNA fragments includes running the amplified adapter-ligated DNA fragments on a gel for separation of the botanical DNA fragments so that the fragments may be visualized.

In one embodiment, the method includes isolating genomic DNA from a sample, ligating adapters to the botanical DNA fragments to generate adapter-ligated DNA fragments, amplifying the adapter-ligated DNA fragments to detect the botanical DNA fragments and to determine a size range of the botanical DNA fragments, designing PCR-based primers according to the size range of the botanical DNA fragments, hybridizing the PCR-based primers to a target nucleic acid sequence in the botanical DNA fragments, and amplifying the target nucleic acid sequence. In some embodiments, the PCR-based primers are designed on the basis of target species consensus sequence as PCR template and non-target consensus sequences as exclusion sequences. In some embodiments, designing includes selecting from a library. In some embodiments, the genomic DNA isolated from the sample includes botanical DNA fragments. In some embodiments, detecting the botanical DNA fragments includes running the amplified adapter-ligated DNA fragments on a gel for separation of the botanical DNA fragments so that the fragments may be visualized.

In some embodiments, the method further includes sequencing the target nucleic acid sequence to authenticate a botanical species present in the sample. In some embodiments, the method further includes detecting botanical adulteration in the sample. In some embodiments, the sample is a processed botanical sample. In some embodiments, the processed botanical sample is a dietary supplement, a botanical extract, or a powder. In some embodiments, the processed botanical sample is sterilized. In some embodiments, the botanical DNA fragments are less than 220 base pairs. In some embodiments, the botanical DNA fragments are present in an amount of 1 pg to 1 ng. In some embodiments, amplifying is performed by polymerase chain reaction (PCR). In some embodiments, the botanical is chamomile (including *Matricaria chamomilla* (also referred to as German chamomile or *Matricaria recutita*), feverfew (*Tanacetum parthenium*), Roman chamomile (*Chamaemelum nobile* syn *anthemis nobilis*), Chinese chamomile (*Chrysanthemum* x *morifolium*, or *Chrysanthemum indicum*), guarana (*Paullinia cupana*), parsley (*Petroselinum crispum*), celery (*Apium graveolens*), fennel (*Foeniculum vulgare*), Asian ginseng (*Panax ginseng*), American ginseng (*Panax quinquefolius*), Tienchi ginseng (*Panax notoginseng*), Siberian ginseng (*Eleutherococcus senticosus*) Dong Quai (*Angelica sinensis*), garden angelica (*Angelica archangelica*), pubescent Angelica (*Angelica pubescens*)), dahurian angelica (*Angelica dahurica*), Chinese cinnamon (*Cinnamomum cassia*), true cinnamon (*Cinnamomum verum* syn *Cinnamomum zeylanicum*), Indonesian cinnamon (*Cinnamomum burmannii*), Ginkgo (*Ginkgo biloba*), Japanese sophora (*Sophora japonica*), buckwheat (*Fagopyrum esculentum*), jujube (*Ziziphus spinosa*), Indian jujube (*Ziziphus mauritiana*), Japanese raisin tree (*Hovenia dulcis*), ginger (*Zingiber officinale*), lesser galangal (*Alpinia officinarum*), greater galangal (*Alpinia galanga*), schisandra (*Schisandra chinensis*), southern schisandra (*Schisandra sphenanthera*), astragalus (*Astragalus membranaceus*), maca (*Lepidium meyenii*), radish (*Raphanus sativus*), turnip (*Brassica rapa*), peppermint (*Mentha piperita*), Chinese mint (*Mentha canadensis*), green tea (*Camellia sinensis*), rosemary (*Rosmarinus officinalis*), bilberry (*Vaccinium myrtillus*), blueberry (*Vaccinium corymbosum*), cranberry (*Vaccinium macrocarpon*), mulberry (*Morus alba*), or guarana (*Paullinia cupana*).

In some embodiments, the PCR-based primers are a species-specific primer set. In some embodiments, the species-specific primer set includes a first primer including a nucleic acid sequence as defined in SEQ ID NO: 1 and a second primer including a nucleic acid sequence as defined in SEQ ID NO: 2. In some embodiments, the species-specific primer set includes a primer including a nucleic acid sequence as defined in SEQ ID NO: 3 and a primer including a nucleic acid sequence as defined in SEQ ID NO: 4. In some embodiments, the species-specific primer set includes a primer including a nucleic acid sequence as defined in SEQ ID NO: 5 and a primer including a nucleic acid sequence as defined in SEQ ID NO: 6. In some embodiments, the species-specific primer set includes a primer including a nucleic acid sequence as defined in SEQ ID NO: 7 and a primer including a nucleic acid sequence as defined in SEQ ID NO: 8.

Some embodiments provided herein relate to a method for authenticating chamomile in supplement. In some embodiments, the method includes obtaining a dietary supplement including a plant extract. In some embodiments, the method further includes isolating genomic DNA from the dietary supplement. In some embodiments, the genomic DNA includes chamomile DNA fragments. In some embodiments, the method further includes hybridizing a species-specific primer to a target nucleic acid sequence in or suspected of being in the dietary supplement. In some embodiments, the method further includes amplifying the chamomile DNA. In some embodiments, the method further includes authenticating the chamomile DNA by determining the presence and quantity of target nucleic acid sequence.

In some embodiments, the dietary supplement includes a sterilized botanical powder. In some embodiments, the chamomile DNA fragments are present in the supplement in an amount of about 1 pg to about 1 ng. In some embodiments, the chamomile DNA fragments are less than about 220 base pairs. In some embodiments, the chamomile DNA includes DNA from *Matricaria chamomilla, Tanacetum parthenium* (feverfew), *Chamaemelum nobile* (*Anthemis nobilis* or Roman chamomile), *Chrysanthemum* x *morifolium*, or *Chrysanthemum indicum* (Chinese chamomile). In some embodiments, the species-specific primer set includes a primer including a nucleic acid sequence as defined in SEQ ID NO: 1 and a primer including a nucleic acid sequence as defined in SEQ ID NO: 2. In some embodiments, the species-specific primer set includes a primer including a nucleic acid sequence as defined in SEQ ID NO: 3 and a primer including a nucleic acid sequence as defined in SEQ ID NO: 4. In some embodiments, the species-specific primer set includes a primer including a nucleic acid sequence as defined in SEQ ID NO: 5 and a primer including a nucleic acid sequence as defined in SEQ ID NO: 6. In some embodiments, the species-specific primer set includes a primer including a nucleic acid sequence as defined in SEQ ID NO: 7 and a primer including a nucleic acid sequence as defined in SEQ ID NO: 8.

Some embodiments provided herein relate to a method of detecting botanical DNA fragments from a dietary supplement. In some embodiments, the method includes obtaining a dietary supplement including processed botanical extracts. In some embodiments, the method further includes isolating botanical DNA fragments from the supplement. In some embodiments, the method further includes ligating adapters with a known DNA sequence to the botanical DNA fragments to generate adapter-ligated DNA. In some embodiments, the method further includes amplifying the adapter-ligated DNA; and evaluating total DNA after amplification. In some embodiments, evaluating total DNA after amplification includes determining the size of DNA fragments, determining the sequence of the DNA, determining the quantity or quality of DNA, or otherwise analyzing DNA. In some embodiments, the dietary supplement includes a processed botanical extract or powder. In some embodiments, ligating is performed at 4° C. overnight. In some embodiments, amplifying is performed by PCR.

Some embodiments provided herein relate to a kit for botanical authentication of a sample. In some embodiments, the kit including isolation reagent for isolating fragmented botanical DNA from a processed botanical sample, ligation-adapters for ligating adaptors to the fragmented botanical DNA to generate adapter-ligated DNA, a species-specific primer set for hybridizing to a target nucleic acid sequence, and amplification reagents for amplification of a target nucleic acid sequence. In some embodiments, the kit is capable of amplifying fragmented botanical DNA having less than about 220 base pairs, and present in the processed botanical sample in an amount of about 1 pg to about 1 ng. In some embodiments, the kit further includes a user's guide including instructions for executing a method of authenticating a botanical sample.

Some embodiments provided herein related to a method of authenticating botanical material. In some embodiments, the method includes isolating genomic DNA from a sample, amplifying and sequencing the genomic DNA, comparing sequencing reads to obtain a plurality of contigs, aligning the plurality of contigs based on a coding region, aligning the plurality of contigs based on a non-coding region, and authenticating a botanical material when a sequence aligns with at least 97% similarity. In some embodiments, the genomic DNA isolated from the sample includes botanical DNA fragments. In some embodiments, the method further includes detecting the botanical DNA fragments by running the amplified DNA on a gel.

In some embodiments, the sample is a root, leaf, fruit, flower, bark, and/or seed. In some embodiments, the botanical material is ginseng (including Asian ginseng (*Panax ginseng*), American ginseng (*Panax quinquefolius*), Tienchi ginseng (*Panax notoginseng*), Dong Quai (*Angelica sinensis*), Garden Angelica (*Angelica archangelica*), or Pubescent Angelica (*Angelica pubescens*)), peppermint (*Mentha piperita*), Chinese mint (*Mentha canadensis*), green tea (*Camel-*

*lia sinensis*), rosemary (*Rosmarinus officinalis*), Schisandra (*Schisandra chinensis*), Southern Schisandra (*Schisandra sphenanthera*), bilberry (*Vaccinium myrtillus*), blueberry (*Vaccinium corymbosum*), cranberry (*Vaccinium macrocarpon*), chamomile (including German chamomile (*Matricaria recutita*), Roman chamomile (*Chamaemelum nobile*), feverfew (*Tanacetum parthenium*), or Chinese chamomile (*Chrysanthemum indicum*)), Chinese cinnamon (*Cinnamomum cassia*), cinnamon (*Cinnamomum zeylanicum*), mulberry (*Morus alba*), jujube (*Ziziphus spinosa*), Indian jujube (*Ziziphus mauritiana*), or guarana (*Paullinia cupana*). In some embodiments, the coding region includes rbcL and matK coding regions. In some embodiments, the non-coding region includes ITS2, trnL-trnF, and psbA-trnH non-coding regions.

BRIEF DESCRIPTION OF THE DRAWINGS

FIG. 6A shows chamomile flower extracts processed using different solvent ratios. FIG. 6B illustrates unfiltered (UF) and filtered (F) tea extracts.

FIGS. 8A-8D depict sequence alignment diagrams of internal transcribed spacer 2 (ITS2) region and primer location of botanical species in the test scope. Arrows indicate the species-specific primer binding sites. Dots represent the nucleic acids that are identical to the nucleic acid of the nucleotide sequence listed in the top species. FIG. 8A shows the location of *Matricaria recutita* (German chamomile) primer set. FIG. 8B shows the location of *Tanacetum parthenium* (feverfew) primer set. FIG. 8C shows the location of *Chamaemelum nobile* (Roman chamomile) primer set. FIG. 8D shows the location of *Chrysanthemum indicum* (Chinese chamomile) primer set.

FIG. 20A outlines processing steps for obtaining a botanical DNA barcode, including: 1. DNA extraction; 2. PCR amplification; 3. Gel electrophoresis; 4. Sequencing; 5. Assembly of contigs; and 6. BLAST validated database. FIG. 20B outlines a schematic for identification of a botanical species.

FIG. 22A shows DNA concentration of all samples, shown in a bimodal distribution. FIG. 22B shows DNA concentration of DNA extracted from various plant parts.

FIG. 23A shows validation sample top hit similarity compared to barcode tiers. FIG. 23B shows total number of mismatches and number of gaps compared to barcode tiers. FIG. 23C shows the total number of mismatches and number of gaps compared to DNA concentration. FIG. 23D shows the nucleotide number difference between top and second best hit compared to barcode tiers.

DETAILED DESCRIPTION

Figure 1:
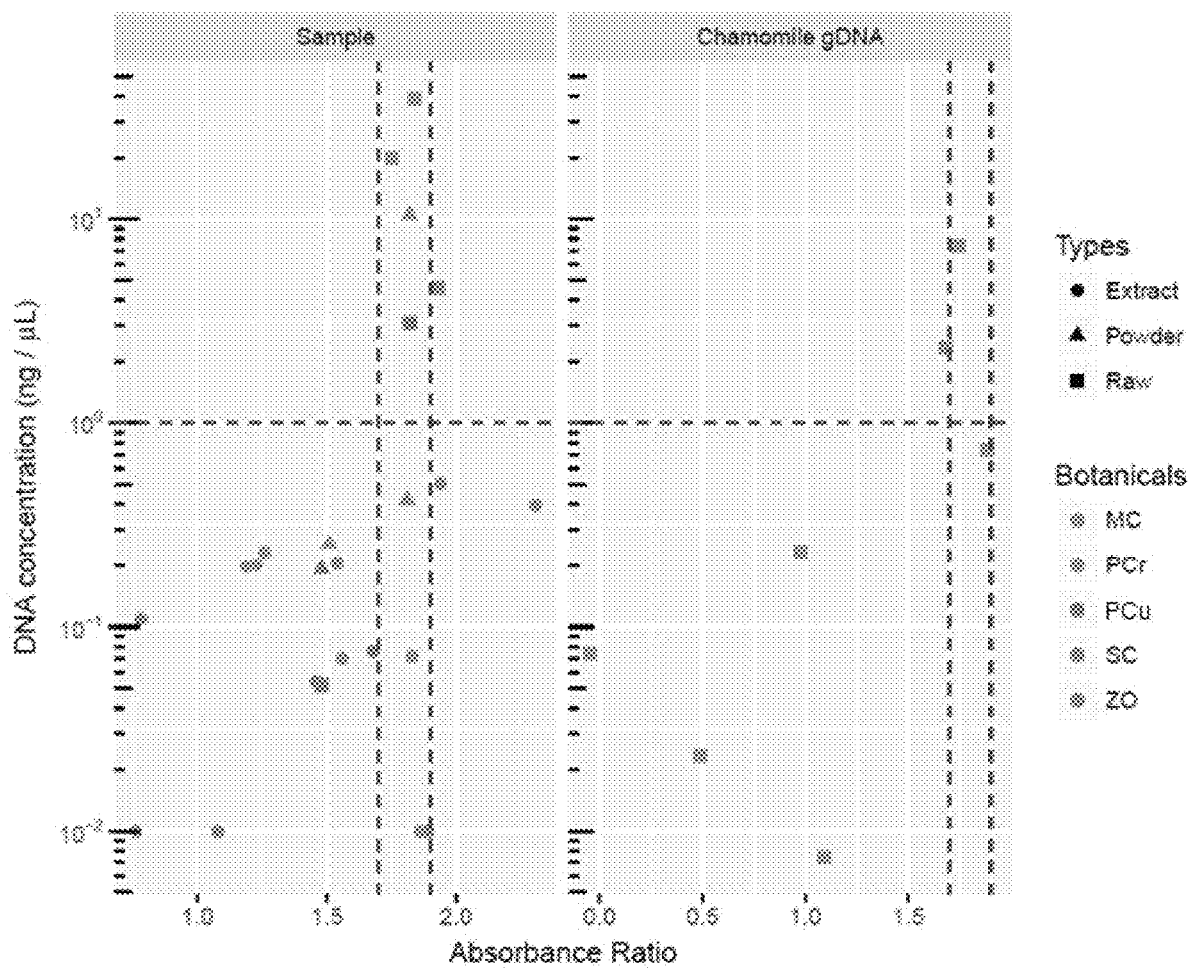
FIG. 1 provides a comparison of DNA isolated from botanical materials by DNA concentrations and absorbance ratios. Left panel: sample; right panel: chamomile gDNA. The DNA concentration (ng/µL) is displayed in logarithmic scale. Samples from different botanicals are represented as MC (*Matricaria chamomilla*), PCr (*Petroselinum crispum*), PCu (*Paullinia cupana*), SC (*Schisandra chinensis*), and ZO (*Zingiber officinale*). Dashed horizontal line marks the DNA concentration at 1 ng/µL. Two dashed vertical lines demarcate the range of pure DNA by absorbance ratio (1.7-1.9).

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Recently, DNA-based molecular analysis techniques, such as randomly amplified polymorphic DNA (RAPD), PCR-restriction fragment length polymorphism (PCR-RFLP) analyses, hybridization, microarrays, and DNA barcoding have been introduced to botanical authentication to complement the traditional physical and chemical identification methods (Heubl, G. (2010). *Planta Med*, 76(17), 1963-1974, incorporated by reference herein in its entirety).

Like the black and white barcode lines found on the packages of almost all commercial products, each botanical species has specific DNA sequences called DNA barcodes, which can be used for botanical identification.

Traditional botanical identification methods include morphological and chemical methods. However, these methods are challenged by the loss of physical features in the processed product and variation in botanical chemical profiles due to seasonal and geographical differences. DNA barcodes provide a relative stable profile for identification purposes. A single barcode for botanical identification is yet to be found. Using multiple DNA barcodes together will increase their discrimination power. However, 3 or more barcodes do not provide additional discrimination power than 2 barcodes if the appropriate combination is chosen (C. P. W. Group. *PNAS* 106(31), (2009), pp. 12794-12797; incorporated herein by reference in its entirety). Two-tiered DNA barcoding has been applied to botanical identification in research, but industry regulations require a validated method and a defined scope (Newmaster et al. *BMC medicine* 11.1 (2013), p. 222; Pawar et al. *Planta Medica* 82.05 (2016), OA17; each of which is incorporated herein by reference in its entirety).

The application of DNA-based methods in processed botanical materials, however, is challenging. For example, DNA barcoding methodologies have been tested in botanical dietary supplements; however, these studies show that DNA barcoding was not able to identify target botanical DNA in many of the tested finished products, especially botanical extracts. The quantity and quality of DNA is the key to any sensitive, reliable, and reproducible DNA-based molecular analysis; however, there are two major challenges for isolating genomic DNA from botanical materials with sufficient quantity and quality. First, secondary metabolites, such as polyphenols, terpenoids and alkaloids, are often present in the final DNA elution and act as inhibitors for PCR amplification. These compounds are usually found in higher quantities in extracts because they are enriched or included in the supplement to provide a therapeutic benefit (Demeke et al. (1992). *Biotechniques*, 12(3), 332-334, incorporated herein by reference in its entirety). Second, DNA degradation. DNA in botanical dietary supplements is either heavily degraded or completely eliminated due to the isolation process, which can include heat treatment, irradiation, filtration, or UV exposure (Cimino, M. T. (2010). *Planta Med*, 76(5), 495-497, incorporated by reference herein in its entirety). Due to these challenges, as well as limited quantities of DNA in the processed botanicals and detection limits of agarose gel, degraded genomic DNA is undetectable with current methods. In addition, the study of DNA degradation in botanical materials is further complicated by the involvement of botanically derived excipients that may also contain their own DNA. Because of these detection obstacles, the presence of amplifiable target DNA in extracts remains challenging.

To ensure product safety and therapeutic efficacy, botanical dietary supplements, especially those containing botanical extracts, undergo extensive manufacturing processes. These processes include grinding, solvent extraction, heat treatment, drying, and filtration, which aim to enrich bioactive chemical ingredients, but often remove plant tissues that contain DNA (Gryson, N. (2010). *Anal Bioanal Chem*, 396(6), 2003-2022; Parveen et al. (2016). *Planta Medica*, 82(14), 1225-1235, each of which is incorporated by reference herein in its entirety). The DNA in these supplements is low in quantity and quality, if present at all. In addition to low quantity and quality of DNA, third party evaluation of DNA in botanical dietary supplements is further complicated by the addition of botanical derived excipients later in the manufacturing process (Calixto, J. (2000). *Brazilian Journal of Medical and Biological Research*, 33(2), 179-189, incorporated by reference herein in its entirety). Because these excipients go through lighter manufacturing processes and therefore frequently contain DNA of better quality and quantity than the DNA from the botanical on the label claim, many DNA-based botanical authentication methods identify the excipients rather than the target botanicals (Ivanova et al. (2016). *PLoS One*, 11(5), e0156426; Little, D. P. (2014). *Genome*, 57(9), 513-516; Newmaster, et al. (2013). *BMC Med*, 11, 222; Pawar et al. *Planta Med*(EFirst), each of which is incorporated by reference herein in its entirety).

It is believed that DNA in processed food is fragmented into lengths of around 100 to 200 base pairs (Parveen, et al. (2016). *Planta Medica* 82, 1225-1235, incorporated by reference herein in its entirety). The presence of the degraded DNA has only been detected in DNA isolated from processed botanical tissues and crude plant oils that are made under low-oxidation environments (Bauer et al. (2004). *Environmental biosafety research*, 3(4), 215-223; Busconi et al. (2003). *Food chemistry*, 83(1), 127-134; Gryson et al. (2002). *Journal of the American Oil Chemists' Society*, 79(2), 171-174; Hellebrand et al. (1998). *Zeitschrift für Lebensmitteluntersuchung und-Forschung A*, 206(4), 237-242; Kakihara et al. (2007). *Food Control*, 18(10), 1289-1294; Murray et al. (2009). *Journal of the Science of Food and Agriculture*, 89(7), 1137-1144; Pauli et al. (2000). *Mitteilungen aus Lebensmitteluntersuchung und Hygiene*, 91(5), 491-501, each of which is incorporated by reference herein in its entirety); however DNA from botanical extracts has not yet been detected and reported. Recently, PCR and real-time PCR methods have been proposed to assess and quantify DNA fragmentation in processed foods (Guan et al. (2013). *Applied Biochemistry and Biotechnology*, 169(2), 368-379, incorporated by reference herein in its entirety). However, these indirect methods only evaluated DNA at discontinuous fragment length and the resolution of these methods is limited to the expected size range of the DNA in real botanical products.

High temperature, low pH, fermentation, mechanical force, enzymatic degradation, and irradiation are common manufacturing factors that have been studied extensively in regards to DNA degradation in food products (Gryson, N. (2010). *Anal Bioanal Chem*, 396(6), 2003-2022, incorporated by reference herein in its entirety). For the isolation of DNA from botanical extracts, the use of solvents and the filtration process are two additional factors for consideration. It is possible that DNA may not be isolated in sufficient amounts with certain solvents or may be eliminated by further refinement processes, such as filtration (Sarma, N. (2015). DNA Testing of Herbal Supplements—Does it Work or Doesn't It?, incorporated by reference herein in its entirety).

Botanicals could be mistakenly identified and purchased due to similarity in morphology or shared words in their common names. For example, several cultivated botanicals exist that appear similar or include the word "chamomile" in their common names. Special attention has to be paid to avoid confusion with the following botanical species, including *Tanacetum parthenium*, commonly known as feverfew; *Chamaemelum nobile* (synonym: *Anthemis nobilis*), commonly known as Roman chamomile; *Chrysanthemum* x *morifolium*, and *Chrysanthemum indicum*, commonly known as Chinese chamomile.

German chamomile can be authenticated by morphological features if an intact plant or plant parts are presented. However, due to global herbal trade, most German chamomile products are sold in the form of powder and extract, which are not suitable for macroscopic examination. Numerous chemical-based chamomile authentication methods, which were designed to confirm and quantify bioactive compounds such as polyphenols, flavonoids, flavonoid glycosides, and coumarins, have been developed using UHPLC-UV-MS, GS-MS, HPTLC (Avula, et al. (2014). *J Pharm Biomed Anal*, 88, 278-288; Sagi, et al. (2014). *J Sep Sci*, 37(19), 2797-2804; Wang, et al. (2014). *Food Chem*, 152, 391-398, each of which is incorporated by reference herein in its entirety). However, these chemical methods have limitations: 1) The chemometrics of chamomile flower heads can be affected by seasonal variation, geographical location, and manufacturing process. 2) The interpretation of the chromatographic footprint requires experienced chemists, expensive instruments, sometimes computational modeling, and the process is often subjective. 3) Expensive and high quality chemical reference standards are required. Due to variations of chemical profile and no-standardized data interpretation, adulteration or similar botanical species contamination is often difficult to be detected by established chemical methods.

A species-level DNA-based authentication method has been explored for chamomile extract. However, it only tested one chamomile extract and did not consider common chamomile adulterants described herein (Novak, et al. (2007). *Food Res International*, 40(3), 388-392, incorporated herein by reference in its entirety).

In some embodiments of the methods and kits provided herein, a size distribution of DNA fragments in dietary supplements is detected. Some embodiments relate to design of DNA detection methods for authentication of target botanical species within a botanical material and for identification of common adulterants that may also be present in a botanical material. Due to the decrease in sequence specificity with fragment length, multiple mini-barcode regions may need to be checked simultaneously to achieve maximum confidence in botanical authentication. Moreover, since excipients or adulterants bring in potential non-target DNA, special consideration needs to be taken to either differentiate or ignore non-target DNA signals when authenticating target botanicals in dietary supplements. To address the above challenges, species-specific DNA-based botanical authentication methods have to be developed. Small amplicon PCR, which targets species in a defined test scope but ignores others, and Next-Generation Sequencing (NGS), which generates massive short diagnostic sequence-reads at molecular resolution for both targeted and non-target DNA, are DNA technologies that may be suitable for the authentication of botanical dietary supplements.

Accordingly, described herein are methods and kits for determining the size distribution of DNA fragments in botanical dietary supplements, especially those containing botanical extracts. The DNA fragment size of processed botanical materials decreases with the level of processing of the dietary supplement. In some embodiments, the DNA fragment size in sterilized powders may be below about 1200 bp, 1100 bp, 1000 bp, 900 bp, 800 bp, 700 bp, 600 bp, 500 bp, 500 bp, 300 bp, 200 bp, or 100 bp. In some embodiments, the DNA isolated from botanical extracts may range be about 300 bp, 290 bp, 280 bp, 270 bp, 260 bp, 250 bp, 240 bp, 230 bp, 220 bp, 210 bp, 200 bp, 190 bp, 180 bp, 170 bp, 160 bp, 150 bp, 140 bp, 130 bp, 120 bp, 110 bp, 100 bp, 90 bp, 80 bp, 70 bp, 60 bp, 50 bp, 40 bp, 30 bp, 20, or 10 bp, or within a range defined by any two of the aforementioned values.

Some embodiments provided herein relate to a method of authenticating a botanical material. As used herein, the term "authenticate," "authentication," or "authenticating" or derivatives thereof refers to a process of verifying the identity of a botanical in the material. Authentication can include verifying the presence of a certain target botanical or verifying the absence of a certain target botanical, such as determining whether or not a certain botanical is present in the material. Authentication can include a determination of whether an adulterant is present in the material. As used herein, an "adulterant" refers to a substance or chemical that is present in a material as a substitute or contaminant.

In some embodiments, the botanical material may be a nutraceutical composition or a dietary supplement that includes a botanical matter, a processed botanical extract, or a botanical powder, including a sterilized botanical powder. As used herein an "extract" or "botanical extract" refers to a solid, viscid, or liquid substance or preparation that includes a substance of plant, such as a root, a leaf, a stem, a flower, a seed, a fruit, or other portion of a plant. In some embodiments, the botanical material is a raw material, a powder, or an extract. As used herein the term "processed" includes treatment of a botanical substance to develop an herbal medicine, a nutraceutical composition, or a dietary supplement, including grinding, heating, fermenting, compacting, degrading, drying, wetting, or otherwise processing the botanical substance for preparation of the end botanical product for use or consumption by a consumer.

The term botanical pertains to or relates to plants. The term "plant," includes plants and plant parts including but not limited to plant cells and plant tissues such as leaves, stems, roots, flowers, pollen, fruit, bark, and seeds. The class of plants that can be used in the present invention is generally as broad as the class of higher and lower plants that may be commonly used in herbal medicines or in dietary supplements to provide a therapeutic or aesthetic benefit. In some embodiments, a botanical includes chamomile (including *Matricaria chamomilla* (also referred to as German chamomile or *Matricaria recutita*), feverfew (*Tanacetum parthenium*), Roman chamomile (*Chamaemelum nobile* syn *anthemis nobilis*), Chinese chamomile (*Chrysanthemum* x *morifolium,* or *Chrysanthemum indicum*), guarana (*Paullinia cupana*), parsley (*Petroselinum crispum*), celery (*Apium graveolens*), fennel (*Foeniculum vulgare*), Asian ginseng (*Panax ginseng*), American ginseng (*Panax quinquefolius*), Tienchi ginseng 1 (*Panax notoginseng*), Siberian ginseng (*Eleutherococcus senticosus*) Dong Quai (*Angelica sinensis*), garden angelica (*Angelica archangelica*), pubescent angelica (*Angelica pubescens*), dahurian angelica (*Angelica dahurica*), Chinese cinnamon (*Cinnamomum cassia*), true cinnamon (*Cinnamomum verum* syn *Cinnamomum zeylanicum*), Indonesian cinnamon (*Cinnamomum burmannii*), Ginkgo (*Ginkgo biloba*), Japanese sophora (*Sophora japonica*), buckwheat (*Fagopyrum esculentum*), jujube (*Ziziphus spinosa*), Indian jujube (*Ziziphus mauritiana*), Japanese raisin tree (*Hovenia dulcis*), ginger (*Zingiber officinale*), lesser galangal (*Alpinia officinarum*), greater galangal (*Alpinia galanga*), schisandra (*Schisandra chinensis*), southern schisandra (*Schisandra sphenanthera*), astragalus (*Astragalus membranaceus*), maca (*Lepidium meyenii*), radish (*Raphanus sativus*), turnip (*Brassica rapa*), peppermint (*Mentha piperita*), Chinese mint (*Mentha canadensis*), green tea (*Camellia sinensis*), rosemary (*Rosmarinus officinalis*), bilberry (*Vaccinium myrtillus*), blueberry (*Vaccinium corymbosum*), cranberry (*Vaccinium macrocarpon*), mulberry (*Morus alba*), or guarana (*Paullinia cupana*).

In some embodiments, the method of authenticating a botanical further includes isolating genomic DNA from a sample. As used herein, the term "isolate," "isolating," or "isolation," or derivatives thereof refers to material, such as a nucleic acid or a protein, which is: (1) substantially or essentially free from components which normally accompany or interact with the material as found in its naturally occurring environment, (2) substantially or essentially free from components which accompany or interact the material in a processed form, such as in a dietary supplement or from a substance used during the isolation process, or (3) if the material is in its natural environment, the material has been altered by deliberate human intervention to a composition and/or placed at a locus in the cell other than the locus native to the material. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). As used herein, the term "substantially purified" refers to molecules, either nucleic or amino acid sequences, that are removed from their natural environment or from a dietary supplement, isolated or separated, and are at least 60% free, preferably 75% free, and more preferably 90% free from other components with which they are naturally associated. An "isolated polynucleotide" is therefore a substantially purified polynucleotide.

Isolating botanical DNA fragments from a processed material can include use of isolation solvents, such as methanol, ethanol, water, acetone, or combinations thereof. In some embodiments, a kit for DNA isolation kit may be used, including for example, isolation using a DNeasy mericon Food Kit (Qiagen, Germantown, MD, USA) or the Cetyltrimethylammonium Bromide (CTAB) DNA isolation protocol. Other isolation techniques include lysis, heating, alcohol precipitation, salt precipitation, organic isolation, solid phase isolation, silica gen membrane isolation, CsCl gradient purification, or any combination thereof.

As used herein, the term "genomic DNA" refers to the chromosomal DNA sequence of a gene or segment of a gene, including the DNA sequences of non-coding as well as coding regions. Genomic DNA also refers to DNA isolated directly from cells or chromosomes or the cloned copies of all or part of such DNA. In some embodiments, the isolated genomic DNA is isolated from a processed botanical sample, such that the sample includes botanical DNA fragments. As used herein, fragmented DNA refers to portions of DNA having less than about 300 bp due to the processing of the botanical material, such as about 300 bp, 290 bp, 280 bp, 270 bp, 260 bp, 250 bp, 240 bp, 230 bp, 220 bp, 210 bp, 200 bp, 190 bp, 180 bp, 170 bp, 160 bp, 150 bp, 140 bp, 130 bp, 120 bp, 110 bp, 100 bp, 90 bp, 80 bp, 70 bp, 60 bp, 50 bp, 40 bp, 30 bp, 20, or 10 bp, or within a range defined by any two of the aforementioned values.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "aligning" means the comparison of two or more nucleotide sequences based on the presence of short or long stretches of identical or similar nucleotides.

ITS2 is located between 5.8S and 26S in plant rRNA genes, and originated as an insertion that interrupted the ancestral 23S rRNA gene. During rRNA maturation, ITS regions are excised and rapidly degraded. In some embodiments, a DNA fragment size is determined. In some embodiments, following a determination of the size of the DNA fragment size, a region to authenticate a botanical may include an ITS2 region, a rbcL region, a trnL-trnF region, a matK region, or a trnH-psbA region. These or additional regions may be selected depending on the target botanical and the test scope. In some embodiments, a two-tiered approach for authenticating a botanical is implemented. In some embodiments, a first tier includes aligning a plurality of contigs based on a coding region. In some embodiments, a coding region can include a rbcL and matK coding region. In some embodiments, a second tier includes aligning a plurality of contigs based on a non-coding region. In some embodiments, a non-coding region can include ITS2, trnL-trnF, and psbA-trnH non-coding regions.

The rbcL region is a coding gene for plant chloroplast, sometimes used as a locus for analysis of phylogenetics in plant taxonomy. Similarly, the matK region is a coding gene for plant plastidial, and retains a well-conserved domain for use in DNA barcoding.

The term "nucleic acid sequence" as used herein can refer to the nucleic acid material itself and is not restricted to the sequence information (for example, the succession of letters chosen among the five base letters A, C, G, T, or U) that biochemically characterizes a specific nucleic acid, for example, a DNA or RNA molecule. As used herein, the terms "polynucleotide", "nucleic acid", or "oligonucleotide" refers to a linear polymer of natural or modified monomers or linkages, including deoxyribonucleic acid, deoxyribonucleosides, ribonucleosides, polyamide nucleic acids, and the like, joined by inter-nucleosidic linkages and have the capability of specifically binding to a target polynucleotide by way of a regular pattern of monomer-to-monomer interactions, such as Watson-Crick type of base pairing, and capable of being ligated to another oligonucleotide in a template-driven reaction. Usually monomers are linked by phosphodiester bonds or analogs thereof to form oligonucleotides ranging in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes deoxythymidine, unless otherwise noted. The letters A, C, G, and T can be used to refer to the bases themselves, to nucleosides, or to nucleotides including the bases, as is standard in the art. In naturally occurring polynucleotides, the inter-nucleoside linkage is typically a phosphodiester bond, and the subunits are referred to as "nucleotides."

The terms "5' ends" and "3' ends" as used herein, refer to the termini of oligonucleotides because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

In some embodiments, the method further includes ligating adapters to the botanical DNA fragments to generate adapter-ligated DNA fragments. The term "ligate" "ligating" or "ligation" refers to any method or composition wherein two different double stranded nucleotides have been joined into a single oligonucleotide strand. The term "adapter," describes a short, oligonucleotide polynucleotide segment that can be joined to a polynucleotide molecule at either a blunt end or cohesive end. Adapters may contain restriction enzyme recognition sequences within the polynucleotide fragment. The size of the adapter can vary from about ten to about one-hundred and fifty nucleotides in length. Adapters can either be single stranded or double stranded. Adapter-ligated DNA fragments includes the botanical DNA fragments isolated from the processed botanical material ligated to the adapters, for example, as described and shown in FIG. 3A. Ligation may be performed under standard conditions and using standard reagents. In some embodiments, ligation may be performed over a period of about 30 seconds, 1 minute, 5 minutes, 10 minutes, 30 minutes, 1 hour, 2 hours, 3 hours, 4 hours, 5 hours, 6 hours, 7 hours, 8 hours, 9 hours, 10 hours, 11 hours, 12 hours, 15 hours, 18 hours, or 24 hours, or an amount of time within a range defined by any two of the aforementioned values. In some embodiments, ligation may be performed at about 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C., or an amount within a range defined by any two of the aforementioned values.

In some embodiments, the method further includes amplifying the adapter-ligated DNA fragments to detect the botanical DNA fragments. As described herein, botanical DNA fragments are present in dietary supplements in low quantity or low quality, or both, and therefore, are unable to be readily detected by conventional techniques. For example, in some embodiments, the botanical DNA fragments may be excessively degraded or sufficiently fragmented as to be incapable of being detected. In addition, in some embodiments, a target botanical DNA fragments may be present in a botanical product (for example, an herbal medicine, a nutraceutical composition, or a dietary supplement) in an amount of about 100 ng, 10 ng, 1 ng, 900 pg, 800 pg, 700 pg, 600 pg, 500 pg, 400 pg, 300 pg, 200 pg, 100 pg, 10 pg, 1 pg, 900 fg, 800 fg, 700 fg, 600 fg, 500 fg, 400 fg, 300 fg, 200 fg, 100 fg, or less, or an amount within a range defined by any two of the aforementioned values. In this way, botanical DNA fragments in processed botanical materials are sometimes referred to as "invisible," referring to the inability to visualize or detect the fragments. Ligating adapters to the fragments followed by amplification enables detection of the fragments. As used herein the term "detection" or "visualization" refers to the ability to observe DNA fragments. The detection of the fragments allows for downstream analysis. Detection of the fragments can be performed by DNA detection techniques, including by Southern blot, the analysis of DNA on agarose or acrylamide gels to fractionate the DNA according to size, which may be followed by transfer and immobilization of the DNA from the gel to a solid support, such as nitrocellulose or a nylon membrane. The immobilized DNA may further be probed with a labeled oligodeoxyribonucleotide probe or DNA probe to detect DNA species complementary to the probe used. The DNA may be cleaved with restriction enzymes prior to electrophoresis. Following electrophoresis, the DNA may be partially depurinated and denatured prior to or during transfer to the solid support.

In some embodiments, the amplified adapter-ligated DNA is used to evaluate total DNA after amplification. As used herein, the term "evaluate" includes determining, assessing, quantifying, or counting the level or amount of DNA present in a sample, or determining, assessing, or quantifying the length of DNA fragments in a sample. Evaluating a sample may include use of a fluorometer, spectrophotometer, or other bioanalyzer capable of determining the concentration and length of DNA fragments in a sample. In some embodiments, fragment length may be assessed by TapeStation™, which provides average size in base pairs.

In some embodiments, the method further includes hybridizing a species-specific primer set to a target nucleic acid sequence with the botanical DNA fragments. As used herein, the term "hybridizing", "hybridize", "hybridization", "annealing", or "anneal" are used interchangeably in reference to the pairing of complementary nucleic acids using any process by which a strand of nucleic acid joins with a complementary strand through base pairing to form a hybridization complex. Hybridization and the strength of hybridization (for example, the strength of the association between the nucleic acids) is impacted by such factors as the degree of complementarity between the nucleic acids, stringency of the conditions involved, the melting temperature ($T_m$) of the formed hybrid, and the G:C ratio within the nucleic acids.

As used herein, the term "amplification primer" and "primer" refers to an oligonucleotide, which is capable of site-specifically annealing to an RNA or DNA region adjacent a target sequence, and serving as an initiation primer for DNA synthesis under suitable conditions in which synthesis of a primer extension product is induced, e.g., in the presence of nucleotides and a polymerization-inducing agent such as a DNA-dependent DNA polymerase and at suitable temperature, pH, metal concentration, and salt concentration. Typically, a PCR reaction employs a pair of amplification primers also known as "primer pairs" or "primer sets" including an "upstream" or "forward" primer and a "downstream" or "reverse" primer, which delimit a region of the RNA or DNA to be amplified.

Primer sequences for chamomile authentication may include the nucleic acid sequences as set forth in Table 1. In some embodiments, the primer set for detection of DNA fragment size is a P5 adapter sequence and a P7 adapter sequence as set forth in Table 1.

TABLE 1

Targeted PCR primer sets used for chamomile authentication.

| Primer Target | Purpose | Direction | Primer Sequence (5'→3') | SEQ ID NO | Amplicon (bp) |
|---|---|---|---|---|---|
| German Chamomile | Authentication | Forward | GTCGTCGGTCGCAAGGATAAG | 1 | 103 |
| | | Reverse | TAAACTCAGCGGGTAGTCCC | 2 | |
| Feverfew | Contamination Detection | Forward | GGATATTGGTCTCCCGTGCT | 3 | 125 |
| | | Reverse | AGAGTTTTTCCTTGCGACTAACAC | 4 | |

TABLE 1-continued

Targeted PCR primer sets used for chamomile authentication.

| Primer Target | Purpose | Direction | Primer Sequence (5'→3') | SEQ ID NO | Amplicon (bp) |
|---|---|---|---|---|---|
| Roman Chamomile | Contamination Detection | Forward | TGTCGCACGTTGCTAGGAAGCA | 5 | 104 |
| | | Reverse | TAAACTCAGCGGGTAGTCCC | 6 | |
| Chinese Chamomile | Contamination Detection | Forward | GTCGAAGCGTCGTCAAGAGA | 7 | 73 |
| | | Reverse | TTTGTTTCGTGCTGTGCTCG | 8 | |
| Adapter Amplification Sequence | P5 | Forward | AATGATACGGCGACCACCGA | 9 | N/A |
| | P7 | Reverse | CAAGCAGAAGACGGCATACGA | 10 | |

Thus, in some embodiments, the species-specific primer set is a primer set capable of hybridizing to German chamomile, such that the primer set includes a forward primer defined by a nucleic acid sequence set forth by SEQ ID NO: 1 and a reverse primer defined by a nucleic acid sequence set forth by SEQ ID NO: 2. In some embodiments, the species-specific primer set is a primer set capable of hybridizing to feverfew, such that the primer set includes a forward primer defined by a nucleic acid sequence set forth by SEQ ID NO: 3 and a reverse primer defined by a nucleic acid sequence set forth by SEQ ID NO: 4. In some embodiments, the species-specific primer set is a primer set capable of hybridizing to Roman chamomile, such that the primer set includes a forward primer defined by a nucleic acid sequence set forth by SEQ ID NO: 5 and a reverse primer defined by a nucleic acid sequence set forth by SEQ ID NO: 6. In some embodiments, the species-specific primer set is a primer set capable of hybridizing to Chinese chamomile, such that the primer set includes a forward primer defined by a nucleic acid sequence set forth by SEQ ID NO: 7 and a reverse primer defined by a nucleic acid sequence set forth by SEQ ID NO: 8.

Primer sequences for targeted amplicon sequencing based botanical authentication may include the nucleic acid sequences as set forth in Table 2. In some embodiments, the primer set may be flanked my M13 sequence or Illumina adapter sequence to facilitate sequencing.

TABLE 2

Targeted sequencing primer sets used for botanical authentication.

| Primer Target | Region ID | Direction | Primer Sequence (5'→3') | SEQ ID NO |
|---|---|---|---|---|
| Ginseng | Ginseng1 | Forward | TCGAGTCTTTGAACGCAAGTT | 11 |
| | | Reverse | GACACGGGAGGCCATTATC | 12 |
| Cinnamomum | Cinnamomum1 | Forward | GGAGCGGAGACTGGCCGT | 13 |
| | | Reverse | GCACGGTGTCCTCCTTTTCTG | 14 |
| | Cinnamomum2 | Forward | CCCGTCGCCGATCGTAC | 15 |
| | | Reverse | CTGCGGGCGGGTATGGTC | 16 |
| Parsley | Parsley1 | Forward | TTTGGGCGGAAATTGGCCTC | 17 |
| | | Reverse | TTACAACCACCGATGTCACGAC | 18 |
| Ginkgo | Ginkgo1 | Forward | CGAGTAACTCCTCAACCTGG | 19 |
| | | Reverse | TTGTAACGATCAAGACTGGTAAG | 20 |
| TangKuei | TangKuei1 | Forward | AATACCCTCWTGTCTTGTCG | 21 |
| | | Reverse | TGCTTAAACTCAGCGGGTAG | 22 |
| | TangKuei2 | Forward | GGACTTACCAGCCTTGATCG | 23 |
| | | Reverse | TCAAAAAGGTCTAATGGGTAAGC | 24 |
| Astragalus | Astragalus1 | Forward | TGAAGAAGGTTCTGTTACTAACATGT | 25 |
| | | Reverse | CGGGCCTTGGAAAGTTTTAACA | 26 |
| | Jujube1 | Forward | GTCACACAACGTTGCCCC | 27 |
| | | Reverse | CACGGGAGGCCAGCAT | 28 |
| Schisandra | Schisandra1 | Forward | TCGAGTTTTTGAACGCAAGTT | 29 |
| | | Reverse | TCCTCGCAAACACCATACAC | 30 |
| | Schisandra2 | Forward | ATCCTTGTGATGCCGAAAAC | 31 |
| | | Reverse | ATCAACGCATGGCACAAGAC | 32 |
| | Schisandra3 | Forward | GAAATTGGTTATTGTATTGTTTCTTCA | 33 |
| | | Reverse | TCACTGGAATAAATGTCGATGC | 34 |
| | Schisandra4 | Forward | TCTAGCTCTCTGTATGAAATGACTAAA | 35 |
| | | Reverse | ATCCGCCCCTCCTCTCTAT | 36 |

TABLE 2-continued

Targeted sequencing primer sets used for botanical authentication.

| Primer Target | Region ID | Direction | Primer Sequence (5'→3') | SEQ ID NO |
|---|---|---|---|---|
| Ginger | Ginger1 | Forward | CGATCGGCACTAAGGAACAA | 37 |
| | | Reverse | CGAGATATCCATTGCCGAGAG | 38 |
| | Ginger2 | Forward | AGCATTCCGAGTAACTCCTCA | 39 |
| | | Reverse | AGTCCATCAGTCCACACAGT | 40 |
| | Ginger3 | Forward | TGAACTCACAACCATATGCGT | 41 |
| | | Reverse | TTCTTCACATGTACCTGCAGT | 42 |
| | Ginger4 | Forward | TGAACTCACAACCATTTATGCGT | 43 |
| | | Reverse | TTCTTCACATGTACCTGCAGT | 44 |
| Maca | Maca4 | Forward | CTGGGCGTCACAAATCGT | 45 |
| | | Reverse | GGTAACACACGGGAGACCAG | 46 |
| Jujube | Jujube1 | Forward | GTCACACAACGTTGCCCC | 47 |
| | | Reverse | CACGGGAGGCCAGCAT | 48 |
| Chamomile | Ginger4 | Forward | GGTGGTCGTAAAAACCCTCG | 49 |
| | | Reverse | TGCTTAAACTCAGCGGGTAGT | 50 |

In some embodiments, a primer set is designed for target species-specific PCR amplification, wherein the target species includes one or more of a target botanical, including for example, ginger (*Zingiber officinale*), chamomile (including *Matricaria chamomilla* (also referred to as German chamomile or *Matricaria recutita*), *Tanacetum parthenium* (feverfew), *Chamaemelum nobile* (*Anthemis nobilis* or Roman chamomile), *Chrysanthemum* x *morifolium,* or *Chrysanthemum indicum* (Chinese chamomile)), guarana (*Paullinia cupana*), parsley (*Petroselinum crispum*), Asian ginseng (*Panax ginseng*), or schisandra (*Schisandra chinensis*), Maca (*Lepidium_meyenii*), Astragalus (*Astragalus propinquus*), Ginkgo (*Ginkgo biloba*), TangKuei (*Angelica sinensis*), True Cinnamomum (*Cinnamomum_verum*).

In some embodiments, the sequenced signature region needs to be compared to a signature sequence database Table 3 to authenticate botanicals.

TABLE 3

Signature sequence reference for botanical authentication.

| Scope | Region | Species | Signature Sequences | SEQ ID NO |
|---|---|---|---|---|
| Cinnamomum | Cinnamomum 1 | *Cinnamomum aromaticum* | CCGTGCCCGGGTGACCGGCGCGCGGTCGG | 83 |
| | | *Cinnamomum burmannii* | CCGTGCCCGAGCGATCGGCGCGCGGTCGG | 84 |
| | | *Cinnamomum verum* | CCGTGCCCGGGTCATCGGCGCGCGGTCGG | 85 |
| | Cinnamomum 2 | *Cinnamomum aromaticum* | GTCGCGCCCGCAATCCGCCGCGCGGTGCAAGCCCGTGG | 86 |
| | | *Cinnamomum burmannii* | GTCGCGCCCGCAATCCGCCGCGCGGTGCCACCCGTGG | 87 |
| | | *Cinnamomum verum* | GCAGCGCCCGCATTCCGCCGCGCGGTGCCGCCCGTGG | 88 |
| Ginseng | Ginseng1 | *Panax quinquefolius* | GCGCCCGAAGCCATTAGGCCGAGGGCACGTCTGCCTGGGCGTCACGCATCGCGTCGCCCCCCAACCCATCACTCCTTTGCGGGAGTCGAGGCGGAGGGGCG | 89 |
| | | *Panax ginseng* | GCGCCCGAAGCCATTAGGCCGAGGGCACGTCTGCCTGGGCGTCACGCATCGCGTCGCCCCCCAACCCATCACTCCCTTGCGGGAGTTGAGGCGGAGGGGCG | 90 |
| | | *Eleutherococcus senticosus* | GCGCCCGAAGCCATTAGGCCGAGGGCACGTCTGCCTGGGCGTCACGCATCGCGTCGCCCCCCAACCCTGCACTCCCTCATGGGAGTCATGACTGAGGGGCG | 91 |
| | | *Panax notoginseng* | GCGCCCGAAGCCATTAGGCCGAGGGCACGTCTGCCTGGGCGTCACGCATCGCGTCGCCCCCCAACCCATCATTCCCTCGCGGGAGTCGATGCGGAGGGGCG | 92 |

TABLE 3-continued

Signature sequence reference for botanical authentication.

| Scope | Region | Species | Signature Sequences | SEQ ID NO |
|---|---|---|---|---|
| Parsley | Parsley1 | *Petroselinum crispum* | CCGTGCCTTGCTGCGCGGCTGGTGCAA AAGTGAGTCTCCGACGACGGAC | 93 |
| | | *Foeniculum vulgare* | CCGTGCCTTGTTGTGCGGCTGGTGCAA AAGCGAGTCTCTGGCGGTGGAC | 94 |
| | | *Apium graveolens* | CCGTGCCGTGTTGTGCGGTTGGCGCAA AAGCGAGTCTCCGGCGACGGAC | 95 |
| Ginkgo | Ginkgo1 | *Ginkgo biloba* | AGTGCCACCTGAGGAAGCGGGAGCTGC AGTAGCTGCCGAATCTTCCACTGGTAC ATGGACCACTGTTTGGACCGATGGA | 96 |
| | | *Sophora japonica* | AGTTCCGCCTGAAGAAGCAGGTGCCGC GGTAGCTGCTGAATCTTCTACTGGTAC ATGGACAACTGTGTGGACCGATGGG | 97 |
| | | *Fagopyrum esculentum* | AGTTCCACCAGAAGAAGCAGGGGCCGC GGTAGCTGCCGAATCTTCTACTGGTAC ATGGACAACTGTGTGGACCGATGGA | 98 |
| Ginger | Ginger1 | *Zingiber officinale* | CGAACTCGGAAGCGGAGGGCCCCTCGC CGTGCGCAGGGGAGCCCGATGCGTCGG AGATTCCTCGGAATCAATCAATCAAAC GA | 99 |
| | | *Zingiber officinale* | CGAACTCGGAAGCGGAGGGCCCCTCGG CGTGCGCAGGGGAGCCCGATGCGTCGG AGATTCCTCGGAATCAATCAATCAAAC GA | 100 |
| | | *Zingiber officinale* | CGAACTCGGAAGCGGAGGGCCCCTCGG CGTGCGCAGGGGAGCCCGATGCGTCGG AGATTCCTCGGAATCAATCAATCAATC AAACGA | 101 |
| | | *Zingiber officinale* | CGAACTCGGAAGCGGAGGGCCCCTCGC CGTGCGCAGGGGAGCCCGATGCGTCGG AGATTCCTCGGAATCAATCAATCAATC AAACGA | 102 |
| | | *Alpinia officinarum* | TGAACTCAGAAGCAGATGGCCCTCAGT GTGCTCGGGGAGGCCAATGCATCGGAG ATGCCTCAAATCAAATGA | 103 |
| | | *Alpinia officinarum* | TGAACTCAGAAGCAGATGGCCCTCAGC GTGCTCGGGGAGGCCAATGCACCGGAG ATGCCTCAAATCAAATGA | 104 |
| | | *Alpinia officinarum* | TGAACTCAGAAGCAGATGGCCCTCAGC GTGCTCGGGGAGGCCAATGCATCGGAG ATGCCTCAAATCAAATGA | 105 |
| | | *Alpinia galanga* | TAAACTGAGAAGCAAAGGGCCCTCGGT GTGTGCGGGGAGCCCAATGCGTCGGAG AAGCCTCGAAATCAAATGA | 106 |
| | | *Alpinia galanga* | TAAACTGAGAAGCAAAGGGCCCTCGCT GTGTGCGGGGAGCCCAATGCGTCGGAG AAGCCTCGAAATCAAATGA | 107 |
| | | *Alpinia galanga* | TAAACTGAGAAGCAAAGGGCCCTCGCT GTGTGCGGGGAGCCCAATGCGTCGGAG AAGCTTCGAAATCAAATGA | 108 |
| | Ginger2 | *Zingiber officinale* | ACCTGGAGTTCCACCCGAAGAAGCAGG GGCTGCGGTAGCTGCCGAATCTTCTAC TGGTACATGGACA | 109 |
| | | *Alpinia officinarum* | ACCTGGAGTTCCACCCGAAGAAGCAGG GGCTGCGGTAGCAGCCGAATCCTCTAC TGGTACATGGACA | 110 |
| | | *Alpinia galanga* | ACCTGGAGTTCCACCCGAAGAAGCAGG AGCTGCGGTAGCAGCCGAATCCTCTAC TGGTACATGGACA | 111 |
| | Ginger3&4 | *Zingiber officinale* | TGGAGAGACCGTTTCCTATTTTGTGCT GAAGCACTTTTTAAAGCGCAGGCCGAA ACAGGTGAAATTAAAGGACATTACTTG AATGCT | 112 |
| | | *Alpinia officinarum* | TGGAGAGACCGTTTCGTATTTTGTGCT GAAGCACTTTATAAAGCGCAGGCCGAA ACAGGTGAAATTAAAGGGCATTACTTG AATGCT | 113 |
| | | *Alpinia galanga* | TGGAGAGACCGTTTCGTATTTTGTGCT GAAGCAATTTATAAAGCGCAGGCCGAA ACAGGTGAAATTAAAGGGCATTACTTT AATGCT | 114 |

TABLE 3-continued

Signature sequence reference for botanical authentication.

| Scope | Region | Species | Signature Sequences | SEQ ID NO |
|---|---|---|---|---|
| Jujube | Jujube1 | Ziziphus jujuba var spinosa | CCATCCCAACCTCGACCTCGAGGCGAA GAGGGGGCGG | 115 |
| | | Ziziphus jujuba var spinosa | CCATCCCAACCTCGAGGCGAAGAGGGG GCGG | 116 |
| | | Ziziphus mauritiana | CCCCAACCTCCGCCTCGGAAGGGAAGA GGGGGCGG | 117 |
| | | Ziziphus mauritiana | CCCAACCTCCGCCTCGGAAGGGAAGAG GGGGCGG | 118 |
| | | Ziziphus mauritiana | CCCAACCTCCTCCTCGGAAGGGAAGAG GGGGCGG | 119 |
| | | Hovenia dulcis | CCCAACCTCGACCCCGAGGGCGGGTGG GC | 120 |
| TangKuei | TangKuei1 | Angelica sinensis | CGCGAATCCGCGTCATCTTAGTGAGCT CAAGGACCCTTAGGCGGCACACACTTT GTGCACTTCGAATGTGACCCCAGGTCA GGCGGGA | 121 |
| | | Angelica sinensis | CGCGAATCCGCGTCATCTTAGTGAGCT CAAGGACCCTTAGGCGGCACACACTTT GTGCACTTCGAATGTGACCCCAGGTCA GGCGGGA | 122 |
| | | Angelica pubescentis | CGCGAATCCTCGTCATCTTAGCGAGCT CCAGGACCCTTAGGTAGCACATACTCT GTGCGCTTCGACTGTGACCCCAGGTCA GGCGGGA | 123 |
| | | Angelica pubescentis | CGCGAATCCTCGTCATCTTAGCGAGCT CCAGGACCCTTAGGTAGCACATACTCT GTGCGCTTCGACTGTGACCCCAGGTCA GGCGGGA | 124 |
| | | Angelica dahuricae | CGTGAATCCTTGTCATCTTAGAGAGCT CCAGGACCCTTAGGCAGCACGTACTCT GTGCGCTTCGACTGTGACCCCAGGTCA GGCGGGA | 125 |
| | | Angelica dahuricae | CGTGAATCCTTGTCATCTTAGAGAGCT CCAGGACCCTTAGGCAGCACGTACTCT GTGCGCTTCGACTGTGACCCCAGGTCA GGCGGGA | 126 |
| | TangKuei2 | Angelica sinensis | TTACAAAGGGCGCTGCTACGAAATCGA GCCCGTTGCTGGAGAAGAAAATCAATA TATCGCTTATGTA | 127 |
| | | Angelica pubescentis | TTACAAAGGGCGCTGCTACGGAATCGA GCCCGTTGCTGGAGAAGAAAATCAATT TATCGCTTATGTA | 128 |
| | | Angelica dahuricae | TTACAAAGGGCGCTGCTACGGAATCGA GCCCGTTGCTGGAGAAGAAAATCAATT TATCGCTTATGTA | 129 |
| Schisandra | Schisandra1 | Schisandra chinensis | GCGCCCGAGGCCACCTGGCCAAGGGCA CGCCTGCCTGGGCGTCACGCTTTGCGA CGCTCCCCTCCCTCCCATTCTCCTTTT TGG | 130 |
| | | Schisandra sphenanthera | GCGCCCGAGGCCACCTGGCCAAGGGCA CGCCTGCCTGGGCGTCACGCTTTGCGT CGCTCCCCTCCCTCCCATTCTCCCTTT TTG | 131 |
| | Schisandra2 | Schisandra chinensis | CCTTCCCCTCTCATTGCTACCTTGTAT GACACGCCTTG | 132 |
| | | Schisandra sphenanthera | CCTTCCCCTCTCATTGCTACCTTGTAT GACATGCTTTG | 133 |
| | Schisandra3 | Schisandra chinensis | ATTGACAATTGAGTAGTGTTTTGTTC | 134 |
| | | Schisandra sphenanthera | ATTGACAATTGAGTAGTGTTTTATTC | 135 |
| | Schisandra4 | Schisandra chinensis | TACAAAATACAAAATTATGAATAGTCG AAATGGAATCTTTTGG | 136 |
| | | Schisandra sphenanthera | TACAAAATAAAAAAATTTTGAATAGTC GAAATGGAATCTTTTTG | 137 |

TABLE 3-continued

Signature sequence reference for botanical authentication.

| Scope | Region | Species | Signature Sequences | SEQ ID NO |
|---|---|---|---|---|
| Astragalus | Astragalus1 | *Astragalus membranaceus* | TTACCTCCATTGTTGGTAATGTATTTGGATTCAAGGCTTTGCGCGCTCTACGTTTGGAGGATTTGCGAATCCCTACTGCTTA | 138 |
| Maca | Maca1 | *Lepidium meyenii* | CGTTCCCCTCACAAAATTTTGCGAGTGCGGGACGGAAG | 139 |
| | | *Raphanus sativus* | CGTCCCCCCATCCTCTCGAGGATATAGGACGGAAG | 140 |
| | | *Brassica rapa* | CGTCCCCCCATCCTCTCGAGGATATGGGATGGAAG | 141 |
| | | *Brassica rapa* | CGTCCCCCCATCCTCTCGAGGATATGGGACGGAAG | 142 |
| Chamomile | Chamomile1 | *Matricaria chamomilla* | TTCTTTGTTTTGTGTCGTCGGTCGCAAGGATAAGCTCTAAAAACCCCAATGTGTTGTCTTAGGATGACGCTTCGACCGCGACCCCAGGTCAGGCGGG | 143 |
| | | *Matricaria chamomilla* | TTCTTTGTTTTGTGTCGTCGGTCGCAAGGATAAGCTCTGTAAAACCCCAATGTGTTGTCTTAGGATGACGCTTCGACCGCGACCCCAGGTCAGGCGGG | 144 |
| | | *Matricaria chamomilla* | TTCTTTGTTTTGTGTCGTCGGTCGCAAGGATAAGCTCTAAAAACCCCAATGTGTCGTCTTAGGATGACGCTTCGACCGCGACCCCAGGTCAGGCGGG | 145 |
| | | *Tanacetum parthenium* | TTCTTTGTTCTGTGTTAGTCGCAAGGAAAAACTCTTCAAATACCCTAATGTGTTGTCTTCGGATGACGCTTCGACCGCGACCCCAGGTCAGGCGGG | 146 |
| | | *Tanacetum vulgare* | TTCTTTGTTCTGTGTTAGTCGCAAGGAAAAACTCTTCAAATACCCCAATGTGTTATCTTAGGATGACGCTTCGACCGCGACCCCAGGTCAGGCGGG | 147 |
| | | *Chamaemelum nobile* | TTCTTTGTTTTGTGTCGCACGTTGCTAGGAAGCACTCTCTAAATAACCCATTGTGTTGTCTTAGGATGACGCTTCGACCGCGACCCCAGGTCAGGCGGG | 148 |
| | | *Chamaemelum nobile* | TTCTTTGTTTTGTGTCGCACGTCGCTAGGAAGCACTCTCTAAATAACCCATTGTGTTGTCTTAGGATGACGCTTCGACCGCGACCCCAGGTCAGGCGGG | 149 |
| | | *Chamaemelum nobile* | TTCTTTGTTTTGTGTCGCACGTTGCTAGGAAGCACTCTCTAAATAACCCATTGTGTTGTCTTAGGATGACGCTTCGACCGCGACCTCAGGTCAGGCGGG | 150 |
| | | *Chrysanthemum indicum* | TCTTTTGTTCGTGCTGTTGCTCGCAAGGTAAACTCTTTAAAAACCCCAATGTGCCGTCTCTTGACGACGCTTCGACCGCGACCCCAGGTCAGGCGGG | 151 |
| | | *Chrysanthemum x morifolium* | TCTTTTGTTCGTGCTGTTGCTCGCAAGGTAAACTCTTTAAAAACCCCAATGTGTCGTCTCTTGACGACGCTTCGACCGCGACCCCAGGTCAGGCGGG | 152 |

Primer sequences for tiling PCR and sequencing of *Camellia sinensis* two-tiered barcodes may include the nucleic acid sequences as set forth in Table 4. In some embodiments, the primer set may be flanked by M13 sequence or Illumina adapter sequence to facilitate sequencing.

TABLE 4

Tiling sequencing primers for tea two-tiered barcodes: ITS2 and rbcL

| Sequence (5' → 3') | Region | SEQ ID No. |
|---|---|---|
| AGCCATTAGGTTGAGGGCAC | Tea ITS2 | 51 |
| CGCAGCCCTTCTTCCCC | Tea ITS2 | 52 |
| AATTGCAGAATCCCGCGAAC | Tea ITS2 | 53 |
| CAACGTGAGACGCCCAGG | Tea ITS2 | 54 |
| GGAAGAAGGGCTGCGGG | Tea ITS2 | 55 |
| ACGGTTTGTCAACCACCACT | Tea ITS2 | 56 |
| TCGGCCCAAAAGCGAGTC | Tea ITS2 | 57 |
| CGATAGGGTCACGACAGGC | Tea ITS2 | 58 |
| AGGCCTGTCGTGACCCTATC | Tea ITS2 | 59 |
| TCCTCCGCTTATTGATATGCTT | Tea ITS2 | 60 |
| GGGATTACCCGCTGAGTTTA | Tea ITS2 | 61 |
| GTCGCTCGATTTTCAAGCTG | Tea ITS2 | 62 |
| TGTTGGATTCAAAGGTGGTG | Tea rbcL | 63 |
| CGGAGTTACTCGGAATGCTG | Tea rbcL | 64 |
| CTGATATCTTGGCAGCATTCC | Tea rbcL | 65 |
| GTCCATGTACCAGTAGAAGATTCG | Tea rbcL | 66 |
| GAGTAACTCCGCAACCTGGA | Tea rbcL | 67 |
| ATCGCCCTTTGTAACGATCA | Tea rbcL | 68 |
| GCTGCCGAATCTTCTACTGG | Tea rbcL | 69 |
| TGACTTTCTTCTCCAGCAACG | Tea rbcL | 70 |
| ACTGTGTGGACCGATGGACT | Tea rbcL | 71 |
| TTCAAAAAGGTCTAAAGGATACGC | Tea rbcL | 72 |
| CCGTTGCTGGAGAAGAAAGT | Tea rbcL | 73 |
| CAGGGCTTTGAACCCAAATA | Tea rbcL | 74 |
| GCGTATCCTTTAGACCTTTTGAA | Tea rbcL | 75 |
| ATTCGCAGATCTTCCAGACG | Tea rbcL | 76 |
| TCCATTGTGGGTAATGTATTTGG | Tea rbcL | 77 |
| TTTCAACTTGGATGCCATGA | Tea rbcL | 78 |
| TCTGGAAGATCTGCGAATCC | Tea rbcL | 79 |
| CAGGGGACGACCATACTTGT | Tea rbcL | 80 |
| CGCCTCATGGCATCCAAGTT | Tea rbcL | 81 |
| CCACCGCGGAGACATTCATAA | Tea rbcL | 82 |

In some embodiments, the sequenced tiling amplicon needs to be aligned to full-length barcode regions for authenticating botanicals.

In some embodiments, a PCR-based primer or species-specific primers may be designed based on the detection of DNA fragment size. In some embodiments, for example, design of the primers may be performed with a program, such as the program "Primer-BLAST", on the basis of target species consensus sequence as PCR template and non-target consensus sequences as exclusion sequences.

In some embodiments, the method further includes amplifying the target nucleic acid sequence. As used herein, the term "amplifying" refers to a process whereby a portion of a nucleic acid is replicated using, for example, any of a broad range of primer extension reactions. Exemplary primer extension reactions include, but are not limited to, PCR. Unless specifically stated, "amplifying" refers to a single replication or to an arithmetic, logarithmic, or exponential amplification. The term "in silico" refers to processes taking place via computer calculations Amplification can be performed using standard amplification reactions and conditions. In some embodiments, amplification is performed at 1 cycle at 95° C., followed by 12 cycles of 30 seconds at 95° C., 30 seconds at 58° C., 2 minutes at 72° C., and a final extension step at 72° C. for 5 minutes. The cycle number, time, and temperature can be modified, and the steps described herein are provided by way of example, and not to be limiting.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

In some embodiments, the method further includes sequencing the target nucleic acid sequence. As used herein "sequence determination", "determining a nucleotide base sequence", "sequencing", identifying and like terms includes determination of partial as well as full sequence information of a botanical DNA fragment. That is, the term includes sequence comparisons, fingerprinting, and similar determination of information about a target polynucleotide, as well as the express identification and ordering of each nucleoside of the target polynucleotide within a region of interest. In certain embodiments, "sequence determination" includes identifying a single nucleotide, while in other embodiments more than one nucleotide is identified. Identification of nucleosides, nucleotides, and/or bases are considered equivalent herein. It is noted that performing sequence determination on a polynucleotide typically yields equivalent information regarding the sequence of a perfectly complementary polynucleotide and thus is equivalent to sequence determination performed directly on a perfectly complementary polynucleotide.

As used herein, the term "sequence alignment" refers to a listing of multiple DNA or amino acid sequences and aligns them to highlight their similarities. The listings can be performed in silico and can be made using bioinformatics computer programs.

As used herein, "comparing" refers to making an assessment of how sequences in a sample relates to sequences in a standard, control, or comparative sample. For example, "comparing" may refer to assessing whether the sequence from one sample is the same as, varies from at specific nucleotide or amino acid positions, or differs from the sequence in standard, control, or comparative sample.

Some embodiments provided herein relate to a kit for authentication of botanical DNA fragments isolated from a botanical product, such as from a dietary supplement, herbal medicine, or nutraceutical composition that includes a botanical extract. Any of the reagents, compositions, or materials described herein may be included in a kit. In a non-limiting example, a kit may include the following components, each component being in a suitable container: isolation reagents for isolating botanical DNA fragments from a processed botanical sample; ligation-adapters for ligating adaptors to the botanical DNA fragments; end-repair and ligation reagents; a species-specific primer set for hybridizing to a target nucleic acid sequence; or amplification reagents for amplifying ligated adapter DNA fragments.

In some embodiments, the isolation reagents may itself be a kit, for example, a DNA isolation kit such as a DNeasy mericon Food Kit (Qiagen, Germantown, MD, USA) or similar DNA isolation kit. In some embodiments, the isolation reagents may include isolation solvents, including, for example, methanol, ethanol, water, acetone, or combinations thereof.

In some embodiments, the ligation-adapters may include a prepared kit, for example a Quick Ligation Kit including ligation enzymes (ligase), a ligation buffer, and adapters of a known DNA sequence. In some embodiments, the ligation-adapters may include specified ligase, ligation buffers, and adapters of a known DNA sequence, and further including end repair reagents.

In some embodiments, the species-specific primer set includes a primer set of a known DNA sequence, including a forward and a reverse primer for a known botanical target. For example, in some embodiments, a primer set can include a forward primer including a nucleic acid sequence as defined by SEQ ID NO: 1 and a reverse primer including a nucleic acid sequence as defined by SEQ ID NO: 2. In some embodiments, a primer set can include a forward primer including a nucleic acid sequence as defined by SEQ ID NO: 3 and a reverse primer including a nucleic acid sequence as defined by SEQ ID NO: 4. In some embodiments, a primer set can include a forward primer including a nucleic acid sequence as defined by SEQ ID NO: 5 and a reverse primer including a nucleic acid sequence as defined by SEQ ID NO: 6. In some embodiments, a primer set can include a forward primer including a nucleic acid sequence as defined by SEQ ID NO: 7 and a reverse primer including a nucleic acid sequence as defined by SEQ ID NO: 8.

In some embodiments, the amplification reagents can include reagents used in nucleic acid amplification reactions and may include, but are not limited to, buffers, reagents, enzymes having reverse transcriptase and/or polymerase activity or exonuclease activity, enzyme cofactors such as magnesium or manganese, salts, nicotinamide adenine dinuclease (NAD) and deoxynucleoside triphosphates (dNTPs), such as deoxyadenosine triphosphate, deoxyguanosine triphosphate, deoxycytidine triphosphate and thymidine triphosphate.

A kit may also include instructions for employing the kit components as well the use of any other reagent not included in the kit. Instructions may include variations that can be implemented.

EXAMPLES

Embodiments of the present invention are further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims. The disclosure of each reference set forth herein is incorporated herein by reference in its entirety.

General Procedures and Methods

Botanical Samples

Twenty-four botanical samples that covered all major plant parts and processing stages were collected for DNA profiling. Among these twenty-four samples, powders and extracts were considered as finished materials in the manufacturing process. When available, extracts from different lots were included to minimize DNA profile fluctuation within the same manufacturing process. All samples are listed in Table 5 with their scientific names, types, sample codes, plant parts, and excipient information. Additional chamomile extracts and tea extracts from different lots were collected to study the effect of isolation solvent composition and filtration processes on DNA in botanical extracts, as shown in Table 6. All samples were collected from the Herbalife manufacture line.

TABLE 5

Summary of botanical samples used in genomic DNA profiling.

| common name | scientific name | type | sample code* | plant part | excipient |
|---|---|---|---|---|---|
| ginger | Zingiber officinale | dried raw material | ZO1 | rhizome | N/A |
| | Zingiber officinale | powder | ZO2 | rhizome | N/A |
| | Zingiber officinale | extract | ZO3, ZO4, ZO5 | rhizome | maltodextrin |
| chamomile | Matricaria chamomilla | dried raw material | MC1 | flower heads | N/A |
| | Matricaria chamomilla | powder | MC2 | flower heads | N/A |
| | Matricaria chamomilla | extract | MC3, MC4, MC5 | flower heads | maltodextrin |
| guarana | Paullinia cupana | dried raw material | PCu1 | seeds | N/A |
| | Paullinia cupana | powder | PCu2 | seeds | N/A |
| | Paullinia cupana | extract | PCu3, PCu4, PCu5 | seeds | maltodextrin |
| parsley | Petroselinum crispum | dried raw material | PCr1 | leaves | N/A |
| | Petroselinum crispum | powder | PCr2 | leaves | N/A |

TABLE 5-continued

Summary of botanical samples used in genomic DNA profiling.

| common name | scientific name | type | sample code* | plant part | excipient |
|---|---|---|---|---|---|
| | Petroselinum crispum | extract | PCr3, PCr4, PCr5 | leaves | maltodextrin |
| schisandra | Schisandra chinensis | dried raw material | SC1 | fruits and seeds | N/A |
| | Schisandra chinensis | extract | SC2, SC3, SC4 | fruits and seeds | maltodextrin |

*For one type of botanical product, multiple sample codes are used for samples from different lots

TABLE 6

Summary of botanical extract samples used to study the effects of solvent and filtration process on DNA.

| description | scientific name | plant part | carrier | factors to study | variable | extract ratio | no. of lots |
|---|---|---|---|---|---|---|---|
| chamomile flower powdered extract | Matricaria chamomilla | flower heads | maltodextrin | isolation method | water 100% | 4:1 | 1 |
| | | flower heads | maltodextrin | | water 90-80%/ethanol 10-20% | 4:1 | 1 |
| | | flower heads | maltodextrin | | water 50%/ethanol 50% | 5:1 | 1 |
| | | flower heads | maltodextrin | | water 20%/ethanol 80% | 5:1 | 1 |
| green tea extract | Camellia sinensis | leaves | N/A | filtration | unfiltered | 3-5:1 | 6 |
| | | leaves | N/A | | filtered | 3-5:1 | 6 |
| black tea extract | | leaves | maltodextrin | | unfiltered | 5:1 | 7 |
| | | leaves | maltodextrin | | filtered | 5:1 | 2 |

GeneRuler 50 bp DNA Ladder (Thermo Fisher Scientific, Waltham, MA, USA) was used to provide fragments with various lengths to test the range of adapter ligated DNA fragments that can be amplified.

Maltodextrin samples (M100, M150, M180, M500, M580, M585, and M600) were purchased from Grain Processing Corporation (Lawrenceville, GA, USA).

DNA Isolation

The botanical reference materials were ground into fine powders using 1600 MiniG (SPEX® SamplePrep, Metuchen, NJ, USA) at a frequency of 1500 RPM for 1 minute. Genomic DNA was isolated using DNeasy mericon Food Kit (Qiagen, Germantown, MD, USA) according to the manufacturer's instructions. Input of dietary supplements for DNA isolation was 50 mg for dried raw materials and botanical powders and 400 mg for botanical extracts.

Genomic DNA Characterization

Concentration: The isolated genomic DNA was quantified with a Qubit 3.0 Fluorometer and Qubit® dsDNA HS assay kit (Thermo Fisher Scientific, Waltham, MA, USA) according to the manufacturer's protocol.

UV absorbance ratio (A260/A280): UV absorbance ratio (A260/A280) was measured using spectrophotometer Nano-Drop ND 8000 (Thermo Fisher Scientific, Waltham, MA, USA).

Size detection: The size of the isolated genomic DNA was detected on the 4200 TapeStation instrument with Genomic DNA ScreenTape and reagents (Agilent, Santa Clara, CA, USA). The size of amplified DNA was detected on the 4200 TapeStation instrument with HS (High Sensitivity) D1000 Tape and reagents (Agilent, Santa Clara, CA, USA).

Example 1

Assessment of Botanical Genomic DNA Present in Processed Botanical Materials

The following example demonstrates a method for detecting botanical genomic DNA present in low concentrations by adapter ligation and PCR amplification.

End repair reagents, adapter, and ligation reagents from KAPA Hyper Prep Kit (Kapa Biosystems, Wilmington, MA, USA) were used in the end repair and adapter ligation step. Briefly, input DNA at various amounts was used as input fragmented DNA according to the manufacturer's instructions. To achieve higher ligation efficacy, ligation was performed at 4° C. overnight with adapter concentration adjusted to 300 nM. After DNA fragments ligated to adapters with a known DNA sequence, the adapter-ligated DNA was purified with Agencourt AMPure XP beads (0.8×) (Beckman Coulter, Indianapolis, IN, USA) and eluted with 25 μL of water. The PCR amplification was carried out in a 25 μL reaction mixture containing 12.5 μL of 2× AmpliTaq Gold® 360 Master Mix (Applied Biosystems, Waltham, MA, USA), 10 μL of adapter-ligated DNA, 1.25 μL each of forward and reverse primers (0.5 mM) (forward primer (P5): 5'-AATGATACGGCGACCACCGA-3' (SEQ ID NO: 9) and reverse primer (P7): 5'-CAAGCAGAAGACGGCAT-ACGA-3' (SEQ ID NO: 10)). The PCR reaction was performed in a Bio-Rad C-1000 Touch Thermal Cycler (Bio-Rad, Hercules, CA, USA). The optimized amplification protocol included 1 cycle of 5 minutes at 95° C., followed by 12 cycles of 30 seconds at 95° C., 30 seconds at 58° C., 2 minutes at 72° C., and a final extension step at 72° C. for 5 minutes. The resulted PCR products were purified with Agencourt AMPure XP beads (1.0×) and eluted with 25 µL of water before detection.

To define the range of amplifiable adapter-ligated DNA fragment lengths, log-diluted GeneRuler 50 bp DNA ladder was used as input DNA at 1 ng, 100 pg, 10 pg, 1 pg, 100 fg, 10 fg, and 1 fg. For DNA isolated from maltodextrin and botanical samples, 10 µL of crude eluted DNA was used as input DNA for KAPA Hyper Prep Kit before detection. Experiment conditions were as described above.

Welch two sample t-test (two-sided) was performed to analyze the changes in DNA concentration between unfiltered and filtered tea extracts.

Genomic DNA of five botanical species, derived from botanical materials of different process types, was isolated by Qiagen DNeasy mericon Food Kit. The concentrations and absorbance ratios (A260/A280) of the eluted DNA were determined by fluorometer and spectrophotometric analysis respectively (Table 7). The dried raw materials yielded the highest DNA concentration among all types of materials in the same species. DNA concentrations from most sterilized botanical powders and extracts were usually 10 times lower than DNA concentrations from dried raw materials (except chamomile flower powder), with some of them even falling below the concentration range that the fluorometer can accurately measure (concentration labeled as too low). The ratio of absorbance at A260/A280 is generally used to measure the purity of DNA samples, with values between 1.7 and 1.9 indicating pure DNA. The absorbance ratios were usually acceptable when the DNA concentrations were above 1 ng/µL (FIG. 1, left panel). However, its measurement became inaccurate when the DNA concentrations were low, as illustrated by a half-log dilution of chamomile gDNA standards of good purity (FIG. 1, right panel).

Figure 2:
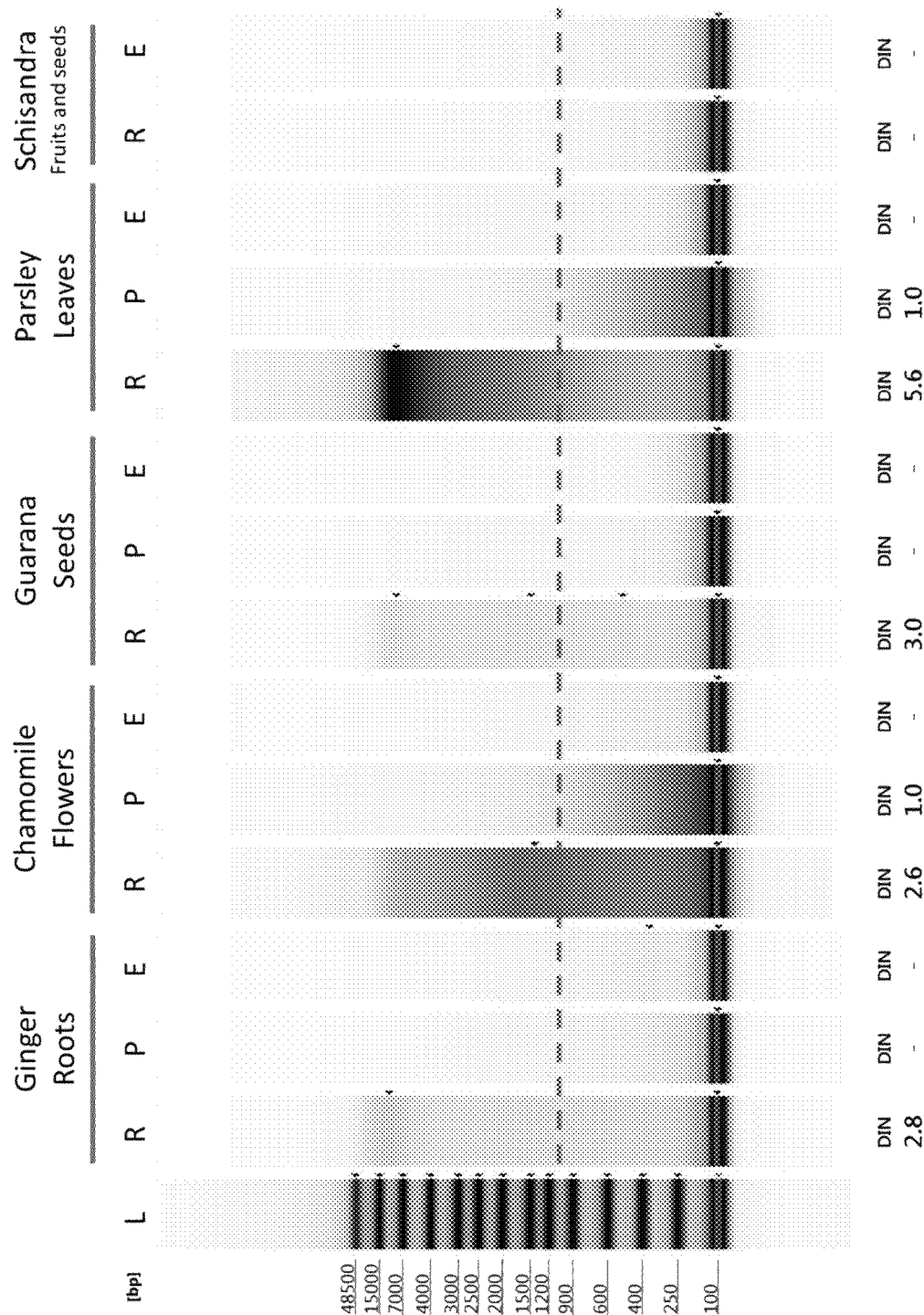
FIG. 2 depicts DNA in dried raw materials and processed herbal products. R: raw material; P: sterilized powder; E: extract; L: ladder. DNA integrity numbers (DINs) are listed below each sample where evaluated. The 100-bp marker in the genomic reagent buffer is indicated in each lane. Dashed horizontal line marks the DNA fragment size at 1000 bp.

The integrity of isolated genomic DNA from various herbal products was compared by TapeStation with genomic DNA tape (FIG. 2). The genomic DNA isolated from most dried raw botanical materials (except *Schisandra*) were observed to appear as a smear, which is an indicator of DNA degradation. Even though the DNA integrity was suboptimal, a significant portion of genomic DNA still had fragment sizes greater than 7000-bp. Genomic DNA isolated from sterilized powders appeared as either a smear or background signal that was outside the detection range of TapeStation. However, in contrast to the DNA smears observed in the dried raw botanical materials, visible DNA smears displayed by sterilized powders were all fragmented to small sizes. For example, as determined by the TapeStation analysis software, 76% of the DNA in chamomile powder and 86% of DNA in parsley powder was below 1000-bp, while the percentage of DNA below 600-bp was 60% and 74%, respectively. None of the genomic DNA isolated from botanical extracts was able to be detected by TapeStation due to low DNA input.

DNA integrity numbers (DINs) estimated by TapeStation analysis software showed genomic DNA isolated from dried botanical materials have the highest value, followed by DNA from sterilized powders. No DINs were estimated for DNA from botanical extracts since their signals were below the quantitative threshold required to trigger the DIN estimation by TapeStation analysis software.

Figure 3A:
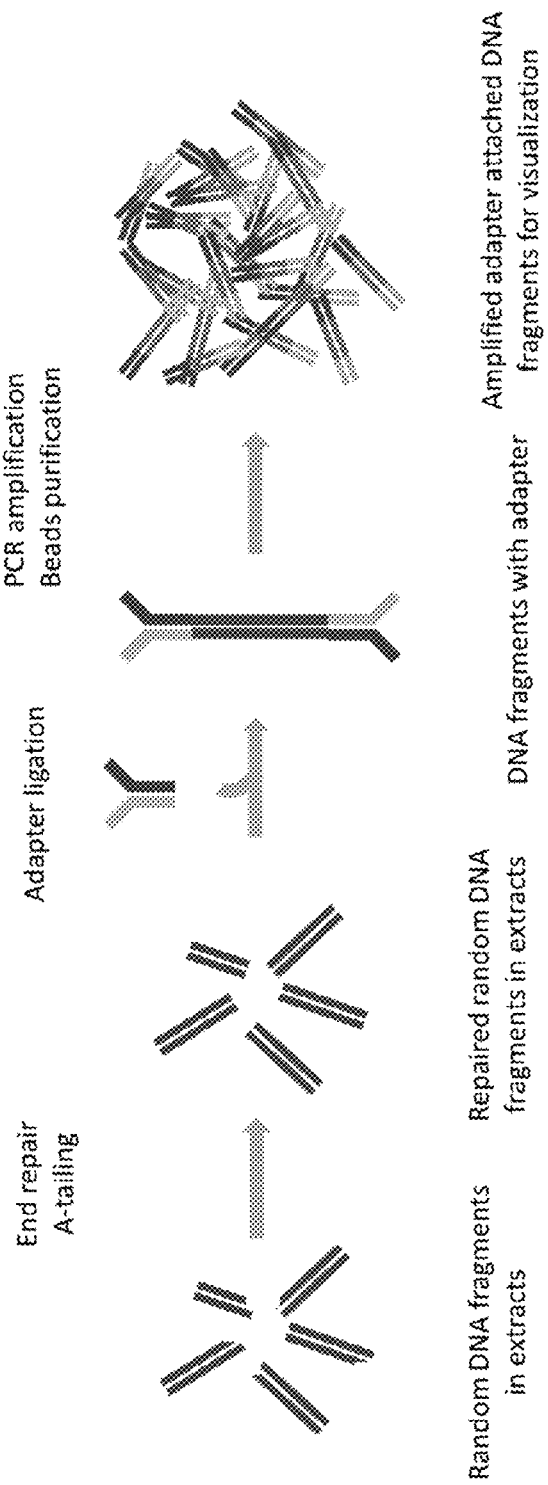
FIG. 3A illustrates a workflow for amplifying DNA fragments with adapter ligation and PCR amplification. Double-stranded DNA fragments from botanical dietary supplements are first end-repaired and A-tailed, and adapters are then ligated to these random fragments followed by 12 cycles of PCR amplification for detection.
Figure 3B:
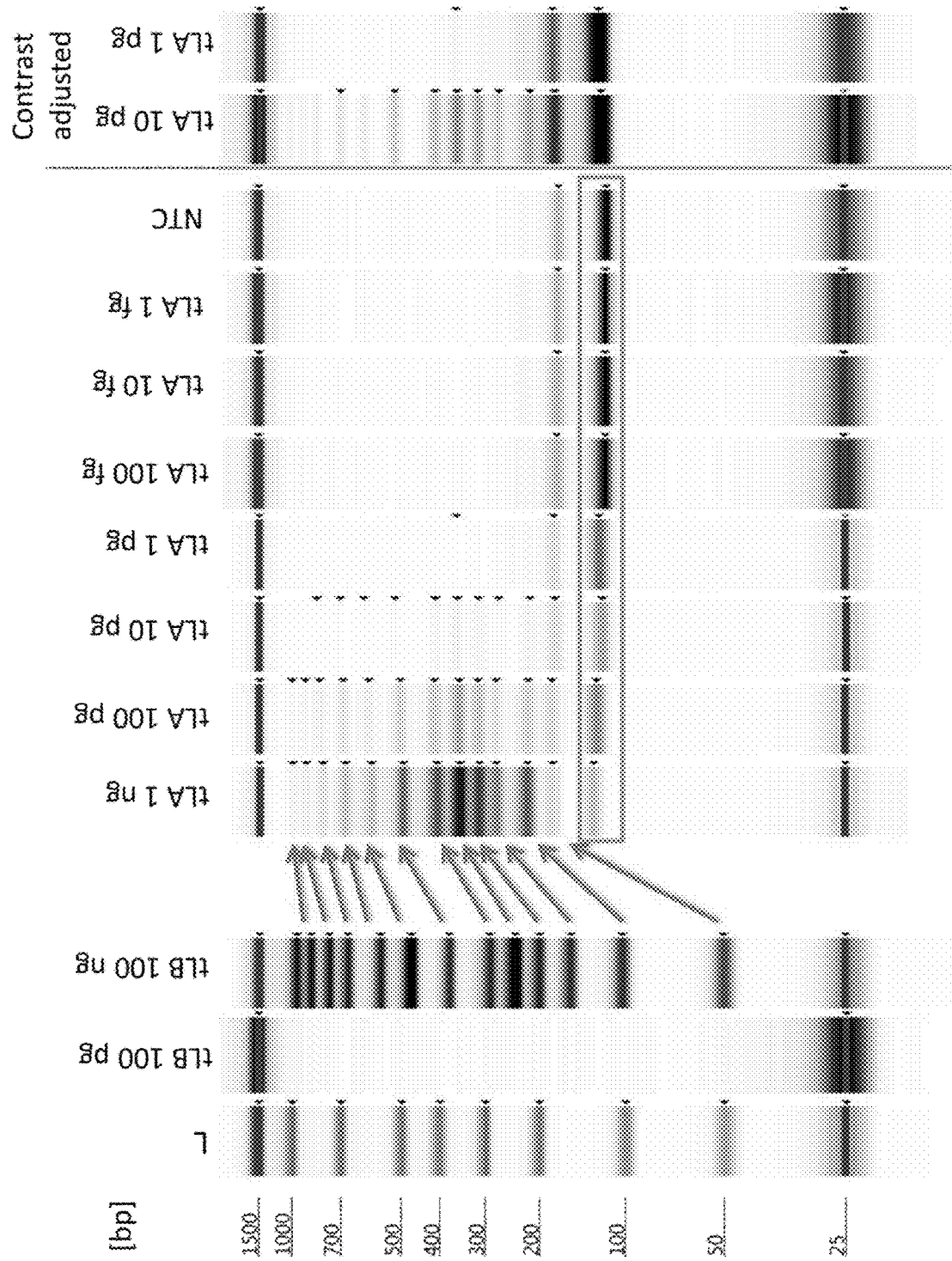
FIG. 3B depicts adapter ligation and PCR amplification of DNA ladder at various concentrations to demonstrate the limit of detection (LOD) of the methods described herein. L: ladder provided by TapeStation HS D1000 reagent; tLB: original GeneRuler 50-bp DNA ladder; tLA: GeneRuler 50-bp DNA ladder after adapter ligation and 12 cycles of PCR amplification. The arrows connect the ladder fragments before and after the KAPA Hyper Prep Kit process. The black triangles are peaks automatically detected by the TapeStation analysis software. Horizontal lines in each lane denote the lower (25-bp) and upper (1500-bp) marker in TapeStation HS D1000 reagent buffer. The two right-most lanes are lanes "tLA 10 pg" and "tLA 1 pg" after adjustment of image contrast for weak signal detection. Bands in the box are adapter dimers. NTC: non-template control.

Based on the observation that all visible genomic DNA isolated from processed materials was fragmented to a length below 1000-bp, the reagent provided by KAPA Hyper Prep Kit was applied to amplify the low amount of DNA fragments (FIGS. 3A and 3B). To ensure that the method can successfully amplify DNA fragments up to 1000-bp, a DNA ladder ranging from 50-bp to 1000-bp was tested as a control for the size range of this detection method. In addition, the ladder was used at different input amounts, from 1 ng to 1 fg, to determine the detection limit of this approach. The original input signal was "invisible" by high sensitivity D1000 Tape starting at the 100 pg input group. After 12 PCR cycles, the kit was able to amplify all the major DNA fragments between 50-bp to 900-bp when the amount of input DNA used was at 1 ng, 100 pg and 10 pg, as detected by the same technique (FIG. 3B). When the amount of input DNA decreased to 1 pg, several large fragments became invisible, but the fragments between 50-bp to 250-bp were still amplified and visible. When the amount of input DNA was below 1 pg, the kit was not able to produce identifiable signals from the ladder, except a major band at around 130-bp (adapter-dimer) and a minor band around 185-bp, which were both present in the non-template control. The analysis of the ladder size in base pairs is provided in Table 8.

TABLE 7

DNA concentration and absorbance ratio in botanical samples of various types.

| sample code | concentration (ng/µL) | absorbance ratio | type |
|---|---|---|---|
| ZO1 | 4.58 | 1.93 | raw |
| ZO2 | 0.419 | 1.81 | powder |
| ZO3 | 0.206 | 1.54 | extract |
| ZO4 | 0.505 | 1.94 | extract |
| ZO5 | 0.396 | 2.31 | extract |
| MC1 | 19.8 | 1.75 | raw |
| MC2 | 10.5 | 1.82 | powder |
| MC3 | 0.199 | 1.19 | extract |
| MC4 | 0.202 | 1.23 | extract |
| MC5 | 0.232 | 1.26 | extract |
| PCu1 | 3.09 | 1.82 | raw |
| PCu2 | 0.193 | 1.48 | powder |
| PCu3 | 0.076 | 1.68 | extract |
| PCu4 | too low | 1.89 | extract |
| PCu5 | 0.054 | 1.46 | extract |
| PCr1 | 38.7 | 1.84 | raw |
| PCr2 | 0.256 | 1.51 | powder |
| PCr3 | too low | 1.86 | extract |
| PCr4 | 0.072 | 1.83 | extract |
| PCr5 | 0.07 | 1.56 | extract |
| SC1 | 0.052 | 1.48 | raw |
| SC2 | too low | 1.08 | extract |
| SC3 | too low | 0.76 | extract |
| SC4 | 0.109 | 0.78 | extract |

TABLE 8

Analysis of Ladder Size (in base pairs).

| fragment size before amplification | | fragment size after amplification | |
|---|---|---|---|
| | | | size with adapter-dimer |
| theoretical size | measured size | measured size | length subtracted |
| 50 | 50 | 191 | 48 |
| 100 | 104 | 231 | 88 |
| 150 | 164 | 288 | 145 |
| 200 | 201 | 322 | 179 |
| 250 | 245 | 367 | 224 |

TABLE 8-continued

Analysis of Ladder Size (in base pairs).

| fragment size before amplification | | fragment size after amplification | |
|---|---|---|---|
| theoretical size | measured size | measured size | size with adapter-dimer length subtracted |
| 300 | 292 | 422 | 279 |
| 400 | 381 | 513 | 370 |
| 500 | 476 | 615 | 472 |
| 600 | 573 | 697 | 554 |
| 700 | 679 | 835 | 692 |
| 800 | 778 | 938 | 795 |
| 900 | 890 | 1039 | 896 |
| 1000 | 976 | NA | NA |

Figure 4:
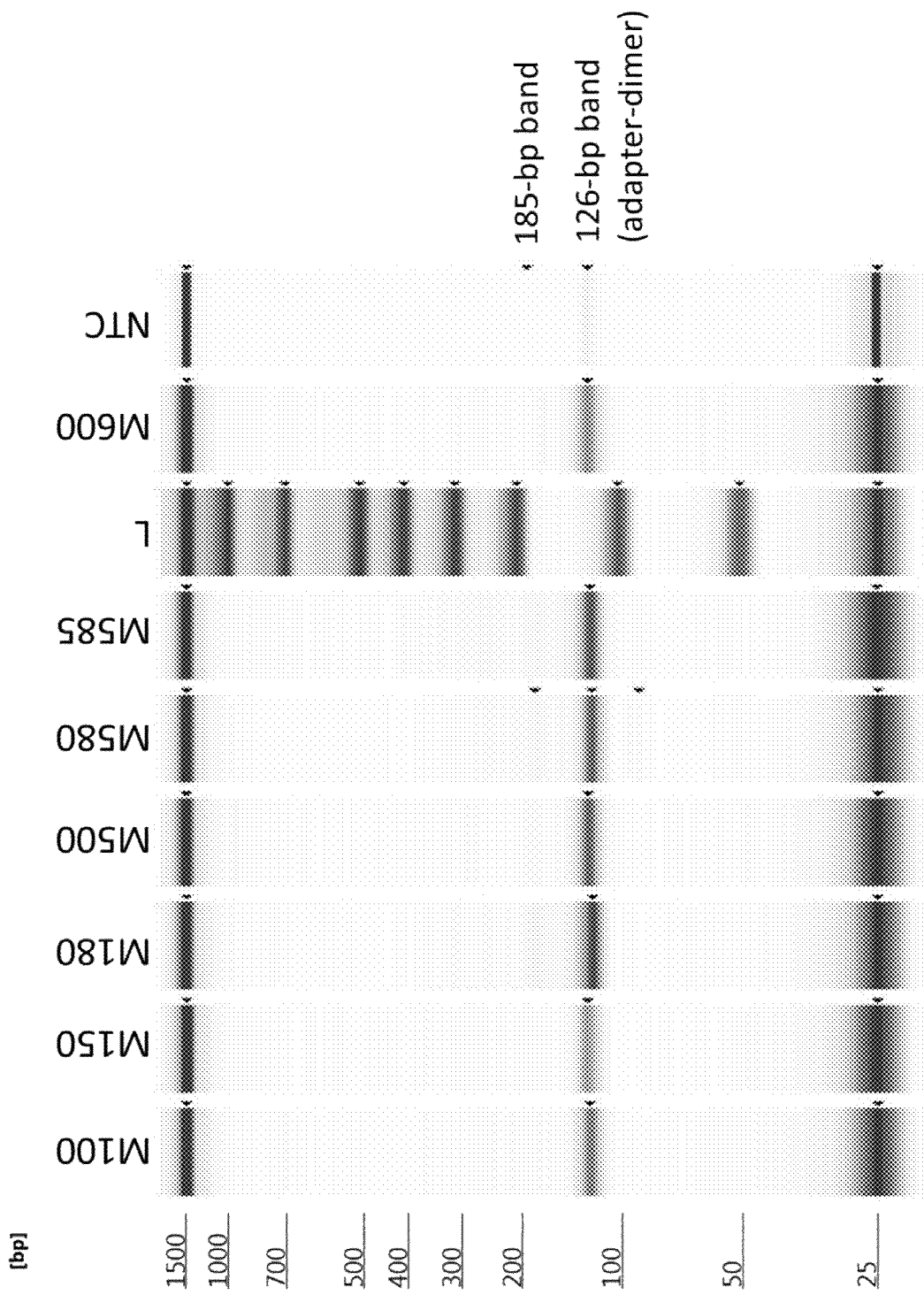
FIG. 4 depicts a gel image of DNA from various maltodextrin samples after adapter ligation and PCR amplification. L: ladder provided by TapeStation HS D1000 reagent; NTC: non-template control. Horizontal lines in each lane denote the lower (25-bp) and upper (1500-bp) marker in the TapeStation HS D1000 reagent buffer.

Given that most of the botanical extracts used in this study contain corn starch-derived maltodextrin, the amount of DNA contributed by maltodextrin was evaluated to provide a baseline DNA signal. DNA was isolated from seven types of commonly used maltodextrin and its concentration and size range was measured by fluorometer and TapeStation, respectively. The results indicated that DNA isolated from maltodextrin had concentration below the detection range of fluorometer most of the time, and when the concentrations were measurable, the readings were at the low end of the fluorometer detection range (Table 9). No types of maltodextrin consistently produced DNA isolations with measurable concentration. After 12 cycles of PCR amplification of the adapter-ligated DNA, none of the DNA isolations exhibited a visible smear on TapeStation HS D1000 tape, except a major adapter dimer band and an occasional 185-bp minor band. Both of these bands also showed up in the non-template control (NTC) (FIG. 4). The amount of DNA contributed by maltodextrin was negligible under current test conditions.

TABLE 9

DNA concentration of DNA isolated from maltodextrin.

| | concentration (ng/μL) | | |
|---|---|---|---|
| maltodextrin sample | isolation 1 | isolation 2 | isolation 3 |
| M100 | too low | too low | 0.053 |
| M150 | 0.062 | too low | too low |
| M180 | too low | too low | too low |
| M500 | too low | 0.061 | too low |
| M580 | too low | 0.067 | too low |
| M585 | 0.055 | too low | too low |
| M600 | too low | too low | too low |

Figure 5:
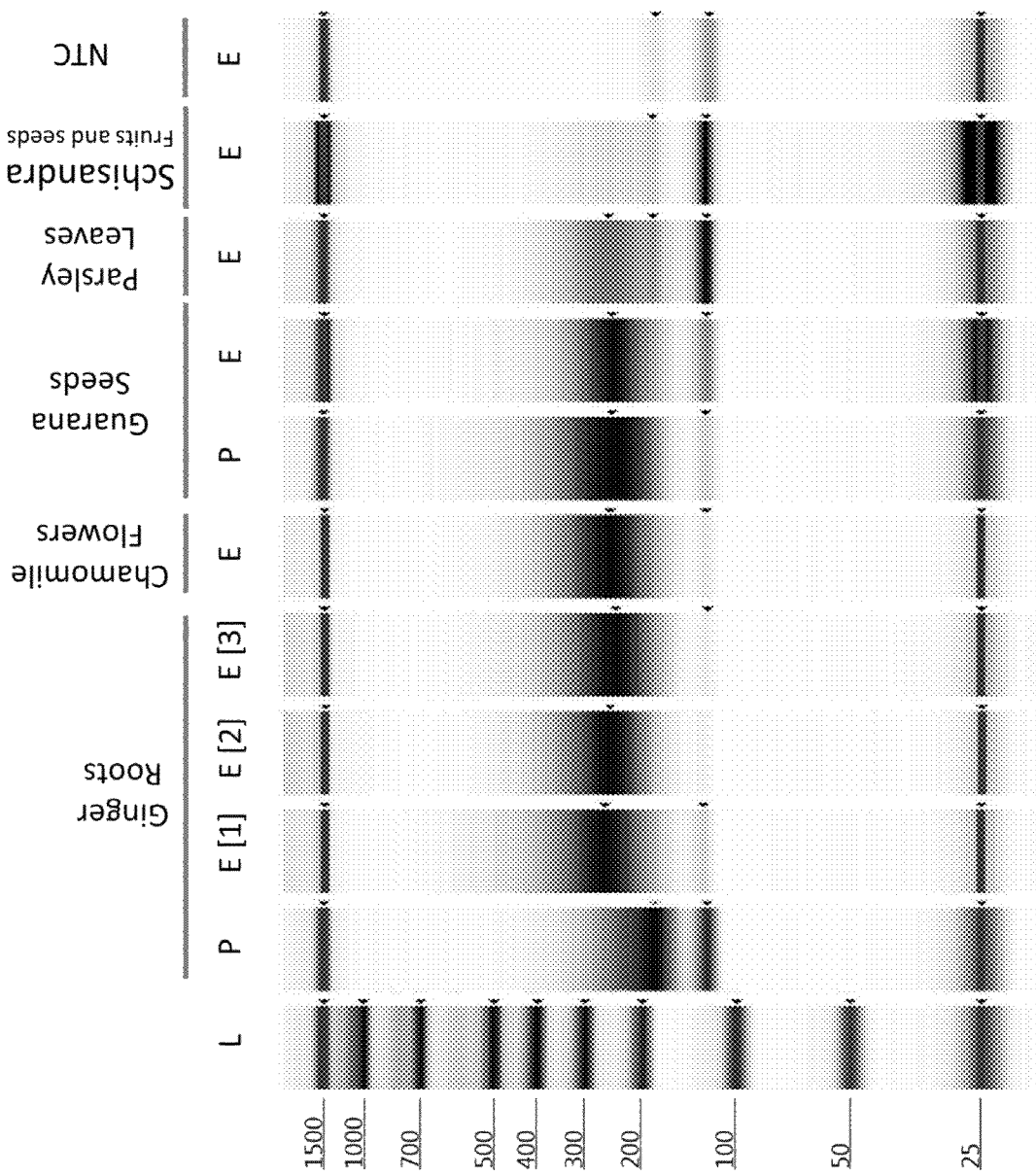
FIG. 5 depicts a gel image of DNA from botanical powders and extracts after adapter ligation and PCR amplification. L: ladder provided by TapeStation HS D1000 reagent; NTC: non-template control. Horizontal lines in each lane denote the lower (25-bp) and upper (1500-bp) marker in TapeStation HS D1000 reagent buffer.

To detected fragmented DNA in botanical powders and extracts, DNA isolations that were below the detection limit of TapeStation genomic tape were ligated by adapter followed by 12 cycles of PCR amplification. DNA smears were observed in all processed botanical powders and extractions. The size distribution of these smears ranged from 150-bp to 350-bp (FIG. 5). Taking into account the length of the adapter on both ends (approximately 130-bp in total), the actual fragment length of DNA in these processed materials ranged from 20-bp to 220-bp. DNA size distribution was found to be specific to the materials' manufacturing process. The same botanical manufactured by different processes showed different size distribution; however the distribution did not vary between different lots manufactured by the same process (FIG. 5, ginger roots E[1], E[2], and E[3]).

In addition to some common process steps, such as grinding and extensive heat treatment, specific manufacturing processes have been applied to certain botanicals to achieve the highest enrichment of bioactive ingredients and to meet regulatory requirements.

Figure 6A:
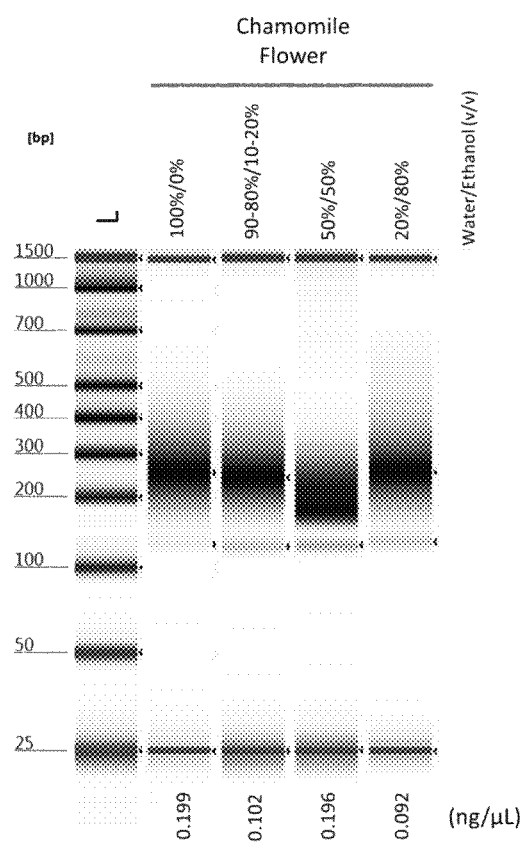
FIG. 6A and FIG. 6B depict gel images of DNA from botanical extracts after adapter ligation and PCR amplification. L: ladder provided by TapeStation HS D1000 reagent. Horizontal lines in each lane denote the lower (25-bp) and upper (1500-bp) marker in TapeStation HS D1000 reagent buffer.

For botanical extracts, water and ethanol are the two most frequently used solvents in DNA isolation. To study the effect of different solvents on the DNA retained in botanical extracts, DNA in chamomile extracts, which were made using different isolation solvent ratios, was detected by adapter ligation and PCR amplification. Both aqueous and hydro-alcoholic isolation methods yielded DNA that can be easily seen by TapeStation after amplification (FIG. 6A). The concentrations of DNA in chamomile extracts were determined by fluorometer; however statistical analysis was not performed because only a single lot is available for each chamomile extract type. Based on the distribution of TapeStation smears and measurable DNA concentrations in all tested extracts, the presence of DNA in botanical extract was independent of the isolation solvent, such as water and ethanol.

Figure 6B:
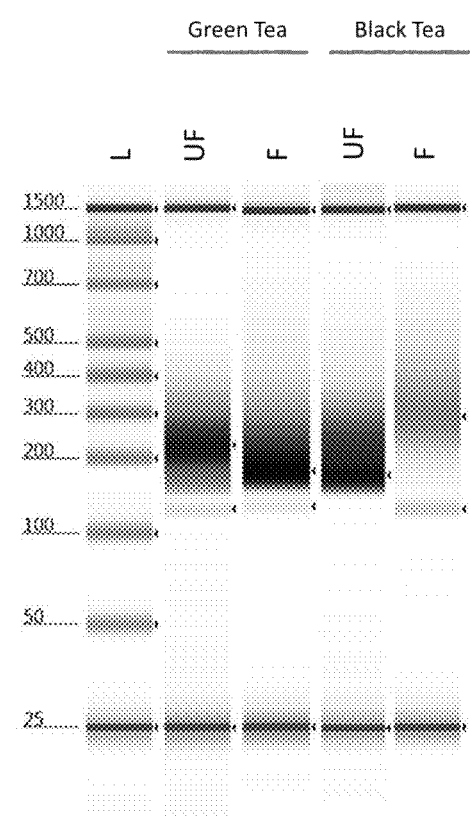
Figure 6C:
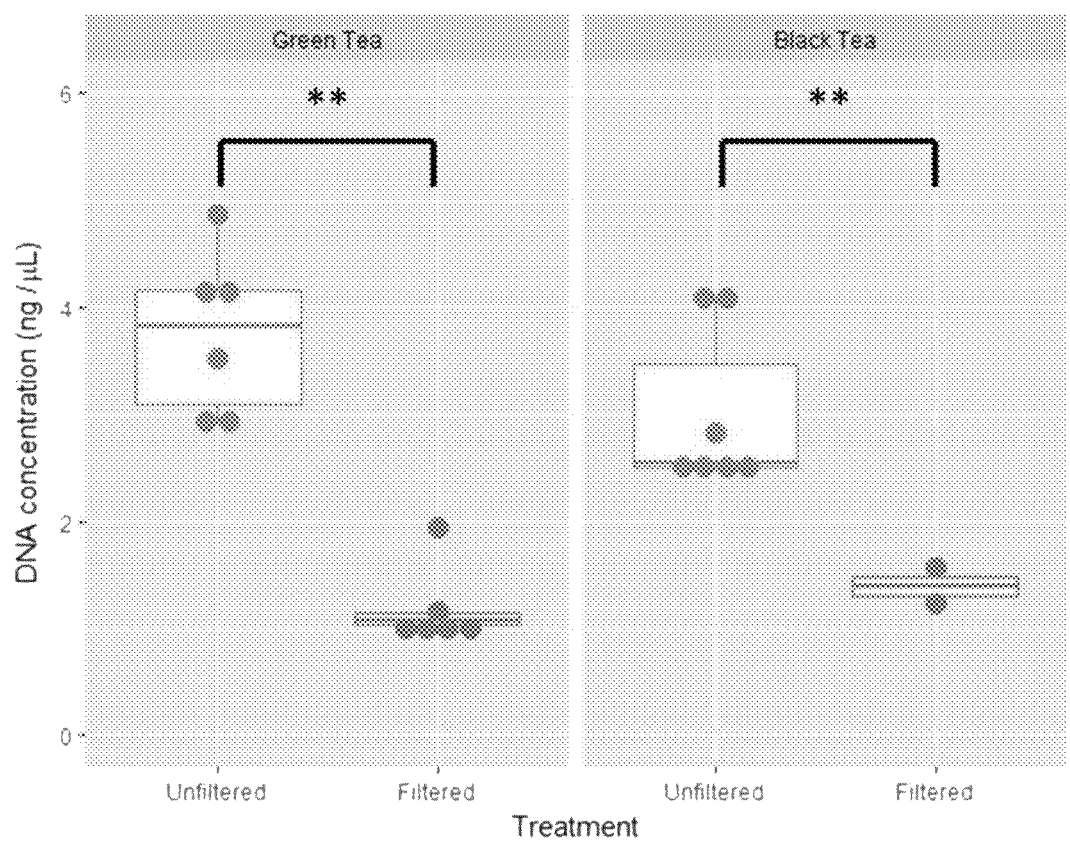
FIG. 6C shows the change in the DNA concentration with filtration in tea extracts (left: green tea; right: black tea). ** indicates a significant difference ($p<0.01$).

Filtration is often used to separate particles from a solution after the solvent isolation procedure. To compare the effects of filtration on the DNA retained in botanical extracts, the size and concentration of DNA from unfiltered and filtered tea extracts were determined. DNA was present in tea extracts regardless of filtration process (FIG. 6B). However, based on the measurements of DNA isolated from different lots of tea extracts, DNA concentration in filtered tea extracts was lower than DNA concentration in unfiltered tea extracts ($p<0.01$). FIG. 6C shows the change in DNA concentration of green tea and black tea with filtered or unfiltered samples.

Example 2

Characterization and Authentication of Chamomile DNA Fragments from Dietary Supplements by Targeted PCR The following example demonstrates a method for authenticating botanical DNA fragments from a chamomile dietary supplement.

Botanical reference materials (BRMs) were purchased from ChromaDex or AHP. Two-tiered barcodes, rbcL and ITS2, were amplified with universal primers and Sanger sequenced to confirm the molecular identity of these commercial BRMs (data not shown). Six German chamomile herbal supplements (three powders and three extracts), two feverfew extracts, and two Chinese chamomile extracts from different manufacturers were purchased online.

The botanical reference materials were ground into fine powders using 1600 MiniG (SPEX® SamplePrep, Metuchen, NJ, USA) at a frequency of 1500 RPM for 1 minute. Then genomic DNA was isolated using a DNeasy Plant Mini Kit (Qiagen, Germantown, MD, USA), according to the manufacturer's instructions. Dietary supplements in the form of powder and extract were isolated using a DNeasy mericon Food Kit (Qiagen, Germantown, MD, USA), according to the manufacturer's instructions. Input dietary supplements for DNA isolation was 50 mg for botanical powders and 400 mg for botanical extracts.

Concentration: The isolated genomic DNA was quantified with a Qubit 3.0 Fluorometer and Qubit® dsDNA HS assay kit (Thermo Fisher Scientific, Waltham, MA, USA) according to the manufacturer's protocol.

Size: The size of the isolated genomic DNA was detected on 4200 TapeStation instrument with Genomic DNA ScreenTape and reagents (Agilent, Santa Clara, CA, USA). For the isolated DNA beyond the detection limit of 4200 TapeStation, further amplification of the genomic DNA was performed by KAPA hyper prep kit (Kapa Biosystems, Wilmington, MA, USA) before detection. Briefly, 10 μL of the isolated genomic DNA went through the library construction protocol as input fragmented DNA according to the manufacturer's instructions. After ligated to adapters with known DNA sequence (adapter concentration adjusted to 300 nM for low-input DNA), input DNA was amplified with primer mix provided in the Kit. The reaction performed in a Bio-Rad C-1000 Touch Thermal Cycler (Bio-Rad) using a modified amplification protocol consisted of 1 cycle of 2 minutes at 98° C., followed by 15 cycles of 30 seconds at 98° C., 30 seconds at 58° C., 60 seconds at 72° C., and a final extension step at 72° C. for 3 minutes. The resulted PCR products were beads-purified (0.8×) and detected again on 4200 TapeStation instrument with High Sensitivity D1000 Tape and reagents (Agilent, Santa Clara, CA, USA).

ITS2 barcode region was selected in this study, because it not only capable of discriminating plant taxa from different plant families, but is also able to distinguish closely related taxa at the genus and species levels (Chen, et al. (2010). Validation of the ITS2 region as a novel DNA barcode for identifying medicinal plant species. PLoS One, 5(1), e8613, incorporated herein by reference in its entirety). Multiple ITS2 sequences of species in the test scope were downloaded from Genbank. *Matricaria chamomilla*: KX167615, EU179212, KC816562; *Tanacetum parthenium:* EF577320, KU724224, KR150179; *Chamaemelum nobile:* EU179215; *Chrysanthemum x morifolium:* AB064276, KC215400, FJ980331, EF091597; *Chrysanthemum indicum:* JF421484, KJ183125, KC215403. To avoid potential artefacts and errors in the uncurated public database, such as Genbank, a serial of bioinformatic curation steps were undertaken on all sequences in the above dataset. To evaluate these barcodes, phylogenetic analysis was performed using the neighbor-joining method with 1000 bootstrap replicates via the Molecular Evolutionary Genetic Analysis (MEGA) software program (version 7). *Matricaria chamomilla* ITS2 barcode KC816562 was removed from downstream analysis, because it did not shared the same node on the tree with other *Matricaria chamomilla* ITS2 sequences.

To incorporate in-species sequence variation in primer design, retained ITS2 sequences were grouped by species and merged to generate species-level consensus sequences in BioEdit (version 7.2.6). Species-specific primers were developed with the program "Primer-BLAST" on the basis of target species consensus sequence as PCR template and non-target consensus sequences as exclusion sequences. The designed primers were checked against the alignment of species-level consensus sequences for each species in the test scope. All primers were synthesized by IDT (Integrated DNA Technologies, Skokie, IL, USA).

Two primer sequences in the same strand were concatenated into one sequence separated by 5 Ns and BLAST searched in the GenBank database. The search was specified by the following parameters. Database: Nucleotide Collection (nr/nt); Program Selection: Somewhat similar sequences (blastn) program; Algorithm parameters: word size (7), expect threshold (1000), the low complexity filter (off). Returned entries were filtered to select entries with query cover percentage match the percentage of combined forward and reverse primers in query.

The PCR amplification was carried out in a 20 μL reaction mixture containing 10 μL of 2× AmpliTaq Gold® 360 Master Mix (Applied Biosystems, Waltham, MA, USA), 3 μL of genomic DNA isolate, 1 μL each of forward and reverse primers (0.5 μM). The PCR reaction was performed in a Bio-Rad C-1000 Touch Thermal Cycler (Bio-Rad, Hercules, CA, USA). The optimized amplification protocol consisted of 1 cycle of 5 minutes at 95° C., followed by 35 cycles of 30 seconds at 95° C., 30 seconds at 61° C., 30 seconds at 72° C., and a final extension step at 72° C. for 2 minutes. DNA isolated from BRMs was diluted 100-fold before subject to PCR amplification. The amplification product was separated in a 2% agarose gel, stained with Gel-Red™ Nucleic Acid Gel Stains (Biotium, Hayward, CA, USA) and detected under UV light. The size of the PCR product was measured using a GeneRuler 50 bp DNA Ladder (Thermo Fisher Scientific, Waltham, MA, USA).

Genomic DNA was prepared from botanical BRMs and serial half-log dilutions were made from 1 ng/μL to 100 ag/μL. PCR product was detected on agarose gel and the limit of detection was determined to be the highest dilution which produced a visible amplicon at expected size across all three independent assays.

Figure 7A:
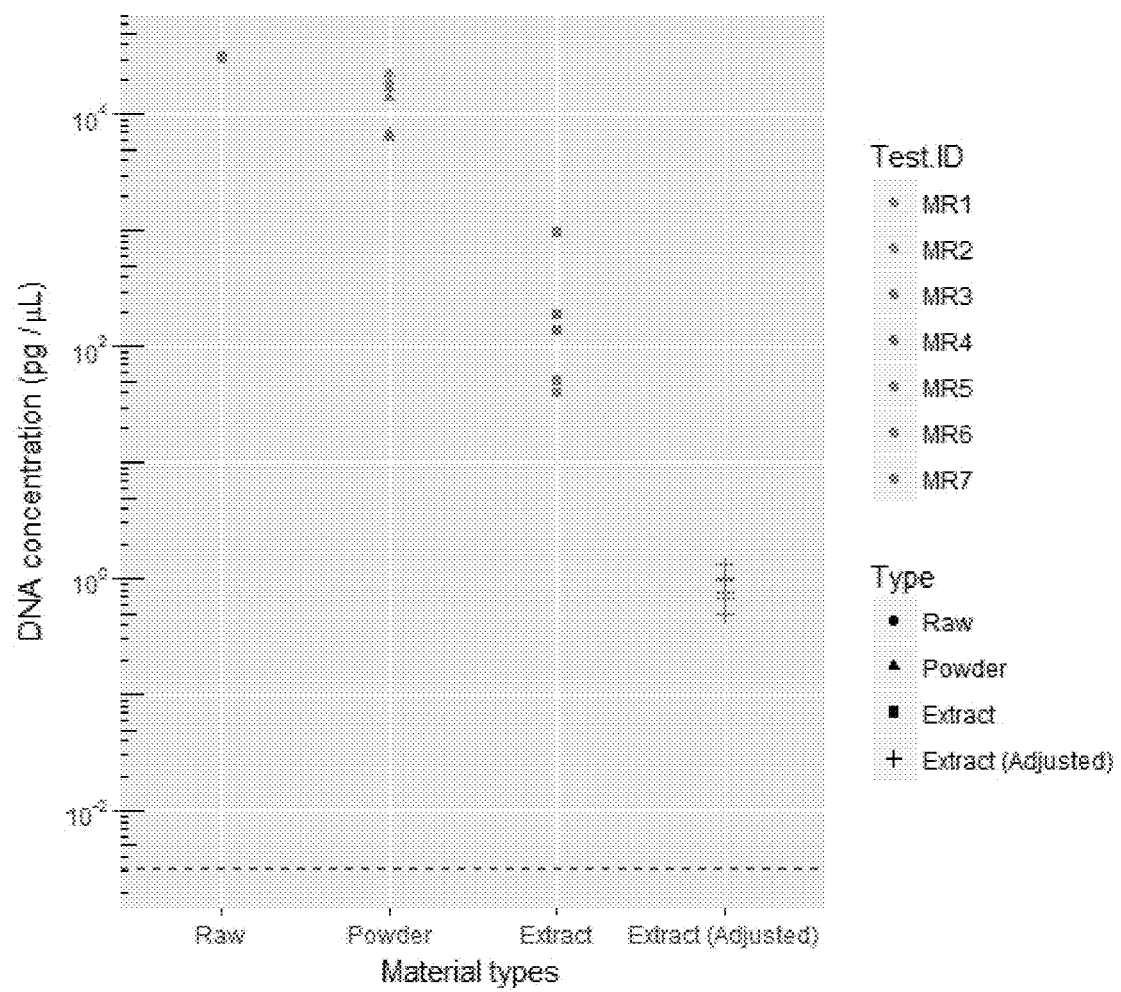
FIG. 7A depicts DNA concentration of various chamomile products obtained from raw material, powder, extract, or adjusted extract, with the concentration of DNA expressed in pg/µL on a logarithmic scale.

The quantity and quality of genomic DNA isolated from finished herbal products is one of the major concerns for the applicability of PCR-based analytical methods. To design DNA-based German chamomile authentication methods that can be applied to most German chamomile dietary supplements, DNA isolated from different forms of herbal products and various manufacturers are characterized. The concentration of double-stranded DNA ranges from 60 ng/μL-5.0 ng/μL in DNA isolated from raw German chamomile, ranges from 30 ng/μL-3.0 ng/μL in DNA isolated from capsulized powders, and ranges from 0.3 ng/μL to 0.01 ng/μL in chamomile extracts (FIG. 7A).

Figure 7B:
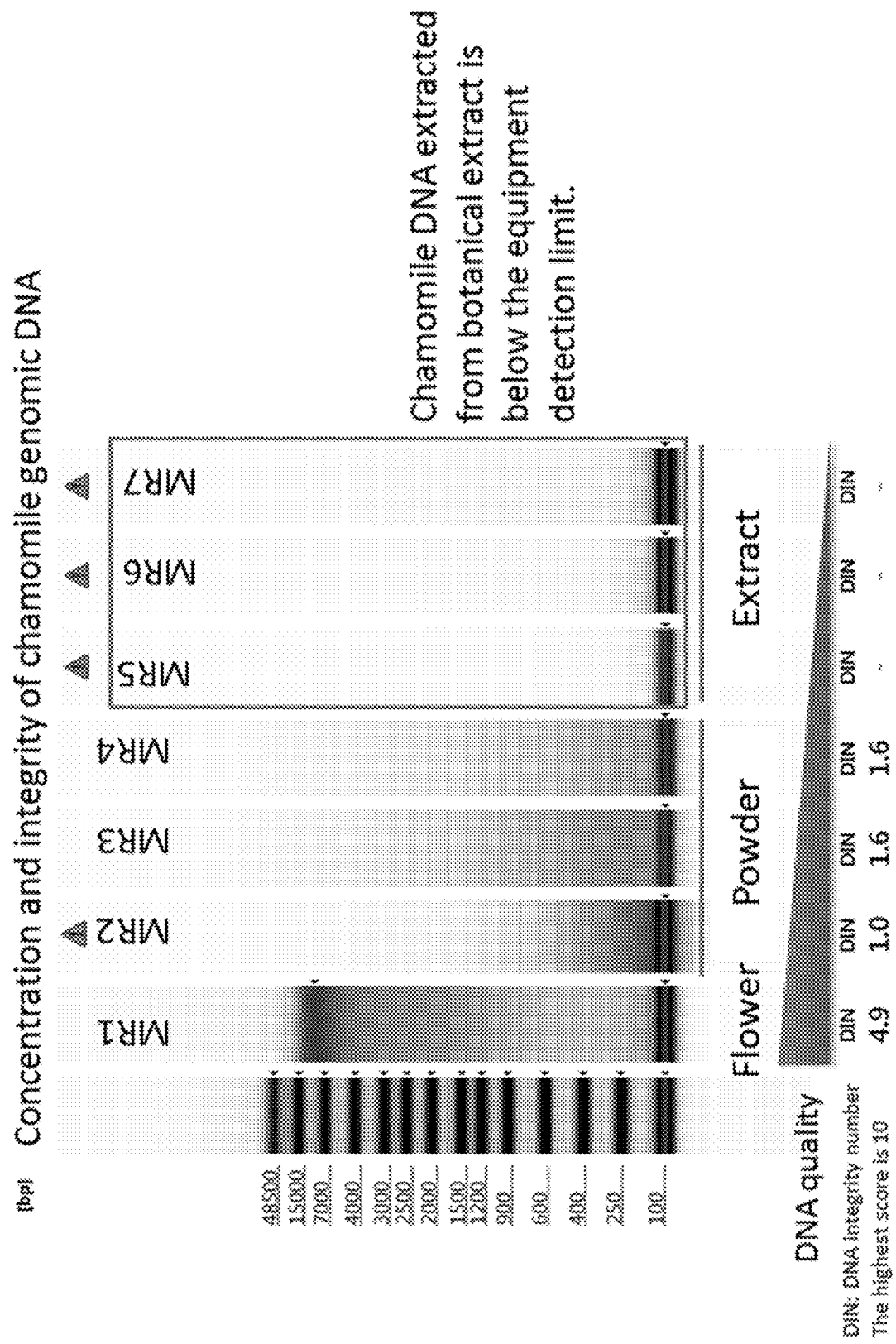
FIG. 7B depicts the fragment size of isolated chamomile genomic DNA from manufacturer samples 1-7 (MR1-MR7), indicating the concentration and integrity of the chamomile genomic DNA. Chamomile DNA fragments isolated from botanical extracts (MR5, MR6, and MR7) are below the detection limit.

Due to the intensive manufacture process, DNA isolated from processed herbal products are always damaged or fragmented to the size range, which cannot be amplified by traditional universal primers that were designed for full-length barcodes. The fragment size of the isolated genomic DNA was evaluated by TapeStation 4200 with genomic DNA tape (FIG. 7B). High quality genomic DNA was observed in BRM DNA isolate, followed by fragmented DNA in powders from 3 different manufactures. Only background signal was detected in DNA isolated from chamomile extracts. DNA integrity number (DIN) assigned by the TapeStation analysis software was consistent with the Gel-like image, with BRM DNA has the highest DIN (4.9), followed by powder-derived DNA DIN ranges from 1.6 to 1.0. The software failed to get the DINs of the extract-derived genomic DNA.

Figure 7C:
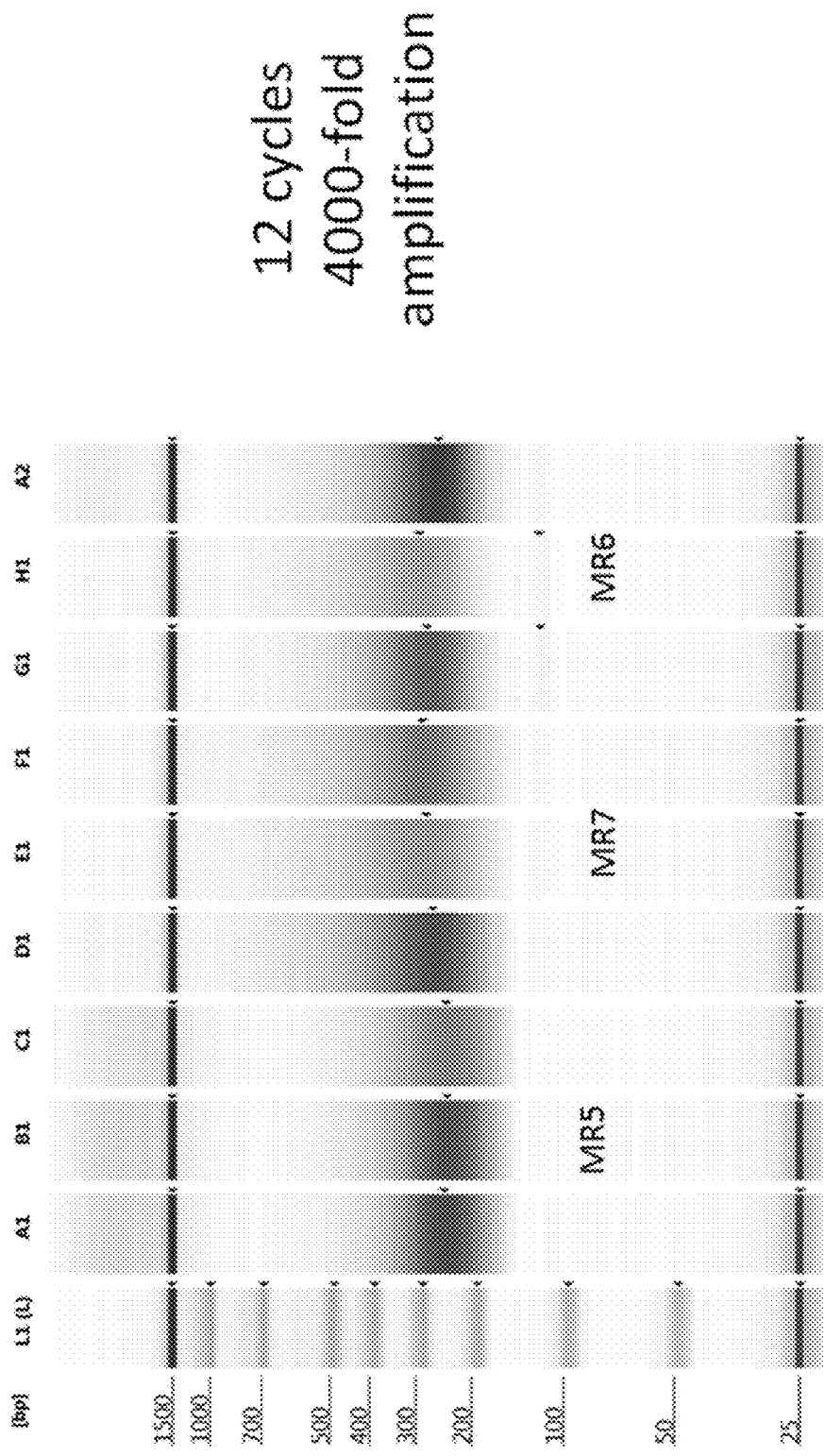
FIG. 7C depicts a gel image of chamomile DNA fragments from chamomile extracts (MR5, MR6, and MR7) following a 12-cycle PCR amplification.

To further detect the size of these extract-derived DNA, DNA fragments were ligated to DNA adaptor with known sequence, and then PCR amplified for 12 cycles. Based on the observation that DNA is heavily degradation in botanical extracts, high-sensitivity tape designed for DNA fragment between 25 bp to 1000 bp was used to evaluate extract-derived DNA after PCR amplification. The majority of the DNA fragments fall into the size range between 180 bp and 400 bp with the length of adaptor on both ends taken into account (FIG. 7C). The actual DNA fragment size is predicted to be 40 bp to 260 bp after subtracting adaptor length on the ends. The above result indicates a significant portion of the isolated DNA has size around 100 bp.

Figures 8A, 8B:
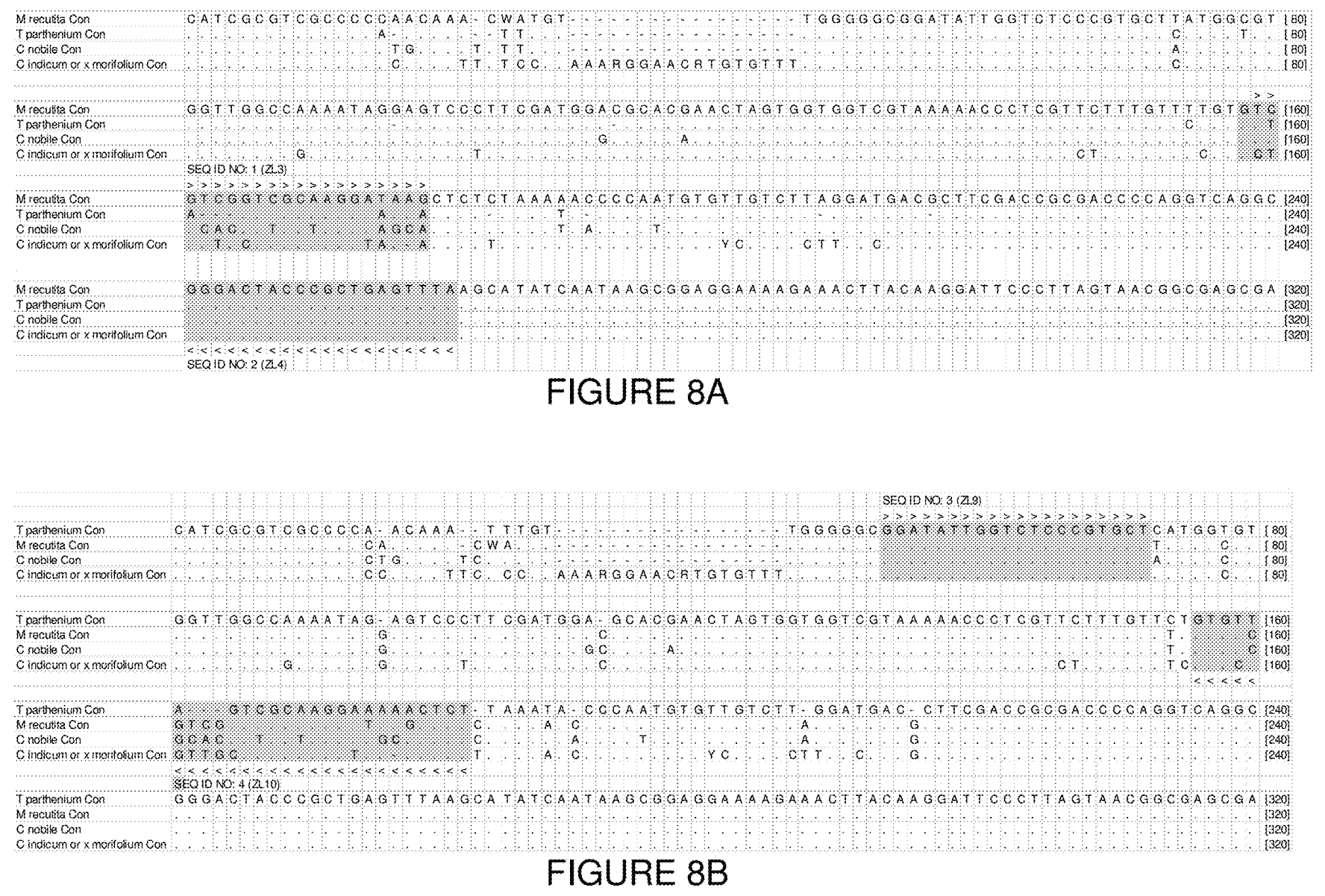
Figures 8C, 8D:
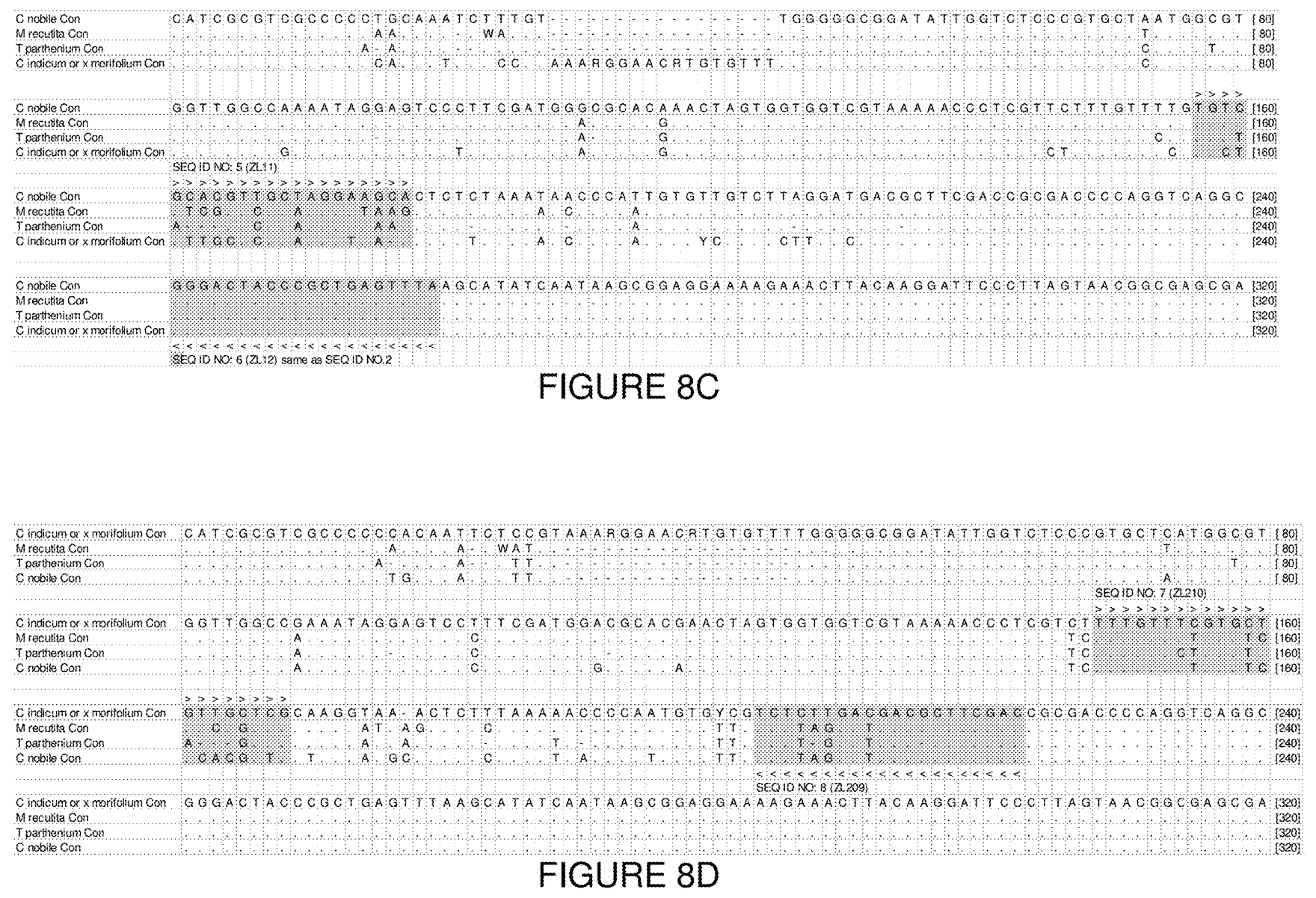

German chamomile authentication test were designed based on the genomic DNA profile isolated from German chamomile dietary supplements (FIGS. 8A-8D) and DNA profile of other botanical dietary supplements in the test scope. The German chamomile authentication test contains four individual tests. 1) German chamomile ID test produce a 103-bp (SEQ ID NOs: 1 and 2) amplicon when German chamomile genomic DNA is present (FIG. 8A). To detect potential botanical contamination, 2) feverfew ID test (FIG. 8B), 3) Roman chamomile ID test (FIG. 8C), and 4) Chinese chamomile ID test (FIG. 8D) produce a 125-bp (SEQ ID NOs: 3 and 4), 104-bp (SEQ ID NOs: 5 and 6), and 73-bp (SEQ ID NOs: 7 and 8) amplicon, respectively, when their target species genomic DNA is present.

In-silico specificity was assessed by searching primer sequence in BLAST program. Candidate target species are the BLAST returned species, whose sequence was covered by both forward and reverse primer sequences. Primers used in German chamomile ID test yield *Matricaria chamomilla* var. *recutita* as the only species. Primers used in feverfew ID test yield multiple species in genus *Tanacetum, Achillea, Tripleurospermum, Anthemis,* and *Oncosiphon*. The candidate species, in genus *Tanacetum,* includes feverfew (*Tanacetum parthenium*) and Tansy (*Tanacetum vulgare*), which sometimes mistakenly supplied as feverfew. For candidate species in genus *Anthemis,* Roman chamomile (*Chamaemelum nobile*), also known as, *Anthemis nobilis,* is not listed. Primers used in Roman chamomile ID test yield *Chamaemelum nobile* as the only species. Primers used in Chinese chamomile ID test yield only *Chrysanthemum* spp., which include the target species, *Chrysanthemum indicum* and *Chrysanthemum* x *morifolium*. Although in-silico analysis indicated that feverfew ID test and Chinese chamomile ID test may not be specific to the targeted species, each individual test is specificity to the species in the test scope by in-silico prediction (Table 3).

Figure 9:
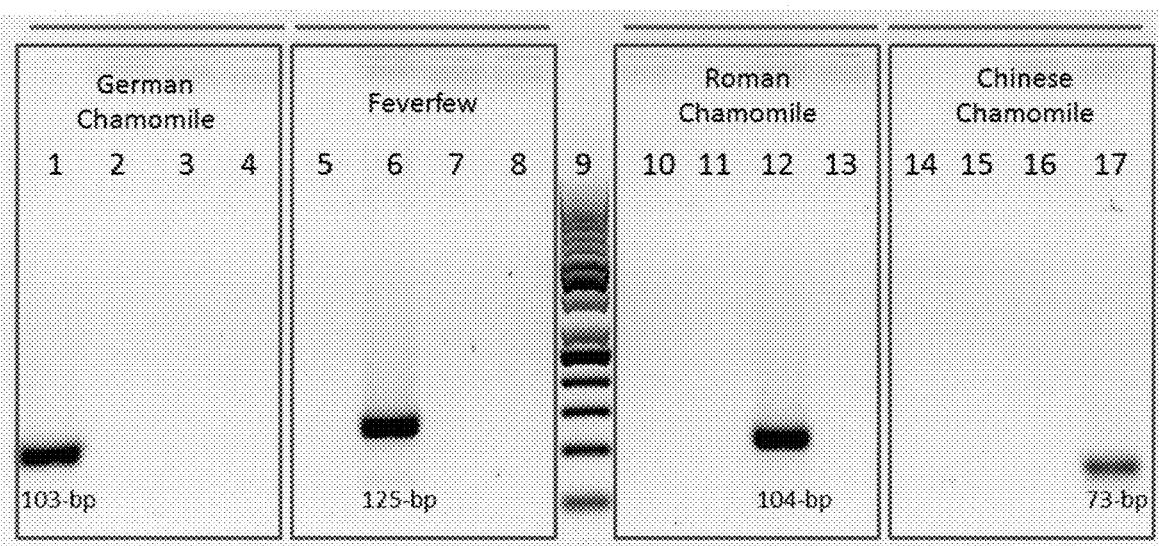
FIG. 9 depicts agarose gels of PCR products from botanical reference material (BRM) following a chamomile authentication test. Lanes 1-4: chamomile authentication test result for *Matricaria recutita* (German chamomile) BRM produced a 103-bp amplicon in lane 1. Lanes 5-8: chamomile authentication test result for *Tanacetum parthenium* (feverfew) BRM produced a 125-bp amplicon in lane 6. Lane 9: 50-bp molecular marker. Lanes 10-13: chamomile authentication test result for *Chamaemelum nobile* (Roman chamomile) BRM produced a 104-bp amplicon in lane 12. Lanes 14-17: chamomile authentication test result for *Chrysanthemum indicum* (Chinese chamomile) BRM produced a 73-bp amplicon in lane 17. Lanes 1, 5, 10, 14: *Matricaria recutita* (German chamomile) test. Lane 2, 6, 11, 15: *Tanacetum parthenium* (feverfew) test. Lane 3, 7, 12, 16: *Chamaemelum nobile* (Roman chamomile) test. Lane 4, 8, 13, 17: *Chrysanthemum indicum* (Chinese chamomile) test.
Figure 10A:
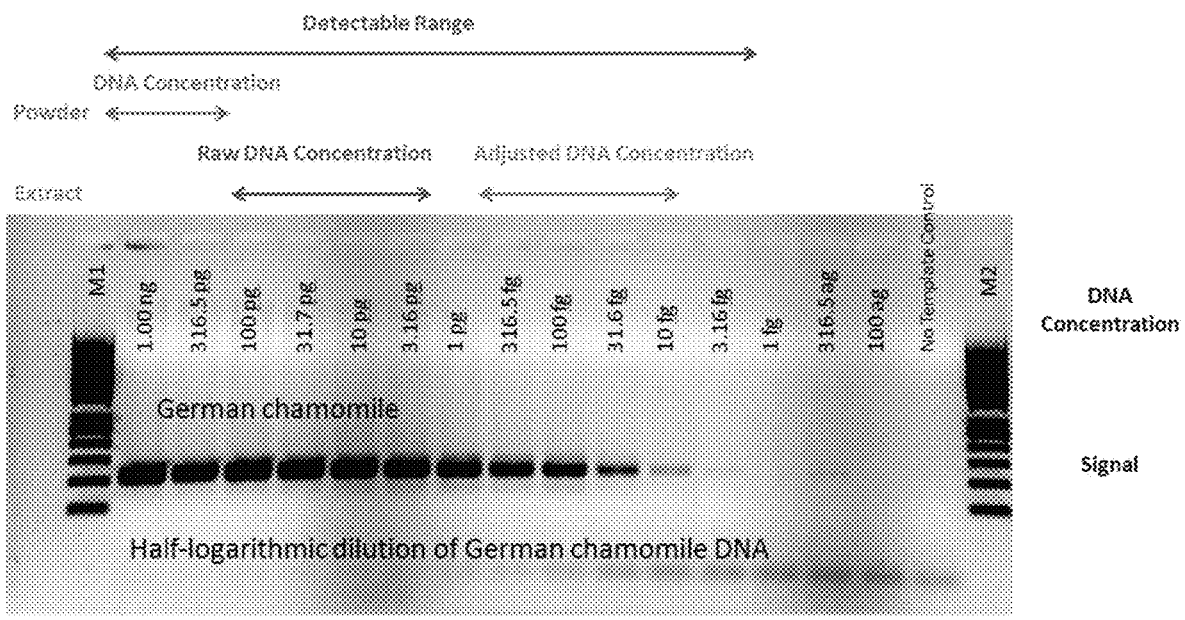
FIG. 10A depicts an agarose gel showing the limit of detection of a German chamomile test. Genomic German chamomile DNA was prepared from *Matricaria chamomilla* BRM and various quantities of DNA were subjected to amplification by German chamomile test. Lanes M1 and M2 show a 50-bp ladder. Genomic DNA at a starting concentration of 1 ng/µL was subjected to half-log dilutions, and 3 µL of each of the dilutions was used in a 20 µL PCR system. 10 µL of each of the reactions was loaded on the gel. Amplifications using 1.00 ng/µL, 316.5 pg/µL, 100 pg/µL, 31.7 pg/µL, 10 pg/µL, 3.16 pg/µL, 1 pg/µL, 316.5 fg/µL, 100 fg/µL, 31.6 fg/µL, 10 fg/µL, 3.16 fg/µL, 1 fg/µL, 316.5 ag/µL, 100 ag/µL, and no template control are shown. A representative of three experiments is shown, with the limit of detection for German chamomile DNA of about 3 fg. Similar tests were performed to indicate the limit of detection for feverfew DNA (FIG. 10B—limit of detection of about 0.3 fg), Roman chamomile DNA (FIG. 10C—limit of detection of about 1 fg), and Chinese chamomile DNA (FIG. 10D—limit of detection of about 30 fg).
Figure 10B:
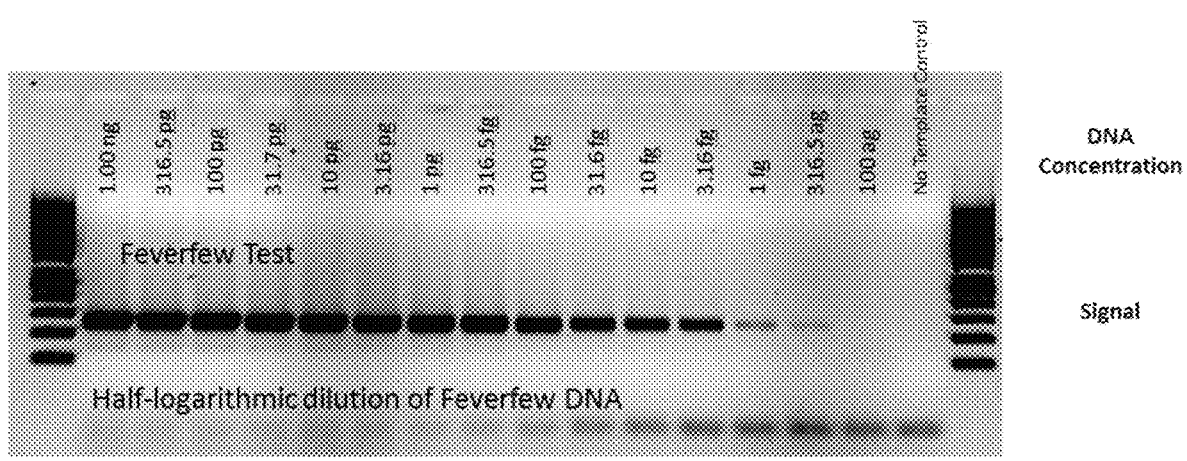
Figure 10C:
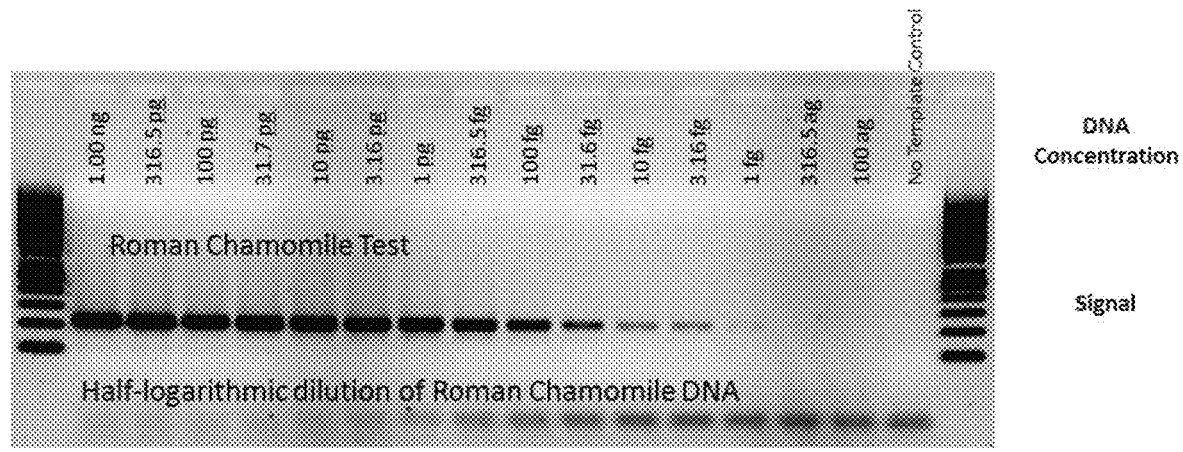
Figure 10D:
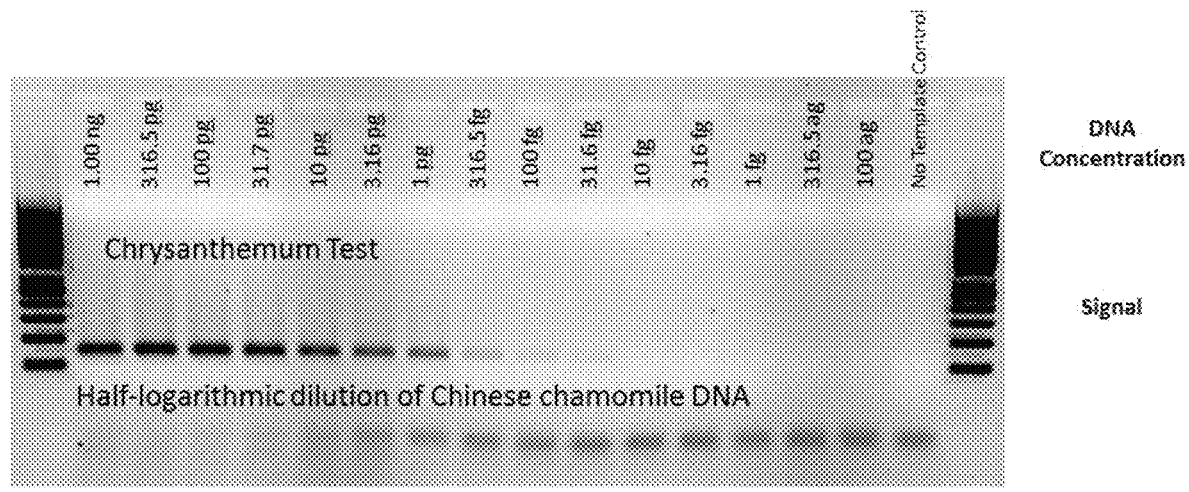

Since in-silico prediction does not consider the limitations and variations of biochemical reaction in the PCR tube and the majority genome sequences in the targeted species have not been sequenced (Henriques, et al. (2012). *BMC Res Notes,* 5, 637; Huws, et al. (2007). *J Microbiol Methods,* 70(3), 565-569; Morales, et al. (2009). *Appl Environ Microbiol,* 75(9), 2677-2683, each of which is incorporated by reference herein in its entirety), experimental analytic specificity was assessed using BRMs that represent target species in the test scope. *Matricaria chamomilla, Tanacetum parthenium, Chamaemelum nobile,* and *Chrysanthemum* x *morifolium* BRMs were included in the analysis, where genomic DNA of each BRM species was tested by the whole chamomile authentication test for cross-reactivity. German chamomile ID test produced an amplicon around 100 bp (expected size, 103 bp), no amplicon was amplified from non-target species (FIG. 9, Lane 1, 5, 10, and 14). Feverfew ID test produced a major amplicon between 100 bp and 150 bp (expected size, 125 bp) and a minor amplicon between 50 bp and 100 bp, no amplicon was amplified from non-target species (FIG. 9, Lane 2, 6, 11, and 15). Roman chamomile ID test produced a major amplicon around 100 bp (expected size, 104 bp) and a minor amplicon around 50 bp, no amplicon was amplified from non-target species (FIG. 9, Lane 3, 7, 12, and 16). Chinese chamomile ID test produced an amplicon between 50 bp and 100 bp (expected size, 73 bp), no amplicon was amplified from non-target species (FIG. 9, Lane 4, 8, 13, and 17). The above result indicated that the German chamomile authentication test was specific for the species in the test scope.

Analytical sensitivity, also known as limit of detection (LOD), is defined as the lowest concentration of genomic DNA can be reliably detected and distinguished from a negative result. LOD is crucial, because the German chamomile authentication test is being used to detect the presence of chamomile signal in DNA of low quantity. Because individual test targets different DNA sequences with various copy number in the genome, the LOD for each test must be evaluated separately. To address the LOD for each individual test, serial half-log dilutions were made from each BRM genomic DNA. For each dilution, 3 µL was used as DNA template for PCR. The signal intensity of the expected amplicon was evaluated on agarose gels. The LOD was 3.16 fg/µL, 316.5 ag/µL, 1 fg/µL, and 31.6 fg/µL for German chamomile, feverfew, Roman chamomile, and Chinese chamomile ID test, respectively (FIGS. 10A-10D).

Figure 11:
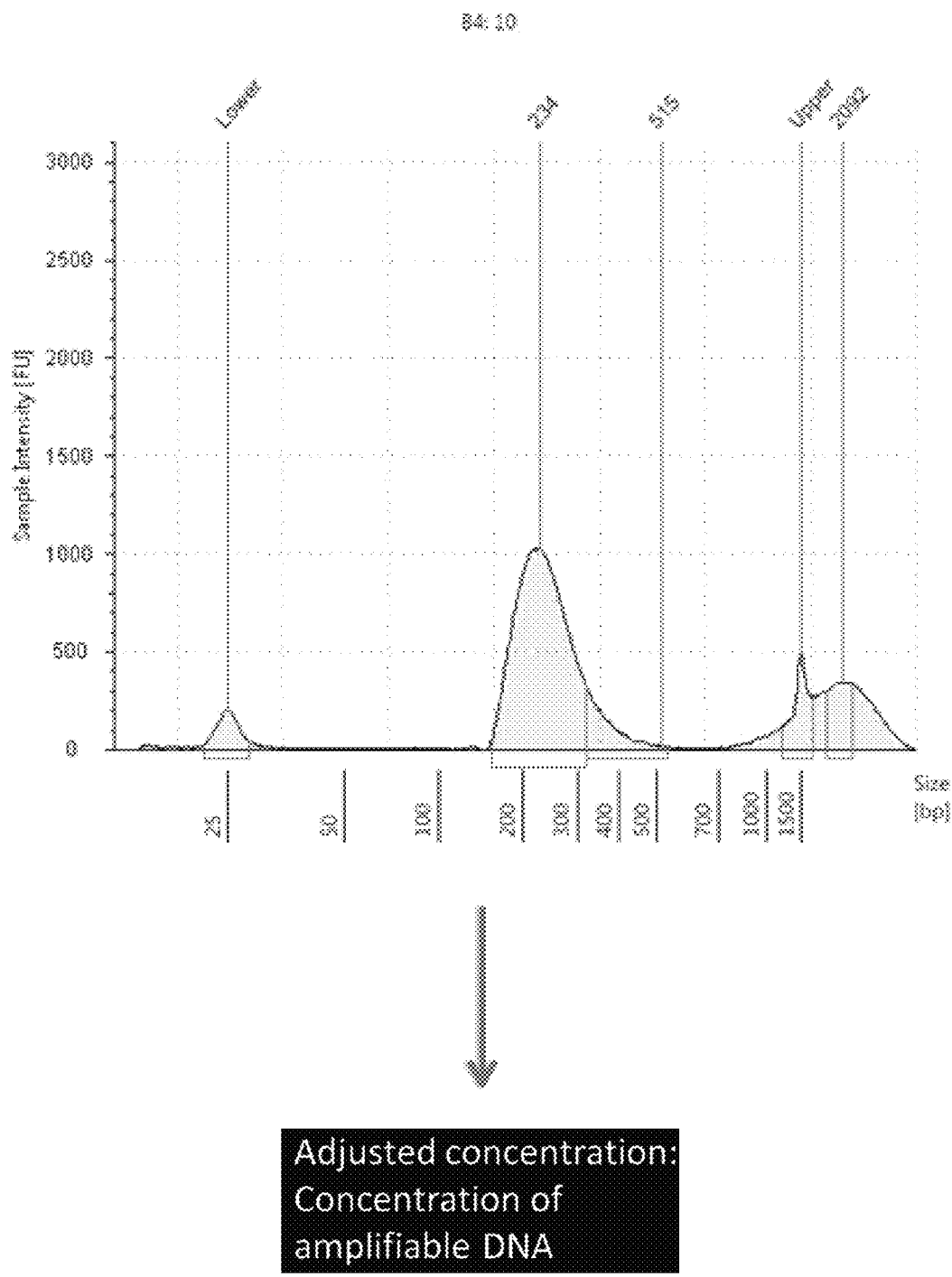
FIG. 11 depicts the sample intensity of genomic DNA fragments after PCR amplification used to calculate the original amplifiable genomic DNA isolated from botanical extracts. The estimated concentration of amplifiable genomic DNA is between 1 pg/µL and 400 fg/µL.

Since LOD was determined based on genomic DNA in good quality and the raw genomic DNA concentration from botanical extracts measured by Qubit also include the heavily degraded DNA, the actual amount of amplifiable genomic DNA remains to be determined. With the genomic DNA fragment size available after PCR amplification, the original amplifiable genomic DNA isolated from botanical extracts was calculated (FIG. 11). The estimated concentration of amplifiable genomic DNA was between 1 pg/µL and 400 fg/µL, which were still above the detection limit of the German chamomile ID test (FIG. 7A). Characterizing genomic DNA isolated from feverfew, and Chinese chamomile also provides evidence for the feasibility of using feverfew and Chinese chamomile ID test for German chamomile adulterants detection.

Figure 12A:
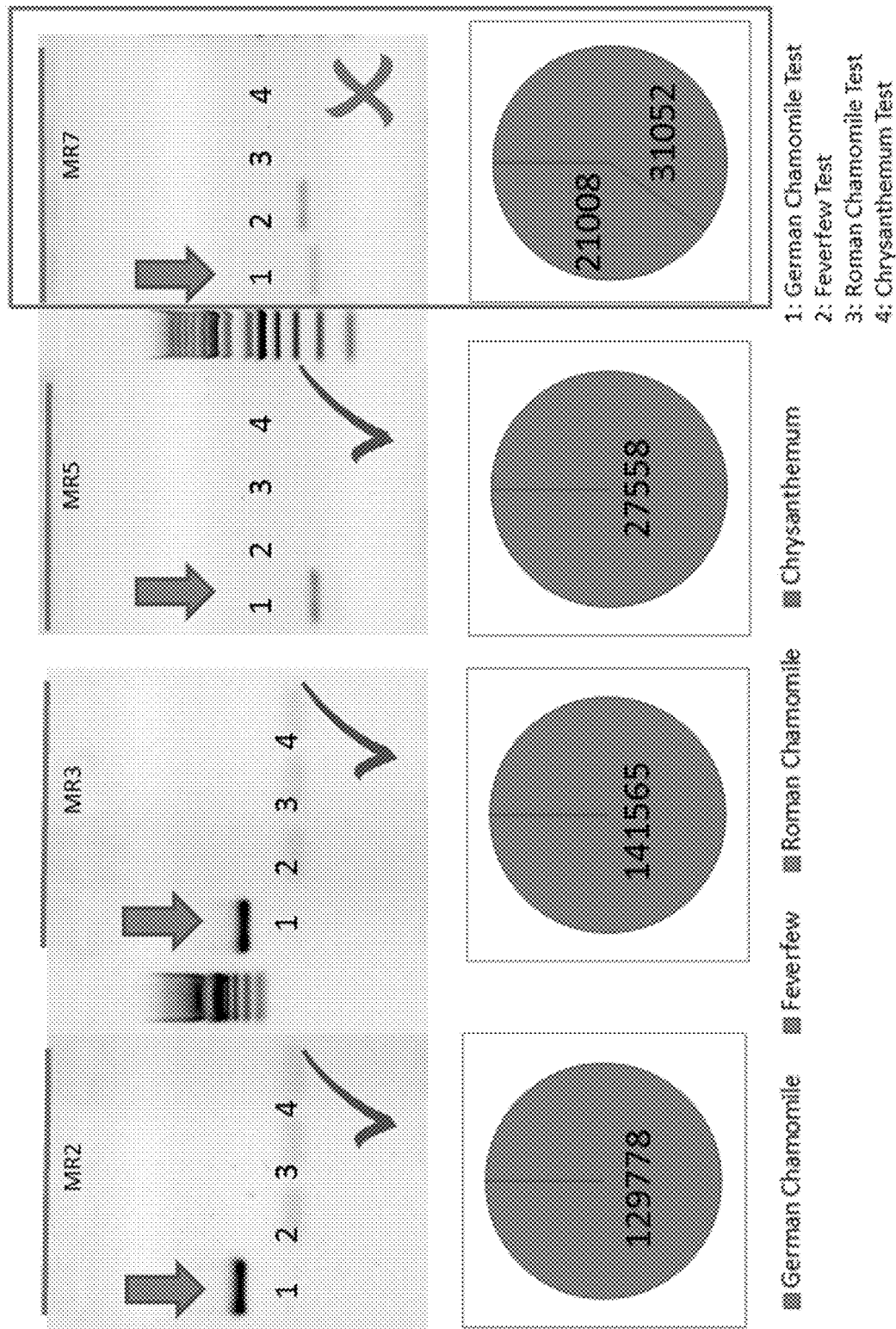
FIG. 12A illustrates results of a chamomile authentication test applied to German chamomile dietary supplements that are commercially available. Samples from manufacturers 2, 3, and 5 (MR2, MR3, and MR5) test positive for German chamomile. However, sample from MR7 indicates a mixture of German chamomile and feverfew (about 60% to 40%, respectively).

The chamomile authentication test was applied to German chamomile dietary supplements sold on the market. The results showed that German chamomile ID test is positive for all three tested German chamomile powders and all three German chamomile extracts (FIG. 12A). However, sample form manufacturer 7 (MR7) was also positive for the feverfew ID test.

Figure 12B:
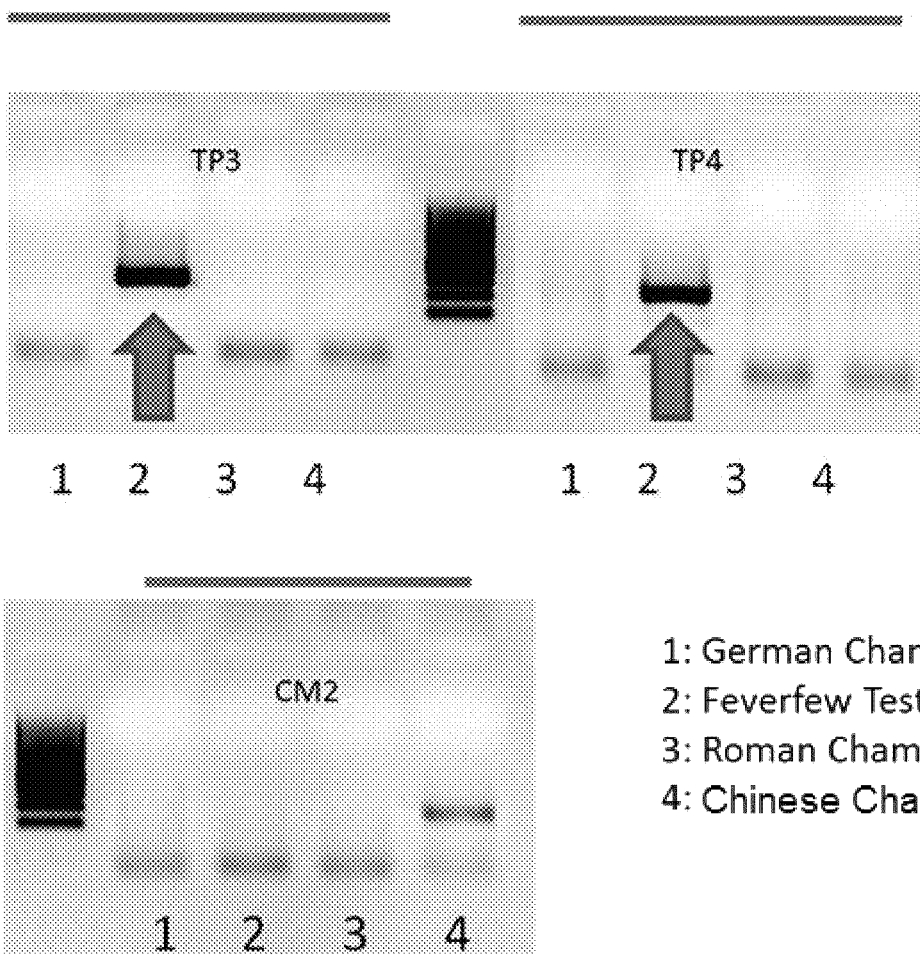
FIG. 12B shows gels that test positive for feverfew (top two gels) and Chinese chamomile (bottom gel).

To demonstrate that the other tests can successfully detect botanical substitution and contamination, two additional feverfew and one Chinese chamomile extract were tested. The results showed that feverfew ID test is able to amplify feverfew specific signal from both tested feverfew extract and Chinese chamomile ID test amplified specific signal from the Chinese chamomile extract (FIG. 12B).

To validate the result of DNA-based chamomile authentication test, a signature region that can differentiate all species in test scope was amplified by a set common primer. Next-generation sequencing was used to tally reads and assign species identity based on signature sequences (FIG. 12A). Only German chamomile signature sequence was amplified and read by sequencer in three German chamomile powders and two extracts. Sample from manufacturer 7 (MR7) shows signature sequence from both German chamomile and feverfew, which is consistent with the result from German chamomile authentication test. NGS is also able to confirm the presence of feverfew signature in two feverfew extracts and one Chinese chamomile extracts.

Example 3

Figure 13:
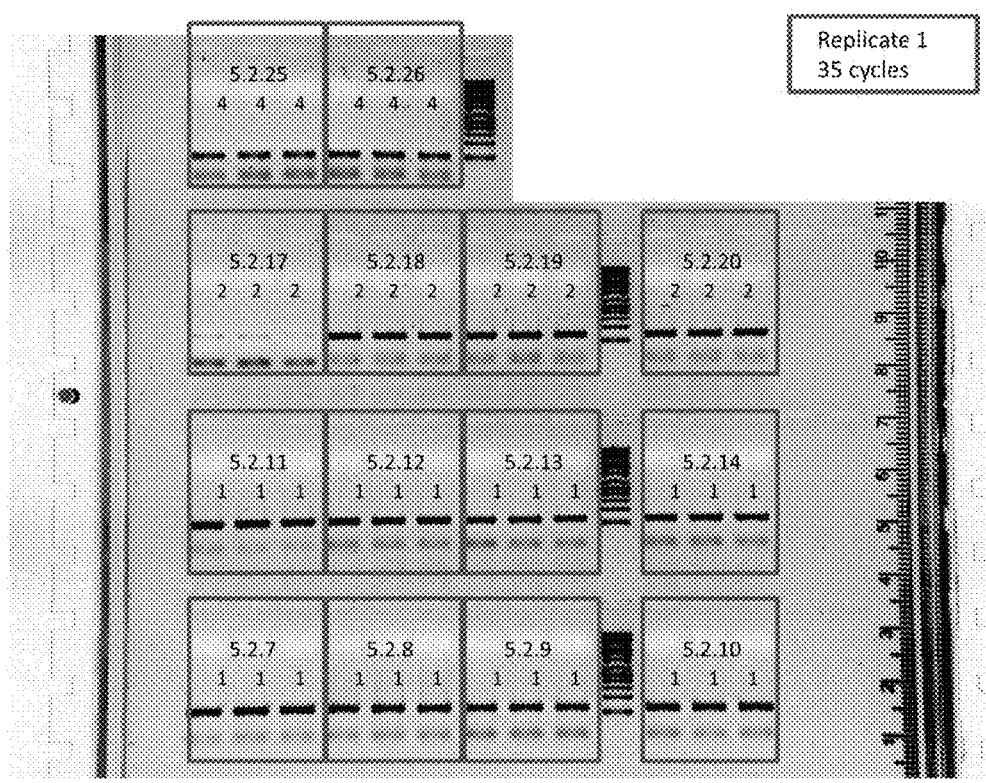
FIG. 13 shows chamomile authentication test detects target botanical in multiple chamomile extracts manufactured under different conditions and from different sources.

Authentication of German Chamomile Dietary Supplements in the Context of Feverfew Adulteration by Targeted PCR To further demonstrate the high probability of detection of the DNA-based chamomile authentication test in real life situation, a proof-of-concept example using German chamomile as target botanical and feverfew as potential adulterants was designed. In this example, additional German chamomile extracts manufactured under different conditions and diluted DNA from feverfew extracts were tested (Table 10). In detail, three independent DNA extractions were performed on German chamomile extracts [6 in-house+2 commercial]. Each sample was tested by German chamomile ID test in triplicates to reach 72 replicates for statistical probability of detecting target botanical material with 95% confidence. Three independent DNA extractions were performed on 2 common adulterant powders and plant parts [6 commercial]. Each sample was further diluted to 5% of its original concentration and evaluated by feverfew ID test in triplicates to reach 54 replicates (a minimum of 51) for probability of detecting non-target adulterant botanical materials with 95% confidence. One representative result was shown in FIG. 13 and sample information listed in Table 10.

TABLE 10

Botanical extracts cover different extraction solvents, storage time spans, and different manufacture facilities

| Sample | Botanicals | Extraction solvents | Source |
|---|---|---|---|
| 5.2.7 | German Chamomile | Water 90-80%/Ethanol 10-20% | In-house |
| 5.2.8 | German Chamomile | Water 90-80%/Ethanol 10-20% | In-house |
| 5.2.9 | German Chamomile | Water 90-80%/Ethanol 10-20% | In-house |
| 5.2.10 | German Chamomile | Water 100% | In-house |
| 5.2.11 | German Chamomile | Water 20%/Ethanol 80% | In-house |
| 5.2.12 | German Chamomile | Water 50%/Ethanol 50% | In-house |
| 5.2.13 | German Chamomile | N/A | Manufacturer 1 |
| 5.2.14 | German Chamomile | N/A | Manufacturer 2 |
| 5.2.17 | Feverfew | N/A | Manufacturer 3 |
| 5.2.18 | Feverfew | N/A | Manufacturer 4 |
| 5.2.19 | Feverfew | N/A | Manufacturer 5 |
| 5.2.20 | Feverfew | N/A | Manufacturer 6 |
| 5.2.25 | Feverfew | N/A | Manufacturer 7 |
| 5.2.26 | Feverfew | N/A | Manufacturer 8 |

Example 4

Characterization and Authentication of Ginseng DNA Fragments from Dietary Supplements by Targeted Sequencing In certain circumstances, targeted amplification of DNA sequence does not have enough discrimination power to differentiated close species, so after confirming the existence and size of the target botanical DNA, a test scope specific primer was designed to amplify species signature regions and the fragment was subjected to DNA sequencing for botanical authentication purpose. The following example demonstrates a method for authenticating botanical DNA fragments from an Asian ginseng dietary supplement, which has many similar close species also sold on the market.

Figure 14:
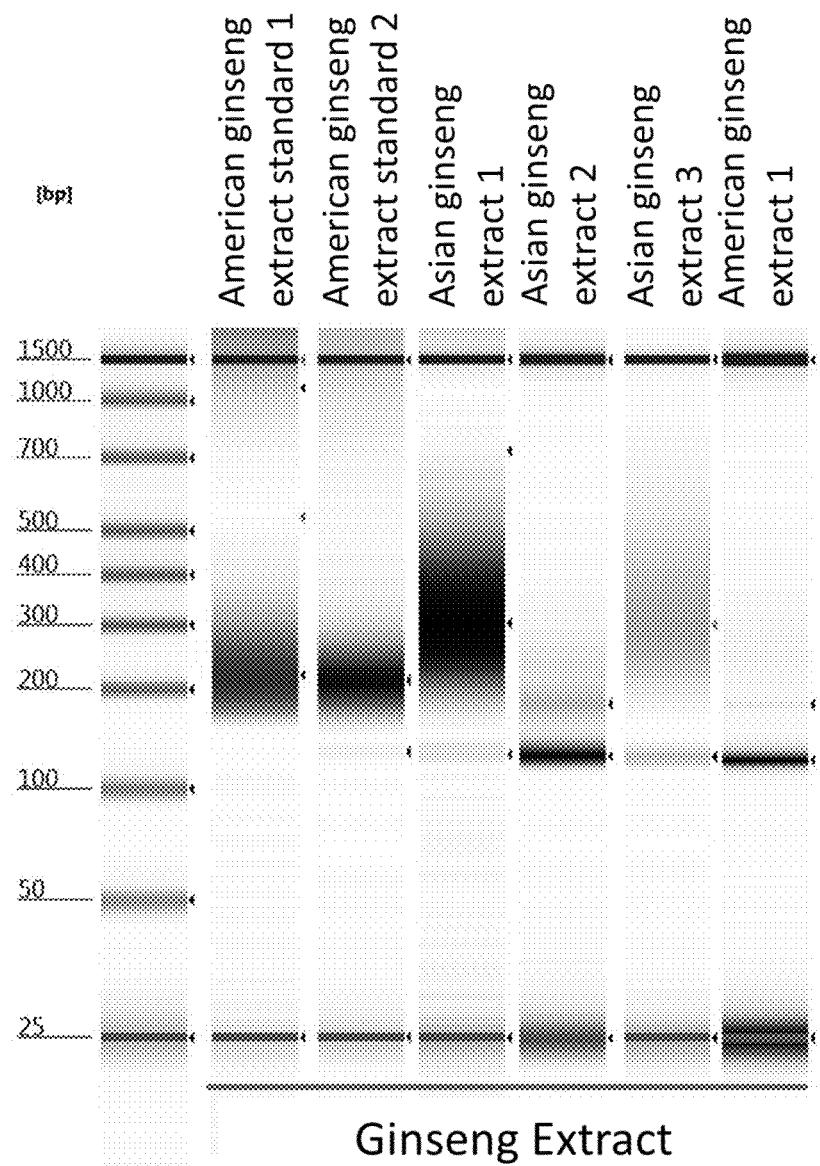
FIG. 14 shows DNA smears were observed in all tested *ginseng* extract with fragment size ranged from 150-bp to 350-bp.

To detected fragmented DNA in *ginseng* extract product, DNA isolations were ligated by adapter followed by 12 cycles of PCR amplification. The optimized amplification protocol included 1 cycle of 5 minutes at 95° C., followed by 12 cycles of 30 seconds at 95° C., 30 seconds at 58° C., 2 minutes at 72° C., and a final extension step at 72° C. for 5 minutes. The resulted PCR products were purified with Agencourt AMPure XP beads (1.0×) and eluted with 25 µL of water before detection. DNA smears were observed in all processed botanical extractions with size ranged from 150-bp to 350-bp (FIG. 14).

Figure 15:
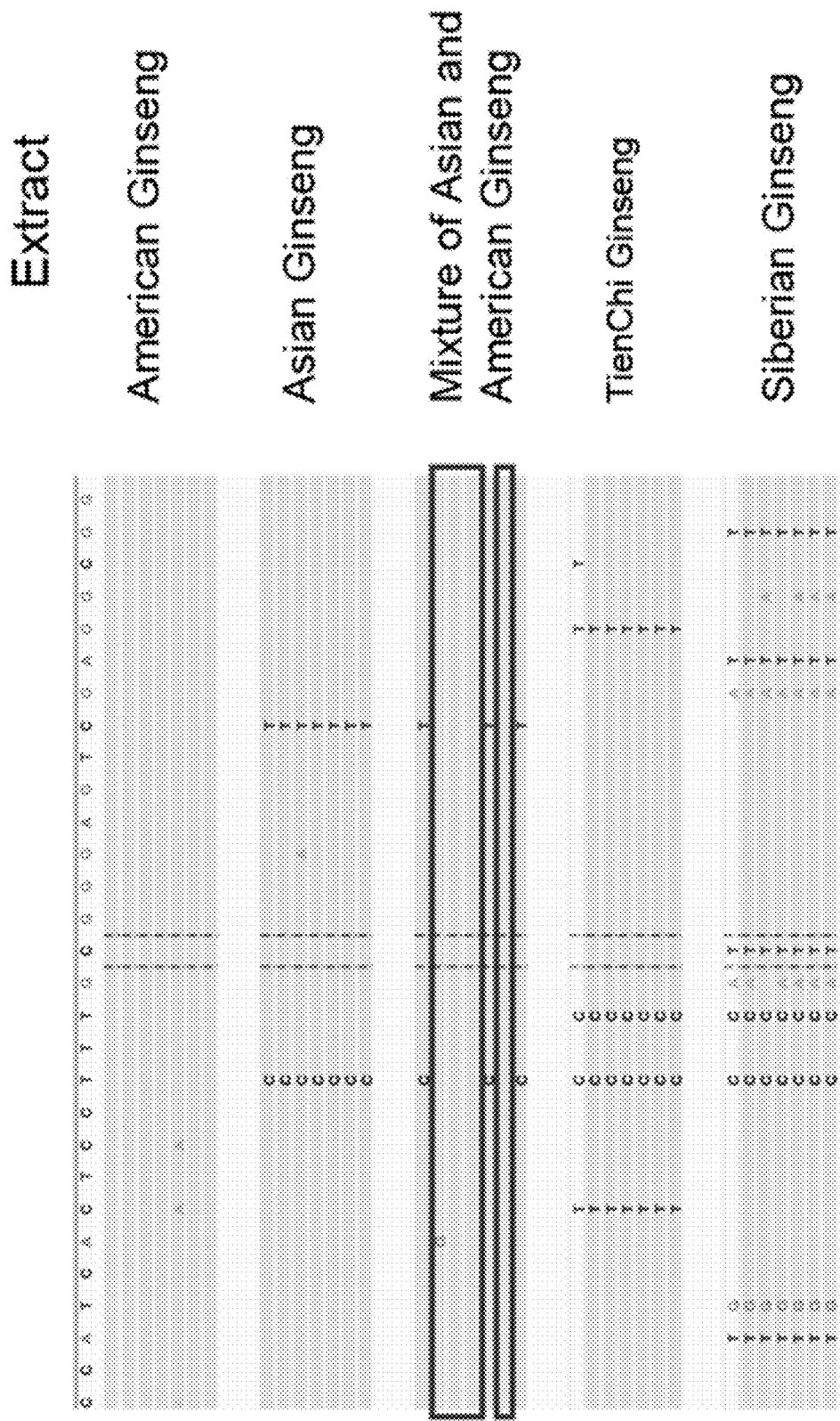
FIG. 15 shows representative signature sequence alignments from DNA isolated from Asian ginseng, American ginseng, mixed Asian ginseng and American ginseng, Tienchi Ginseng and Siberian ginseng extracts.

To differentiate Asian ginseng (*Panax ginseng*) from American ginseng (*Panax quinquefolius*), Tienchi Ginseng (*Panax notoginseng*) and Siberian ginseng (*Eleutherococcus senticosus*), a scope specific common primer set (SEQ ID 11 and SEQ ID 12 flanked with Illumina adaptor sequence) was designed to amplify and enrich the Asian ginseng signature regions. The optimized amplification protocol included 1 cycle of 5 minutes at 95° C., followed by 35 cycles of 30 seconds at 95° C., 30 seconds at 58° C., 30 seconds at 72° C., and a final extension step at 72° C. for 2 minutes. The resulted PCR products were purified with Agencourt AMPure XP beads (1.0×) and further indexed and subjected to sequencing by MiSeq. FIG. 15 shows representative signature sequence alignment from DNA isolated from Asian ginseng, American ginseng, mixed Asian ginseng and American ginseng, Tienchi Ginseng and Siberian ginseng extracts.

Based on the signature sequence, Asian ginseng extract can be authenticated by comparing to Table 3. Other botanicals in Tables 2 and 3 can be authenticated in similar fashion.

Example 5

Characterization and Authentication of Tea DNA Fragments from Dietary Supplements by Tiling Sequencing of Two-Tiered DNA Barcode For raw botanical parts, the use of multiple full-length DNA barcodes (400-800 bp) that extends the total target barcode sequence length for botanical authentication has been accepted by many researchers and study projects. Studies show that a two-locus combination gives better discrimination power than a single-locus, while a three-locus combination does not provide additional discrimination power over the optimal two-locus combination. The choice of two barcodes in the current method is a compromise between barcode discrimination power and cost.

Barcodes were derived from either coding or non-coding regions. Coding region barcodes encode proteins, so the pattern of nucleotide substitution in these barcode region was restrained by conservative protein domains or motifs (21). As a result, their discrimination power at the species level was not completely adequate. In contrast, non-coding region barcodes are less restrained in evolution, so the resulting higher sequence diversity leads to higher discrimination power at the species level. Many researchers use two-tiered DNA barcode strategy, which 1) separates coding and non-coding region barcodes into two tiers, and 2) examines DNA barcodes from each tier. This not only maintain the efficiency of using bioinformatics tools in the first tier (coding) barcodes, but also retains optimal discrimination power that is possessed mainly by the second tier (non-coding) barcodes.

Figure 16A:
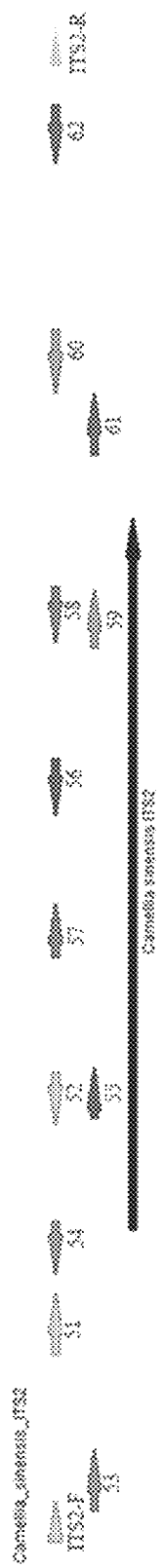
FIGS. 16A and 16B shows design of tiling primer sets that cover the full length *Camellia sinensis* ITS2 (FIG. 16A) and rbcL (FIG. 16B) barcode regions. Horizontal triangles represent the regions covered by conventional ITS2 and rbcL primers. Numbers under horizontal arrows represent SEQ ID numbers.
Figure 16B:
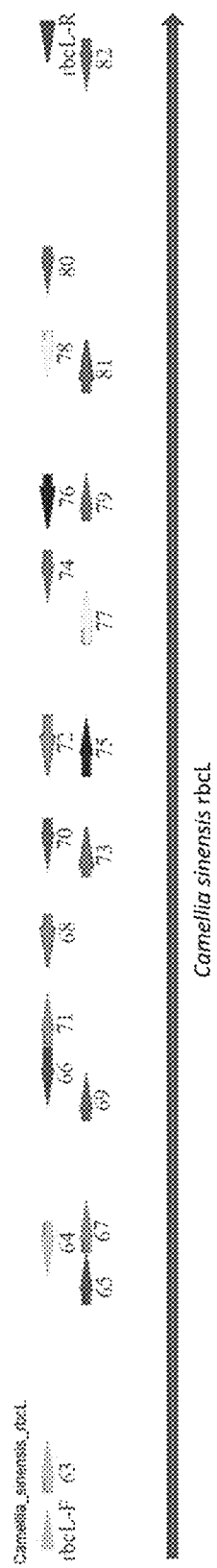

Method for authenticating raw botanical material ingredients using two-tiered DNA barcoding to meet regulatory compliance was performed. However, for fragmented DNA in botanical extract, small DNA size prevented successful collection of two-tiered full-length DNA barcodes. For example, DNA in green tea and black tea was usually below 400 bp (FIG. 6B in Example 1). In order to collect two-tiered full length DNA barcodes, a tiling amplicon sequencing was performed to reconstruct the full length DNA barcode. FIG. 16 shows a set of tiling PCR primers designed for reconstructing *Camellia sinensis* ITS2 and rbcL barcode regions.

Tea genomic DNA was isolated using a DNeasy Plant Mini Kit (Qiagen, Germantown, MD, USA), according to the manufacturer's instructions. Four multiplex PCR amplifications were carried out in a 20 µL reaction mixture containing 10 µL of 2× AmpliTaq Gold® 360 Master Mix (Applied Biosystems, Waltham, MA, USA), 2 μL of genomic DNA isolate, 2 μL of primers pool (Table 11), and 1 μL of water. The PCR reaction was performed in a Bio-Rad C-1000 Touch Thermal Cycler (Bio-Rad, Hercules, CA, USA). The optimized amplification protocol consisted of 1 cycle of 5 minutes at 95° C., followed by 35 cycles of 30 seconds at 95° C., 30 seconds at 56° C., 30 seconds at 72° C., and a final extension step at 72° C. for 3 minutes.

TABLE 11

Primer pools for tiling sequencing.

| Pool 1 | Pool 2 | Pool 3 | Pool 4 |
| --- | --- | --- | --- |
| SEQ ID NO: 51 | SEQ ID NO: 53 | SEQ ID NO: 55 | SEQ ID NO: 57 |
| SEQ ID NO: 52 | SEQ ID NO: 54 | SEQ ID NO: 56 | SEQ ID NO: 58 |
| SEQ ID NO: 59 | SEQ ID NO: 61 | SEQ ID NO: 63 | SEQ ID NO: 65 |
| SEQ ID NO: 60 | SEQ ID NO: 62 | SEQ ID NO: 64 | SEQ ID NO: 66 |
| SEQ ID NO: 67 | SEQ ID NO: 69 | SEQ ID NO: 71 | SEQ ID NO: 73 |
| SEQ ID NO: 68 | SEQ ID NO: 70 | SEQ ID NO: 72 | SEQ ID NO: 74 |
| SEQ ID NO: 75 | SEQ ID NO: 77 | SEQ ID NO: 79 | SEQ ID NO: 81 |
| SEQ ID NO: 76 | SEQ ID NO: 78 | SEQ ID NO: 80 | SEQ ID NO: 82 |

Note:
for each pool, equal volume of primer (10 μM) solution is combined to reach the final desired volume.

Figure 17:
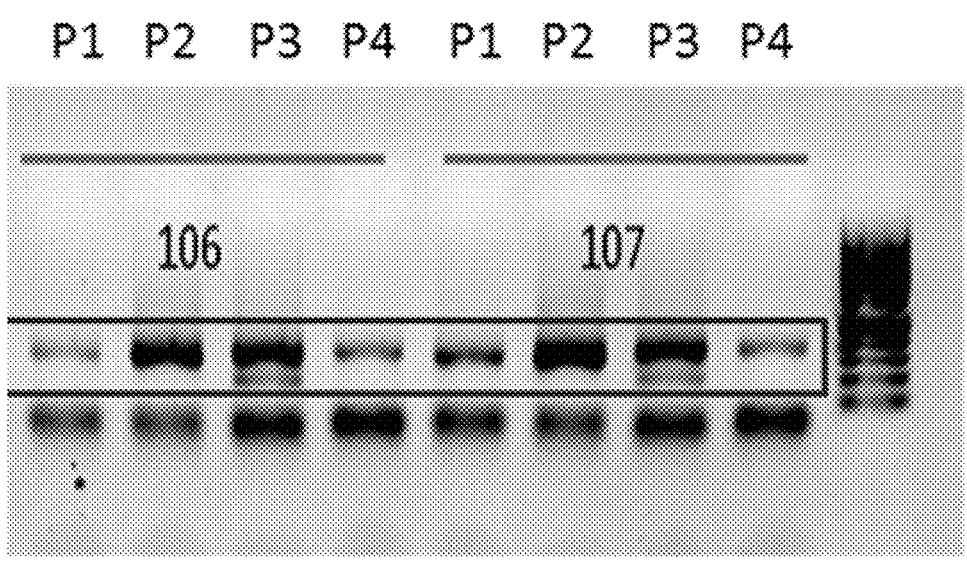
FIG. 17 shows representative multiplex PCR product (red box) based DNA isolated from 2 tea extracts (No. 106 and No. 107). P1-P4 means multiplex PCR Pool1-Pool4.

Representative multiplex PCR results were shown in FIG. 17. These PCR products were further indexed and amplified. The optimized amplification protocol included 1 cycle of 5 minutes at 95° C., followed by 12 cycles of 30 seconds at 95° C., 30 seconds at 58° C., 2 minutes at 72° C., and a final extension step at 72° C. for 5 minutes. The resulted PCR products were purified with Agencourt AMPure XP beads (1.0×) and eluted with 25 μL of water before sequencing.

Figure 18A:
FIGS. 18A and 18B shows short sequencing reads aligned against *Camellia sinensis* ITS2 (FIG. 18A) and rbcL (FIG. 18B) barcode regions. Numbers represent SEQ ID numbers.
Figure 18B:
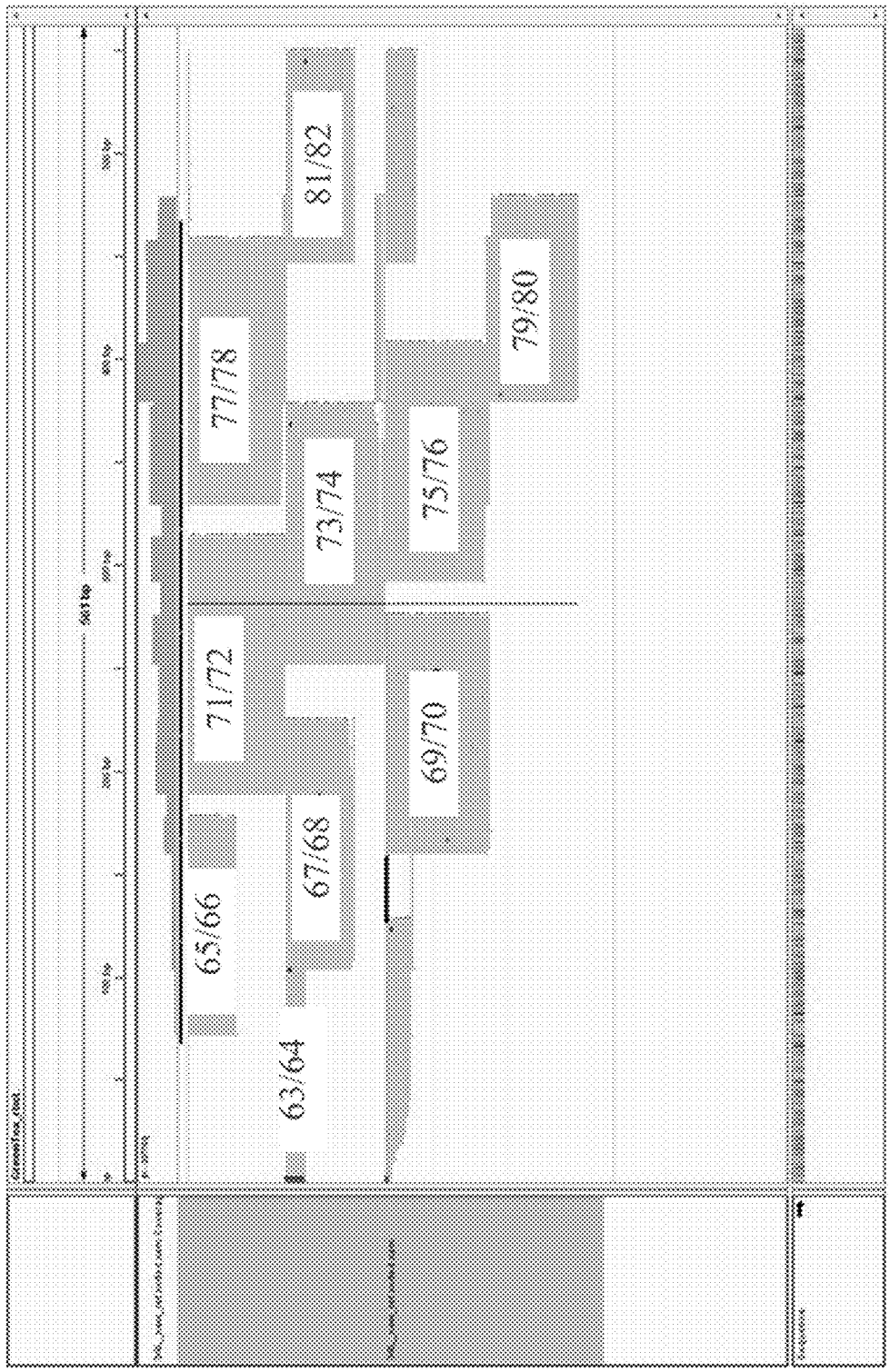
Figure 19:
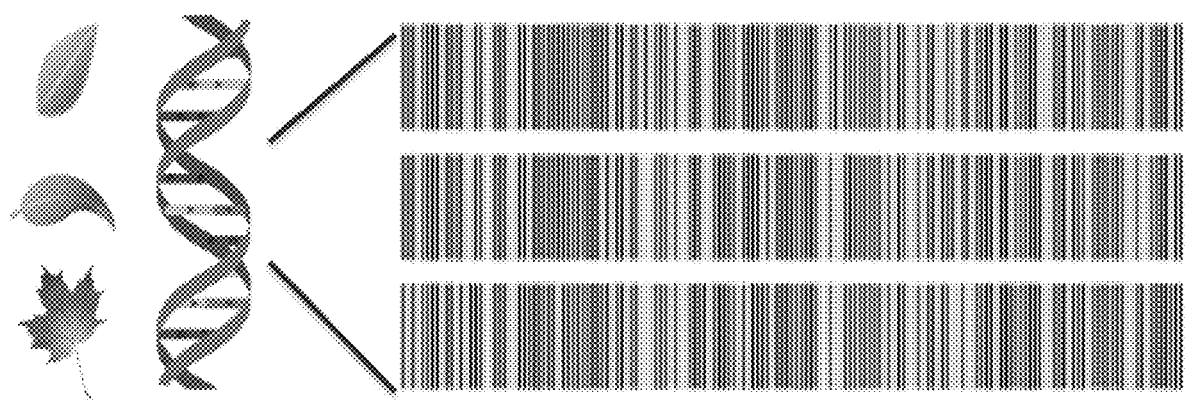
FIG. 19 illustrates botanical DNA barcodes, a unique DNA sequence for identification of individual botanical species.

Sequencing was performed on an Illumina MiSeq platform, aligned by bowtie2 and barcode coverage calculated by bedtools. The aligned reads with high percentage of barcode sequence coverage in shown in FIG. 18.

Example 6

Two-Tiered DNA Barcoding of Raw Botanical Material

The following example demonstrates a method for authenticating botanical material using two-tiered DNA barcoding.

DNA barcoding methods for botanical identification have to be adequately validated to meet regulatory compliance. This example demonstrates a validation protocol for a two-tiered DNA barcoding method that aims to identify raw botanical ingredients used in herbal medicine. To capture a wide range of perspectives relating to DNA barcode-based botanical identification, maximum variation sampling techniques were used in both plant parts and species distance. Twenty-four authenticated botanicals were sampled from different plant parts, covering both closely and distantly-related species, to validate the two-tiered DNA barcoding method by assessing method accuracy and precision.

Figure 20A:
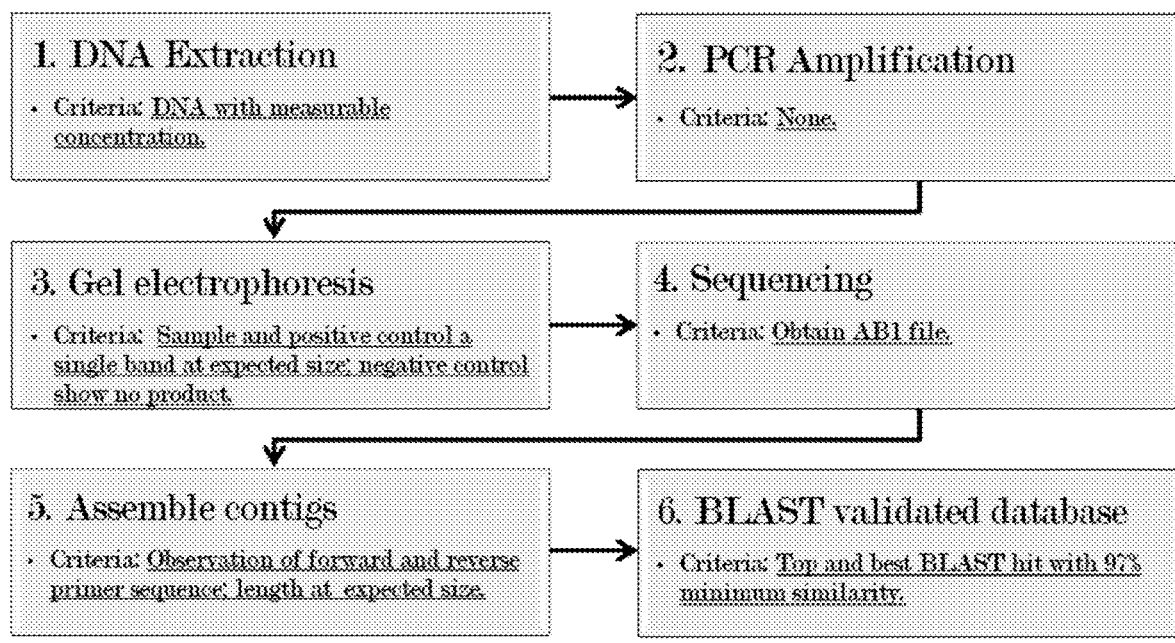
FIGS. 20A and 20B schematically outline one embodiment of a method for botanical identification of raw botanical samples.
Figure 20B:
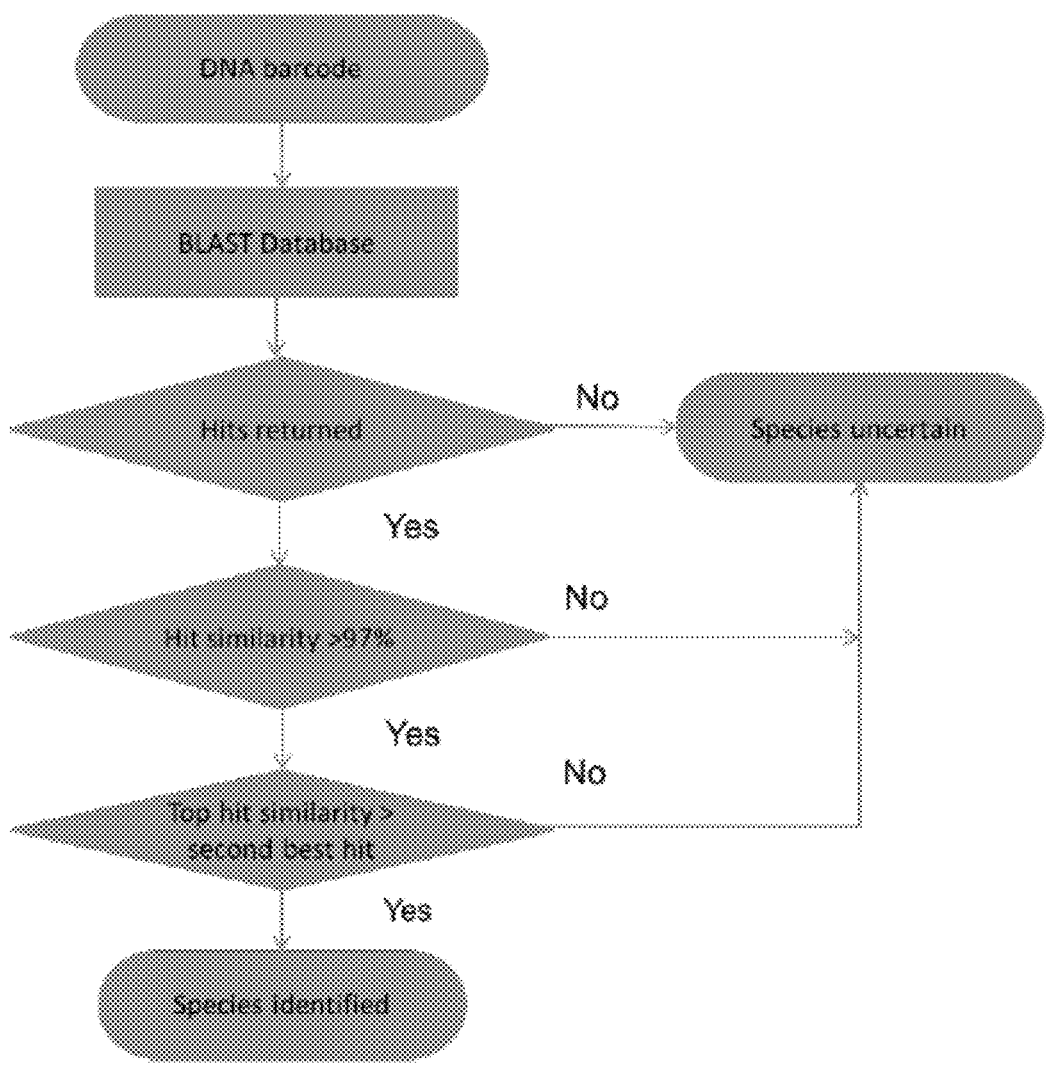

Major steps involved in raw botanical identification using two-tiered DNA barcoding are described in FIG. 20A. As outlined in FIG. 20A, a botanical material was obtained and DNA was extracted. The extracted DNA was within a measurable concentration. The extracted DNA was then amplified, for example using PCR amplification. The amplification products were submitted to gel electrophoresis. The products were then sequenced, and contigs assembled. The sequences were then submitted to BLAST. In the BLAST step, species identification were determined for each tier, the results from each tier were combined to assign the final species identification where two results did not conflict with each other.

Two-tiered validation included a first tier and a second tier. rbcL and matK coding regions were used for the first tier. The second tier barcodes included non-coding regions ITS2, trnL-trnF, and psbA-trnH. Multiple barcodes were listed under each tier, but with priority ranked. Multiple barcodes were needed, because not all barcodes could be amplified in each botanical and certain barcodes could be masked by other organisms during storage, such as ITS2 contamination from fungus. To be consistent, close species differentiation was achieved by using the same barcode combination.

Figure 21:
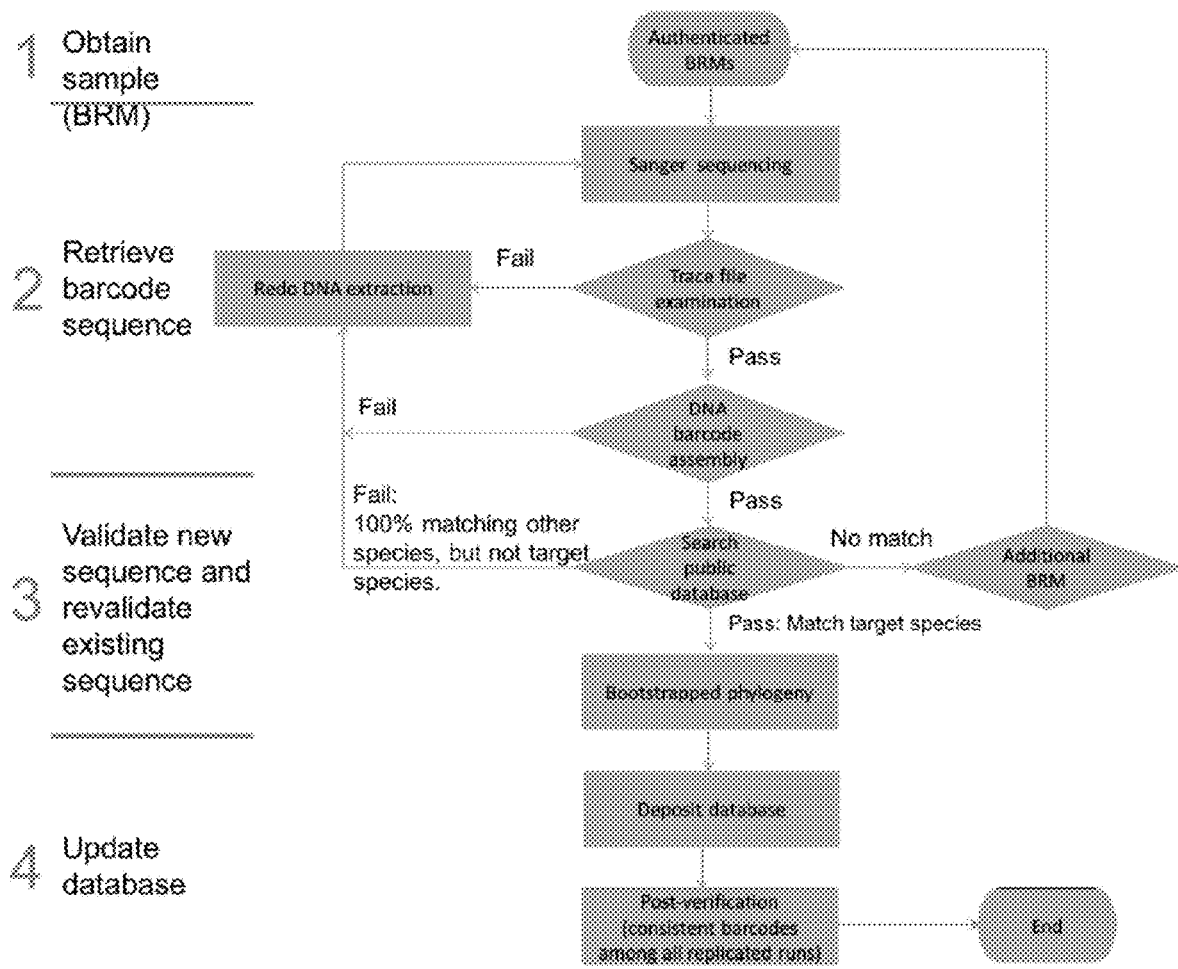
FIG. 21 schematically depicts one embodiments of a validation workflow for verification of a barcode database.

Validation was divided into two sections: barcode database validation (FIG. 21) and barcode method validation. For method validation, to capture a wide range of perspectives relating to the method, maximum variation sampling technique was used. Both DNA extraction and BLAST steps contained dimensions that diversified the test under validation, so popular botanicals and their common adulterants were chosen to fill the two dimensions (Table 12).

TABLE 12

Validation Samples.

Dimensions of Diversity

| No. | Dimension 1: Plant Part | Dimension 2: Species Distance | Common Name | Scientific Name |
| --- | --- | --- | --- | --- |
| 1 | Root | [1, 2, 3] vs [4, 5, 6] | Asian Ginseng | *Panax ginseng* |
| 2 | | | American *Ginseng* | *Panax quinquefolius* |
| 3 | | | Tienchi *Ginseng* | *Panax notoginseng* |
| 4 | | | Dong Quai | *Angelica sinensis* |
| 5 | | | Garden Angelica | *Angelica archangelica* |
| 6 | | | Pubescent Angelica | *Angelica pubescens* |
| 7 | Leaf | [7, 8] vs 9 vs 10 | Peppermint | *Mentha piperita* |
| 8 | | | Chinese Mint | *Mentha canadensis* |
| 9 | | | Green Tea | *Camellia sinensis* |
| 10 | | | Rosemary | *Rosmarinus officinalis* |

TABLE 12-continued

Validation Samples.

| | Dimensions of Diversity | | | |
|---|---|---|---|---|
| No. | Dimension 1: Plant Part | Dimension 2: Species Distance | Common Name | Scientific Name |
| 11 | Fruit | [11, 12] vs [13, 14, 15] | Schisandra | Schisandra chinensis |
| 12 | | | Southern Schisandra | Schisandra sphenanthera |
| 13 | | | Bilberry | Vaccinium myrtillus |
| 14 | | | Blueberry | Vaccinium corymbosum |
| 15 | | | Cranberry | Vaccinium macrocarpon |
| 16 | Flower | [16, 17] vs 18 | German Chamomile | Matricaria recutita |
| 17 | | | Roman Chamomile | Chamaemelum nobile |
| 18 | | | Feverfew | Tanacetum parthenium |
| 19 | Bark | [19, 20] vs 21 | Chinese Cinnamon | Cinnamomum cassia |
| 20 | | | Cinnamon | Cinnamomum zeylanicum |
| 21 | | | Mulberry | Morus alba |
| 22 | Seed | [22, 23] vs 24 | Jujube | Ziziphus spinose |
| 23 | | | Indian Jujube | Ziziphus mauritiana |
| 24 | | | Guarana | Paullinia cupana |

In this example, only accuracy and precision were evaluated, as barcode-based identification is a categorical test. Accuracy was determined by the concordance between the test result and the genus and species provided by the specimen certificate of authenticity: Accuracy=(Number of concordant assessments)/(Number of all assessments)× 100%. The acceptance criteria for accuracy should be at least at 95%.

Precision refers to the closeness of two or more measurements to each other. In this validation protocol, precision assesses the agreement between three individual tests when assigning species identities to 24 samples under testing. This measurement is also known as Fleiss' kappa. Acceptance Criteria: should be 0.90. Guidelines: almost perfect agreement (0.81-1.00).

Figure 22A:
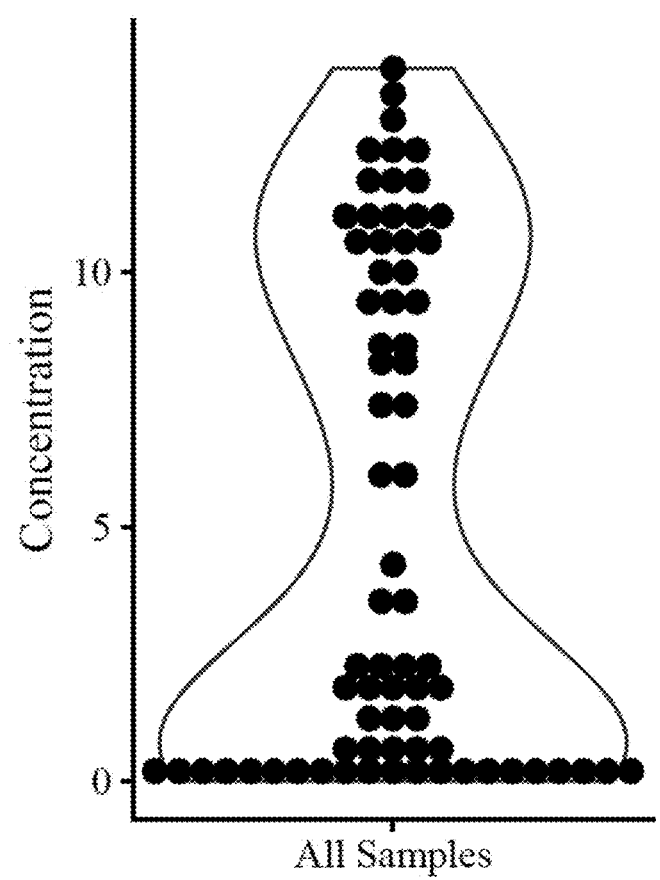
FIGS. 22A and 22B depict DNA concentration of validated samples.
Figure 22B:
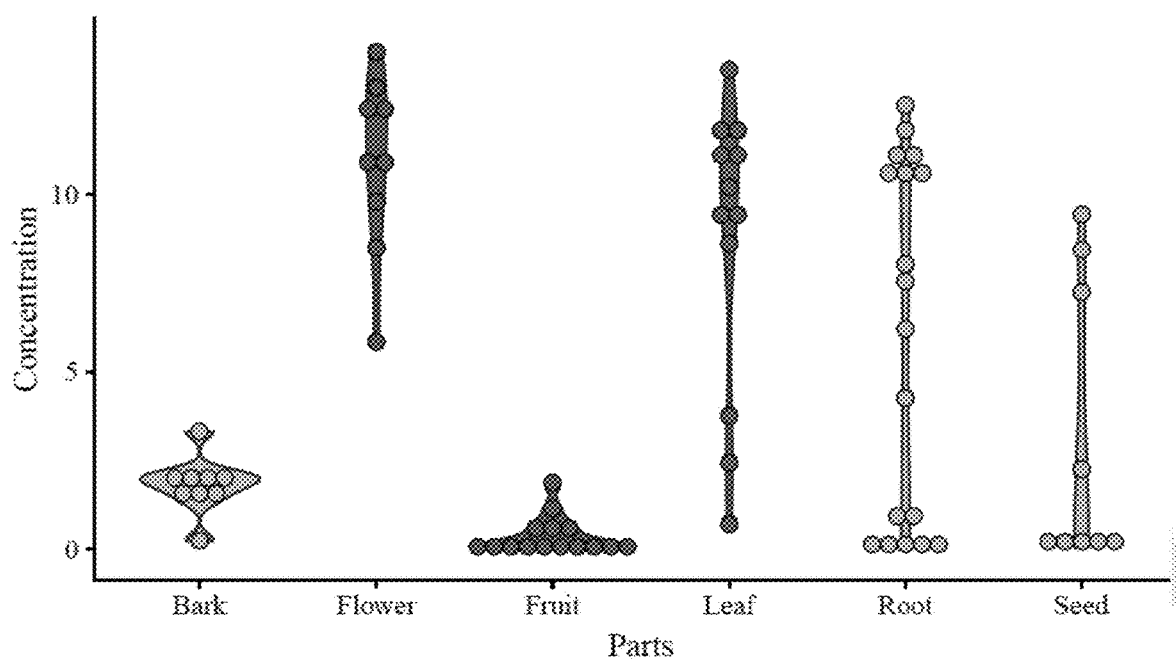

Following validation of 72 samples, all 72 samples were assigned botanical scientific names that match their true identity: Accuracy=100% Precision=1.0. DNA concentrations of validation samples showed a bimodal distribution (FIG. 22A). In terms of DNA extracted from different plant parts, bark and fruit are likely to have DNA concentration lower than DNA from other plant parts (FIG. 22B).

Figure 23A:
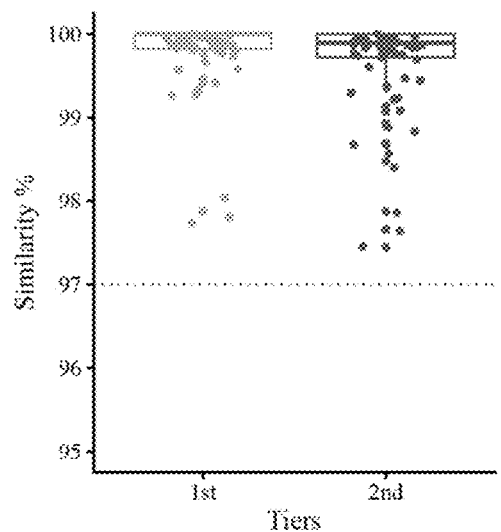
FIGS. 23A-23D show assessment of criteria for successful botanical authentication.
Figure 23B:
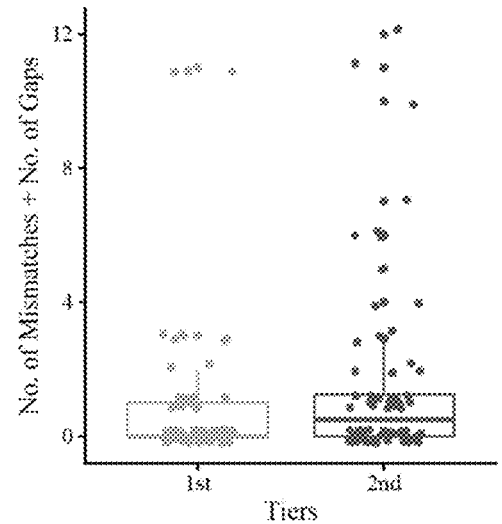
Figure 23C:
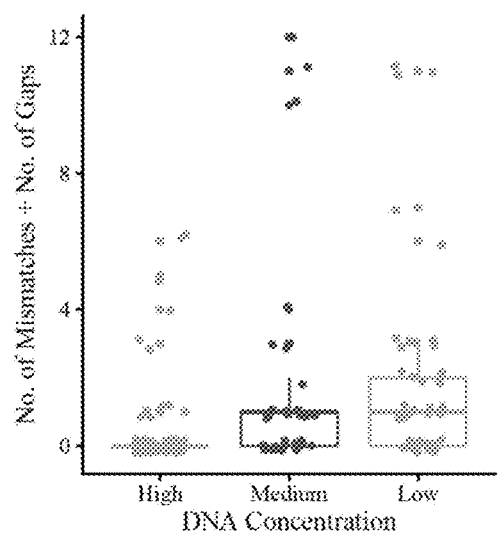
Figure 23D:
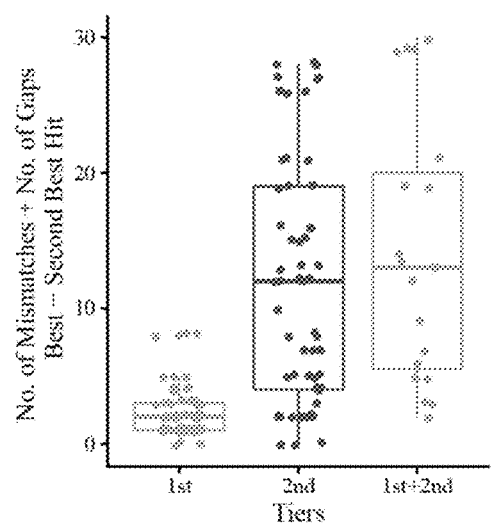

Setting the similarity cut-off value in FIG. 20A, step 6 to ninety-seven percent results in 100% successful identification, while a higher cut-off at ninety-eight percent left several identification attempts as uncertain (FIG. 23A). Assuming the same rate of sequencing error, 2nd tier non-coding region barcodes exhibited greater differences between validation samples and database (FIG. 23B). Without DNA quality data, there was a reverse correlation between DNA concentration and the total number of mismatches and gaps of sequenced barcodes (FIG. 23C). Using the total number of mismatches and gaps as an indicator of discrimination power, 2nd tier non-coding region barcodes exhibited a higher discrimination power than 1st coding region barcodes, while the combined two-tiered barcoding strategy showed the highest discrimination power (FIG. 23D).

The disclosure is generally described herein using affirmative language to describe the numerous embodiments. The disclosure also includes embodiments in which subject matter is excluded, in full or in part, such as substances or materials, method steps and conditions, protocols, or procedures.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of authenticating sterilized chamomile material in a botanical dietary supplement, the method comprising:

isolating genomic DNA from a botanical dietary supplement comprising German chamomile, feverfew, Roman chamomile, and Chinese chamomile, wherein the geomic chamomile DNA isolated from the botanical dietary supplement comprises chamomile DNA fragments, wherein at least some of the chamomile DNA fragments are less than 220 base pairs, wherein the genomic chamomile DNA isolated from the botanical dietary supplement is degraded and undetectable using DNA barcoding, and wherein the chamomile DNA fragments are present in an amount of 1 pg to 1 ng;
ligating adapters to the chamomile DNA fragments to generate adapter-ligated DNA fragments;
amplifying the adapter-ligated DNA fragments using 8-12 cycles of polymerase chain reaction (PCR);
detecting the chamomile DNA fragments;
determining a size range of the chamomile DNA fragments;
hybridizing primers to a target nucleic acid sequence in the chamomile DNA fragments, wherein the primers comprise a species-specific primer set selected from:
a primer comprising a nucleic acid sequence as defined in SEQ ID NO: 1 and a primer comprising a nucleic acid sequence as defined in SEQ ID NO: 2;
a primer comprising a nucleic acid sequence as defined in SEQ ID NO: 3 and a primer comprising a nucleic acid sequence as defined in SEQ ID NO: 4;
a primer comprising a nucleic acid sequence as defined in SEQ ID NO: 5 and a primer comprising a nucleic acid sequence as defined in SEQ ID NO: 6; and
a primer comprising a nucleic acid sequence as defined in SEQ ID NO: 7 and a primer comprising a nucleic acid sequence as defined in SEQ ID NO: 8, and
amplifying the target nucleic acid sequence.

2. The method of claim 1, further comprising sequencing the target nucleic acid sequence.

3. The method of claim 1, wherein detecting the chamomile DNA fragments comprises running the amplified adapter-ligated DNA fragments on a gel for detection of the chamomile DNA fragments.

4. The method of claim 1, wherein the primers are designed on the basis of target species consensus sequence as PCR template and non-target consensus sequences as exclusion sequences.

5. The method of claim 1, further comprising detecting botanical adulteration in the botanical dietary sample.

6. The method of claim 1, wherein ligating is performed at 4° C. overnight.

7. The method of claim 1, further omprising evaluating total DNA after the amplifying the target nucleic acid sequence.

8. The method of claim 1, further comprising determining the sequence of the chamomile DNA fragments or determining the quantity or quality of the chamomile DNA fragments.

9. The method of claim 1, wherein the botanical dietary supplement is a processed botanical extract.

10. The method of claim 1, wherein the chamomile is *Matricaria chamomilla, Tanacetum parthenium* (feverfew), *Chamaemelum nobile* (*Anthemis nobilis* or Roman chamomile), *Chrysanthemum* x *morifolium* or *Chrysanthemum indicum* (Chinese chamomile).

11. A method of authenicating a processed botanical dietary supplement, the method comprising:
isolating genomic DNA from a processed botanical dietary supplement, wherein the genomic DNA isolated from the processed botanical dietary supplement comprises botanical DNA fragments, wherein at least some of the botanical DNA fragments are less than 220 base pairs, wherein the genomic DNA isolated from the processed botanical dietary supplement is degraded and undetectable using DNA barcoding, and wherein the botanical DNA fragments are present in an amount of 1 pg to 1 ng;
ligating adapters to the botanical DNA fragments to generate adapter-ligated DNA fragments;
amplifying the adapter-ligated DNA fragments using 8-12 cycles of polymerase chain reaction (PCR);
detecting the botanical DNA fragments;
determining a size range of the botanical DNA fragments;
designing primers according to the size range of the botanical DNA fragments;
hybridizing the primers to a target nucleic acid sequence in the botanical DNA fragments; and
amplifying the target nucleic acid sequence,
wherein the processed botanical dietary supplement comprises a botanical material comprising chamomile (*Matricaria chamomilla*), German chamomile (*Matricaria recutita*), feverfew (*Tanacetum parthenium*), Roman chamomile (*Chamaemelum nobile* syn *anthemis noblis*), Chineses chamomile (*Chrysanthemum* x *morifolium* or *Chrysanthemum indicum*), guarna (*Paullinia cupana*), parsley (*Petroselimum crispum*), celery (*Apium graveolens*), fennel (*Foeniculum vulgare*), Siberian ginseng (*Eleutherococcus senticosus*), Dong Quai (*Angelica sinensis*), garden angelica (*Angelica archangelica*), pubescent Angelica (*Angelica pubescens*), dahurain angelica (*Angelica dahurica*), Chinese cinnamon (*Cinnamomum cassia*), true cinnamon (*Cinnanamomum verum* syn *Cinnamomum zeylanicum*), Indonesian cinnamon (*Cinnamomum burmannii*), ginkgo (*Ginkgo biloba*), Japanese sophora (*Sophora japonica*), buckwheat (*Fagopyrum esculentum*), jujube (*Ziziphus spinosa*), Indian jujube (*Ziziphus mauritiana*), Japanese raisin tree (*Hovenia dulcis*), ginger (*Zingiber officinale*), lesser galangal (*Alpinia officinarum*), greater galangal (*Alpinia galanga*), schisandra (*Schisandra chinensis*), southern schisandra (*Schisandra sphenanthera*), astragalus (*Astragalus membranaceus*), maca (*Lepidium meyenii*), radish (*Raphanus sativus*), turnip (*Brassica rapa*), peppermint (*Mentha piperita*), Chinese mint (*Mentha canadensis*), green tea (*Camellia sinensis*), rosemary (*Rosmarinus officinalis*), bilberry (*Vaccinium myrtillus*), blueberry (*Vaccinium corymbosum*), cranberry (*Vaccinium macrocarpon*), mulberry (*Morus alba*), or guarana (*Paullinia cupana*).

12. The method of claim 11, further comprising sequencing the target nucleic acid sequence.

13. The method of claim 11, wherein detecting the botanical DNA fragments comprises running the amplified adapter-ligated DNA fragments on a gel for detection of the chamomile DNA fragments.

14. The method of claim 11, wherein the primers are designed on the basis of target species consensus sequence as PCR template and non-target consensus sequences as exclusion sequences.

15. The method of claim 11, further comprising detecting botanical adultaration in the processed botanical dietary supplement.

16. The methof claim 11, wherein ligating is performed at 4° C. overnight.

17. The method of claim 11, further comprising evaluating total DNA after the amplifying the target nucleic acid sequence.

18. The method of claim 11, wherein the processed botanical dietary supplement is a processed botanical extract.

* * * * *

UNITED STATES PATENT AND TRADEMARK OFFICE
CERTIFICATE OF CORRECTION

PATENT NO. : 11,873,535 B2
APPLICATION NO. : 16/048091
DATED : January 16, 2024
INVENTOR(S) : Zhengfei Lu It is certified that error appears in the above-identified patent and that said Letters Patent is hereby corrected as shown below:

On the Title Page

Column 2, Line 57, item (56) under Other Publications, delete "(May 25, 2016)," and insert --(May 26, 2016),--.

On Page 2, Column 1, Line 13, item (56) under Other Publications, delete "Intemati," and insert --International,--.

In the Specification

In Column 12, Line 9 (Approx.), delete "ginseng l" and insert --ginseng--.

In Column 27, Line 33 (Approx.), delete "AAAGGT" and insert --AAAGCT--.

In Column 28, Line 20, delete "calculations" and insert --calculations.--.

In the Claims

In Column 91, Claim 1, Line 66, delete "DNA" and insert --chamomile DNA--.

In Column 92, Claim 1, Line 63, delete "geomic" and insert --genomic--.

In Column 93, Claim 1, Line 26, delete "NO: 8," and insert --NO: 8;--.

In Column 93, Claim 5, Line 39, delete "sample." and insert --supplement.--.

In Column 93, Claim 7, Line 42, delete "omprising" and insert --comprising--.

In Column 93, Claim 10, Line 54, delete "morifolium" and insert --morifolium,--.

Signed and Sealed this
Ninth Day of April, 2024

Katherine Kelly Vidal
*Director of the United States Patent and Trademark Office*

CERTIFICATE OF CORRECTION (continued)
U.S. Pat. No. 11,873,535 B2

In Column 93, Claim 11, Line 56, delete "authenicating" and insert --authenticating--.

In Column 94, Claim 11, Lines 17-18 (Approx.), delete "noblis), Chineses" and insert --nobilis), Chinese--.

In Column 94, Claim 11, Line 19, delete "guarna" and insert --guarana--.

In Column 94, Claim 11, Line 20, delete "(Petroselimum" and insert --(Petroselinum--.

In Column 94, Claim 11, Line 25, delete "dahurain" and insert --dahurian--.

In Column 94, Claim 11, Lines 26-27, delete "(Cinnanamomum" and insert --(Cinnamomum--.

In Column 94, Claim 15, Line 56 (Approx.), delete "adultaration" and insert --adulteration--.

In Column 94, Claim 16, Line 58 (Approx.), delete "methof" and insert --method of--.

SEQUENCE LISTING

<160> NUMBER OF SEQ ID NOS: 152

<210> SEQ ID NO 1
<211> LENGTH: 21
<212> TYPE: DNA
<213> ORGANISM: Artificial Sequence
<220> FEATURE:
<223> OTHER INFORMATION: GC Forward

<400> SEQUENCE: 1
gtcgtcggtc gcaaggataa g                                    21

<210> SEQ ID NO 2
<211> LENGTH: 20
<212> TYPE: DNA
<213> ORGANISM: Artificial Sequence
<220> FEATURE:
<223> OTHER INFORMATION: GC Reverse

<400> SEQUENCE: 2
taaactcagc gggtagtccc                                      20

<210> SEQ ID NO 3
<211> LENGTH: 20
<212> TYPE: DNA
<213> ORGANISM: Artificial Sequence
<220> FEATURE:
<223> OTHER INFORMATION: F Forward

<400> SEQUENCE: 3
ggatattggt ctcccgtgct                                      20

<210> SEQ ID NO 4
<211> LENGTH: 24
<212> TYPE: DNA
<213> ORGANISM: Artificial Sequence
<220> FEATURE:
<223> OTHER INFORMATION: F Reverse

```
<400> SEQUENCE: 4
agagtttttc cttgcgacta acac                                    24

<210> SEQ ID NO 5
<211> LENGTH: 22
<212> TYPE: DNA
<213> ORGANISM: Artificial Sequence
<220> FEATURE:
<223> OTHER INFORMATION: RC Forward

<400> SEQUENCE: 5
tgtcgcacgt tgctaggaag ca                                      22

<210> SEQ ID NO 6
<211> LENGTH: 20
<212> TYPE: DNA
<213> ORGANISM: Artificial Sequence
<220> FEATURE:
<223> OTHER INFORMATION: RC Reverse

<400> SEQUENCE: 6
taaactcagc gggtagtccc                                         20

<210> SEQ ID NO 7
<211> LENGTH: 20
<212> TYPE: DNA
<213> ORGANISM: Artificial Sequence
<220> FEATURE:
<223> OTHER INFORMATION: CC Forward

<400> SEQUENCE: 7
gtcgaagcgt cgtcaagaga                                         20

<210> SEQ ID NO 8
<211> LENGTH: 20
<212> TYPE: DNA
<213> ORGANISM: Artificial Sequence
<220> FEATURE:
<223> OTHER INFORMATION: CC Reverse

<400> SEQUENCE: 8
tttgtttcgt gctgtgctcg                                         20

<210> SEQ ID NO 9
<211> LENGTH: 20
<212> TYPE: DNA
<213> ORGANISM: Artificial Sequence
<220> FEATURE:
<223> OTHER INFORMATION: P5 Forward

<400> SEQUENCE: 9
aatgatacgg cgaccaccga                                         20

<210> SEQ ID NO 10
<211> LENGTH: 21
<212> TYPE: DNA
<213> ORGANISM: Artificial Sequence
<220> FEATURE:
<223> OTHER INFORMATION: P7 Reverse

<400> SEQUENCE: 10
caagcagaag acggcatacg a                                       21

<210> SEQ ID NO 11
```

```
<211> LENGTH: 21
<212> TYPE: DNA
<213> ORGANISM: Artificial Sequence
<220> FEATURE:
<223> OTHER INFORMATION: Ginseng Forward

<400> SEQUENCE: 11
tcgagtcttt gaacgcaagt t                                               21

<210> SEQ ID NO 12
<211> LENGTH: 19
<212> TYPE: DNA
<213> ORGANISM: Artificial Sequence
<220> FEATURE:
<223> OTHER INFORMATION: Ginseng Reverse

<400> SEQUENCE: 12
gacacgggag gccattatc                                                  19

<210> SEQ ID NO 13
<211> LENGTH: 18
<212> TYPE: DNA
<213> ORGANISM: Artificial Sequence
<220> FEATURE:
<223> OTHER INFORMATION: Cinnamomum1 Forward

<400> SEQUENCE: 13
ggagcggaga ctggccgt                                                   18

<210> SEQ ID NO 14
<211> LENGTH: 21
<212> TYPE: DNA
<213> ORGANISM: Artificial Sequence
<220> FEATURE:
<223> OTHER INFORMATION: Cinnamomum1 Reverse

<400> SEQUENCE: 14
gcacggtgtc ctcctttcct g                                               21

<210> SEQ ID NO 15
<211> LENGTH: 17
<212> TYPE: DNA
<213> ORGANISM: Artificial Sequence
<220> FEATURE:
<223> OTHER INFORMATION: Cinnamomum2 Forward

<400> SEQUENCE: 15
cccgtcgccg atcgtac                                                    17

<210> SEQ ID NO 16
<211> LENGTH: 18
<212> TYPE: DNA
<213> ORGANISM: Artificial Sequence
<220> FEATURE:
<223> OTHER INFORMATION: Cinnamomum2 Reverse

<400> SEQUENCE: 16
ctgcgggcgg gtatggtc                                                   18

<210> SEQ ID NO 17
<211> LENGTH: 20
<212> TYPE: DNA
<213> ORGANISM: Artificial Sequence
<220> FEATURE:
<223> OTHER INFORMATION: Parsley Forward

<400> SEQUENCE: 17
```

```
tttgggcgga aattggcctc                                               20

<210> SEQ ID NO 18
<211> LENGTH: 22
<212> TYPE: DNA
<213> ORGANISM: Artificial Sequence
<220> FEATURE:
<223> OTHER INFORMATION: Parsley Reverse

<400> SEQUENCE: 18
ttacaaccac cgatgtcacg ac                                            22

<210> SEQ ID NO 19
<211> LENGTH: 20
<212> TYPE: DNA
<213> ORGANISM: Artificial Sequence
<220> FEATURE:
<223> OTHER INFORMATION: Ginkgo Forward

<400> SEQUENCE: 19
cgagtaactc ctcaacctgg                                               20

<210> SEQ ID NO 20
<211> LENGTH: 23
<212> TYPE: DNA
<213> ORGANISM: Artificial Sequence
<220> FEATURE:
<223> OTHER INFORMATION: Ginkgo Reverse

<400> SEQUENCE: 20
ttgtaacgat caagactggt aag                                           23

<210> SEQ ID NO 21
<211> LENGTH: 20
<212> TYPE: DNA
<213> ORGANISM: Artificial Sequence
<220> FEATURE:
<223> OTHER INFORMATION: TangKuei1 Forward

<400> SEQUENCE: 21
aataccctcw tgtcttgtcg                                               20

<210> SEQ ID NO 22
<211> LENGTH: 20
<212> TYPE: DNA
<213> ORGANISM: Artificial Sequence
<220> FEATURE:
<223> OTHER INFORMATION: TangKuei1 Reverse

<400> SEQUENCE: 22
tgcttaaact cagcgggtag                                               20

<210> SEQ ID NO 23
<211> LENGTH: 20
<212> TYPE: DNA
<213> ORGANISM: Artificial Sequence
<220> FEATURE:
<223> OTHER INFORMATION: TangKuei2 Forward

<400> SEQUENCE: 23
ggacttacca gccttgatcg                                               20

<210> SEQ ID NO 24
<211> LENGTH: 23
<212> TYPE: DNA
```

```
<213> ORGANISM: Artificial Sequence
<220> FEATURE:
<223> OTHER INFORMATION: TangKuei2 Reverse

<400> SEQUENCE: 24
tcaaaaaggt ctaatgggta agc                                            23

<210> SEQ ID NO 25
<211> LENGTH: 26
<212> TYPE: DNA
<213> ORGANISM: Artificial Sequence
<220> FEATURE:
<223> OTHER INFORMATION: Astragalus1 Forward

<400> SEQUENCE: 25
tgaagaaggt tctgttacta acatgt                                         26

<210> SEQ ID NO 26
<211> LENGTH: 22
<212> TYPE: DNA
<213> ORGANISM: Artificial Sequence
<220> FEATURE:
<223> OTHER INFORMATION: Astragalus1 Reverse

<400> SEQUENCE: 26
cgggccttgg aaagttttaa ca                                             22

<210> SEQ ID NO 27
<211> LENGTH: 18
<212> TYPE: DNA
<213> ORGANISM: Artificial Sequence
<220> FEATURE:
<223> OTHER INFORMATION: Jujube1 Forward

<400> SEQUENCE: 27
gtcacacaac gttgcccc                                                  18

<210> SEQ ID NO 28
<211> LENGTH: 16
<212> TYPE: DNA
<213> ORGANISM: Artificial Sequence
<220> FEATURE:
<223> OTHER INFORMATION: Jujube1 Reverse

<400> SEQUENCE: 28
cacgggaggc cagcat                                                    16

<210> SEQ ID NO 29
<211> LENGTH: 21
<212> TYPE: DNA
<213> ORGANISM: Artificial Sequence
<220> FEATURE:
<223> OTHER INFORMATION: Schisandra1 Forward

<400> SEQUENCE: 29
tcgagttttt gaacgcaagt t                                              21

<210> SEQ ID NO 30
<211> LENGTH: 20
<212> TYPE: DNA
<213> ORGANISM: Artificial Sequence
<220> FEATURE:
<223> OTHER INFORMATION: Schisandra1 Reverse

<400> SEQUENCE: 30
tcctcgcaaa caccatacac                                                20
```

<210> SEQ ID NO 31
<211> LENGTH: 20
<212> TYPE: DNA
<213> ORGANISM: Artificial Sequence
<220> FEATURE:
<223> OTHER INFORMATION: Schisandra2 Forward

<400> SEQUENCE: 31
atccttgtga tgccgaaaac                                         20

<210> SEQ ID NO 32
<211> LENGTH: 20
<212> TYPE: DNA
<213> ORGANISM: Artificial Sequence
<220> FEATURE:
<223> OTHER INFORMATION: Schisandra2 Reverse

<400> SEQUENCE: 32
atcaacgcat ggcacaagac                                         20

<210> SEQ ID NO 33
<211> LENGTH: 27
<212> TYPE: DNA
<213> ORGANISM: Artificial Sequence
<220> FEATURE:
<223> OTHER INFORMATION: Schisandra3 Forward

<400> SEQUENCE: 33
gaaattggtt attgtattgt ttcttca                                 27

<210> SEQ ID NO 34
<211> LENGTH: 22
<212> TYPE: DNA
<213> ORGANISM: Artificial Sequence
<220> FEATURE:
<223> OTHER INFORMATION: Schisandra3 Reverse

<400> SEQUENCE: 34
tcactggaat aaatgtcgat gc                                      22

<210> SEQ ID NO 35
<211> LENGTH: 27
<212> TYPE: DNA
<213> ORGANISM: Artificial Sequence
<220> FEATURE:
<223> OTHER INFORMATION: Schisandra4 Forward

<400> SEQUENCE: 35
tctagctctc tgtatgaaat gactaaa                                 27

<210> SEQ ID NO 36
<211> LENGTH: 19
<212> TYPE: DNA
<213> ORGANISM: Artificial Sequence
<220> FEATURE:
<223> OTHER INFORMATION: Schisandra4 Reverse

<400> SEQUENCE: 36
atccgcccct cctctctat                                          19

<210> SEQ ID NO 37
<211> LENGTH: 20
<212> TYPE: DNA
<213> ORGANISM: Artificial Sequence
<220> FEATURE:

<223> OTHER INFORMATION: Ginger1 Forward

<400> SEQUENCE: 37
cgatcggcac taaggaacaa                                          20

<210> SEQ ID NO 38
<211> LENGTH: 21
<212> TYPE: DNA
<213> ORGANISM: Artificial Sequence
<220> FEATURE:
<223> OTHER INFORMATION: Ginger1 Reverse

<400> SEQUENCE: 38
cgagatatcc attgccgaga g                                        21

<210> SEQ ID NO 39
<211> LENGTH: 21
<212> TYPE: DNA
<213> ORGANISM: Artificial Sequence
<220> FEATURE:
<223> OTHER INFORMATION: Ginger2 Forward

<400> SEQUENCE: 39
agcattccga gtaactcctc a                                        21

<210> SEQ ID NO 40
<211> LENGTH: 20
<212> TYPE: DNA
<213> ORGANISM: Artificial Sequence
<220> FEATURE:
<223> OTHER INFORMATION: Ginger2 Reverse

<400> SEQUENCE: 40
agtccatcag tccacacagt                                          20

<210> SEQ ID NO 41
<211> LENGTH: 21
<212> TYPE: DNA
<213> ORGANISM: Artificial Sequence
<220> FEATURE:
<223> OTHER INFORMATION: Ginger3 Forward

<400> SEQUENCE: 41
tgaactcaca accatatgcg t                                        21

<210> SEQ ID NO 42
<211> LENGTH: 21
<212> TYPE: DNA
<213> ORGANISM: Artificial Sequence
<220> FEATURE:
<223> OTHER INFORMATION: Ginger3 Reverse

<400> SEQUENCE: 42
ttcttcacat gtacctgcag t                                        21

<210> SEQ ID NO 43
<211> LENGTH: 23
<212> TYPE: DNA
<213> ORGANISM: Artificial Sequence
<220> FEATURE:
<223> OTHER INFORMATION: Ginger4 Forward

<400> SEQUENCE: 43
tgaactcaca accatttatg cgt                                      23

```
<210> SEQ ID NO 44
<211> LENGTH: 21
<212> TYPE: DNA
<213> ORGANISM: Artificial Sequence
<220> FEATURE:
<223> OTHER INFORMATION: Ginger4 Reverse

<400> SEQUENCE: 44
ttcttcacat gtacctgcag t                                              21

<210> SEQ ID NO 45
<211> LENGTH: 18
<212> TYPE: DNA
<213> ORGANISM: Artificial Sequence
<220> FEATURE:
<223> OTHER INFORMATION: Maca Forward

<400> SEQUENCE: 45
ctgggcgtca caaatcgt                                                  18

<210> SEQ ID NO 46
<211> LENGTH: 20
<212> TYPE: DNA
<213> ORGANISM: Artificial Sequence
<220> FEATURE:
<223> OTHER INFORMATION: Maca4 Reverse

<400> SEQUENCE: 46
ggtaacacac gggagaccag                                                20

<210> SEQ ID NO 47
<211> LENGTH: 18
<212> TYPE: DNA
<213> ORGANISM: Artificial Sequence
<220> FEATURE:
<223> OTHER INFORMATION: Jujube1 Forward

<400> SEQUENCE: 47
gtcacacaac gttgcccc                                                  18

<210> SEQ ID NO 48
<211> LENGTH: 16
<212> TYPE: DNA
<213> ORGANISM: Artificial Sequence
<220> FEATURE:
<223> OTHER INFORMATION: Jujube1 Reverse

<400> SEQUENCE: 48
cacgggaggc cagcat                                                    16

<210> SEQ ID NO 49
<211> LENGTH: 20
<212> TYPE: DNA
<213> ORGANISM: Artificial Sequence
<220> FEATURE:
<223> OTHER INFORMATION: Chamomile Ginger4 Forward

<400> SEQUENCE: 49
ggtggtcgta aaaccctcg                                                 20

<210> SEQ ID NO 50
<211> LENGTH: 21
<212> TYPE: DNA
<213> ORGANISM: Artificial Sequence
<220> FEATURE:
<223> OTHER INFORMATION: Chamomile Ginger4 Reverse
```

<400> SEQUENCE: 50
tgcttaaact cagcgggtag t                                              21

<210> SEQ ID NO 51
<211> LENGTH: 20
<212> TYPE: DNA
<213> ORGANISM: Artificial Sequence
<220> FEATURE:
<223> OTHER INFORMATION: Tea ITS2

<400> SEQUENCE: 51
agccattagg ttgagggcac                                                20

<210> SEQ ID NO 52
<211> LENGTH: 17
<212> TYPE: DNA
<213> ORGANISM: Artificial Sequence
<220> FEATURE:
<223> OTHER INFORMATION: Tea ITS2

<400> SEQUENCE: 52
cgcagcccct tcttcccc                                                  17

<210> SEQ ID NO 53
<211> LENGTH: 20
<212> TYPE: DNA
<213> ORGANISM: Artificial Sequence
<220> FEATURE:
<223> OTHER INFORMATION: Tea ITS2

<400> SEQUENCE: 53
aattgcagaa tcccgcgaac                                                20

<210> SEQ ID NO 54
<211> LENGTH: 18
<212> TYPE: DNA
<213> ORGANISM: Artificial Sequence
<220> FEATURE:
<223> OTHER INFORMATION: Tea ITS2

<400> SEQUENCE: 54
caacgtgaga cgcccagg                                                  18

<210> SEQ ID NO 55
<211> LENGTH: 17
<212> TYPE: DNA
<213> ORGANISM: Artificial Sequence
<220> FEATURE:
<223> OTHER INFORMATION: Tea ITS2

<400> SEQUENCE: 55
ggaagaaggg ctgcggg                                                   17

<210> SEQ ID NO 56
<211> LENGTH: 20
<212> TYPE: DNA
<213> ORGANISM: Artificial Sequence
<220> FEATURE:
<223> OTHER INFORMATION: Tea ITS2

<400> SEQUENCE: 56
acggtttgtc aaccaccact                                                20

<210> SEQ ID NO 57
<211> LENGTH: 18

```
<212> TYPE: DNA
<213> ORGANISM: Artificial Sequence
<220> FEATURE:
<223> OTHER INFORMATION: Tea ITS2

<400> SEQUENCE: 57
tcggcccaaa agcgagtc                                                  18

<210> SEQ ID NO 58
<211> LENGTH: 19
<212> TYPE: DNA
<213> ORGANISM: Artificial Sequence
<220> FEATURE:
<223> OTHER INFORMATION: Tea ITS2

<400> SEQUENCE: 58
cgatagggtc acgacaggc                                                 19

<210> SEQ ID NO 59
<211> LENGTH: 20
<212> TYPE: DNA
<213> ORGANISM: Artificial Sequence
<220> FEATURE:
<223> OTHER INFORMATION: Tea ITS2

<400> SEQUENCE: 59
aggcctgtcg tgaccctatc                                                20

<210> SEQ ID NO 60
<211> LENGTH: 22
<212> TYPE: DNA
<213> ORGANISM: Artificial Sequence
<220> FEATURE:
<223> OTHER INFORMATION: Tea ITS2

<400> SEQUENCE: 60
tcctccgctt attgatatgc tt                                             22

<210> SEQ ID NO 61
<211> LENGTH: 20
<212> TYPE: DNA
<213> ORGANISM: Artificial Sequence
<220> FEATURE:
<223> OTHER INFORMATION: Tea ITS2

<400> SEQUENCE: 61
gggattaccc gctgagttta                                                20

<210> SEQ ID NO 62
<211> LENGTH: 20
<212> TYPE: DNA
<213> ORGANISM: Artificial Sequence
<220> FEATURE:
<223> OTHER INFORMATION: Tea ITS2

<400> SEQUENCE: 62
gtcgctcgat tttcaagctg                                                20

<210> SEQ ID NO 63
<211> LENGTH: 20
<212> TYPE: DNA
<213> ORGANISM: Artificial Sequence
<220> FEATURE:
<223> OTHER INFORMATION: Tea rbcL

<400> SEQUENCE: 63
```
tgttggattc aaagctggtg                                           20

<210> SEQ ID NO 64
<211> LENGTH: 20
<212> TYPE: DNA
<213> ORGANISM: Artificial Sequence
<220> FEATURE:
<223> OTHER INFORMATION: Tea rbcL

<400> SEQUENCE: 64
cggagttact cggaatgctg                                           20

<210> SEQ ID NO 65
<211> LENGTH: 21
<212> TYPE: DNA
<213> ORGANISM: Artificial Sequence
<220> FEATURE:
<223> OTHER INFORMATION: Tea rbcL

<400> SEQUENCE: 65
ctgatatctt ggcagcattc c                                         21

<210> SEQ ID NO 66
<211> LENGTH: 24
<212> TYPE: DNA
<213> ORGANISM: Artificial Sequence
<220> FEATURE:
<223> OTHER INFORMATION: Tea rbcL

<400> SEQUENCE: 66
gtccatgtac cagtagaaga ttcg                                      24

<210> SEQ ID NO 67
<211> LENGTH: 20
<212> TYPE: DNA
<213> ORGANISM: Artificial Sequence
<220> FEATURE:
<223> OTHER INFORMATION: Tea rbcL

<400> SEQUENCE: 67
gagtaactcc gcaacctgga                                           20

<210> SEQ ID NO 68
<211> LENGTH: 20
<212> TYPE: DNA
<213> ORGANISM: Artificial Sequence
<220> FEATURE:
<223> OTHER INFORMATION: Tea rbcL

<400> SEQUENCE: 68
atcgcccttt gtaacgatca                                           20

<210> SEQ ID NO 69
<211> LENGTH: 20
<212> TYPE: DNA
<213> ORGANISM: Artificial Sequence
<220> FEATURE:
<223> OTHER INFORMATION: Tea rbcL

<400> SEQUENCE: 69
gctgccgaat cttctactgg                                           20

<210> SEQ ID NO 70
<211> LENGTH: 21
<212> TYPE: DNA
<213> ORGANISM: Artificial Sequence
<220> FEATURE:
<223> OTHER INFORMATION: Tea rbcL

<400> SEQUENCE: 70
tgactttctt ctccagcaac g                                         21

<210> SEQ ID NO 71
<211> LENGTH: 20
<212> TYPE: DNA
<213> ORGANISM: Artificial Sequence
<220> FEATURE:
<223> OTHER INFORMATION: Tea rbcL

<400> SEQUENCE: 71
actgtgtgga ccgatggact                                           20

<210> SEQ ID NO 72
<211> LENGTH: 24
<212> TYPE: DNA
<213> ORGANISM: Artificial Sequence
<220> FEATURE:
<223> OTHER INFORMATION: Tea rbcL

<400> SEQUENCE: 72
ttcaaaaagg tctaaaggat acgc                                      24

<210> SEQ ID NO 73
<211> LENGTH: 20
<212> TYPE: DNA
<213> ORGANISM: Artificial Sequence
<220> FEATURE:
<223> OTHER INFORMATION: Tea rbcL

<400> SEQUENCE: 73
ccgttgctgg agaagaaagt                                           20

<210> SEQ ID NO 74
<211> LENGTH: 20
<212> TYPE: DNA
<213> ORGANISM: Artificial Sequence
<220> FEATURE:
<223> OTHER INFORMATION: Tea rbcL

<400> SEQUENCE: 74
cagggctttg aacccaaata                                           20

<210> SEQ ID NO 75
<211> LENGTH: 24
<212> TYPE: DNA
<213> ORGANISM: Artificial Sequence
<220> FEATURE:
<223> OTHER INFORMATION: Tea rbcL

<400> SEQUENCE: 75
gcgtatcctt tagacctttt tgaa                                      24

<210> SEQ ID NO 76
<211> LENGTH: 20
<212> TYPE: DNA
<213> ORGANISM: Artificial Sequence
<220> FEATURE:
<223> OTHER INFORMATION: Tea rbcL

<400> SEQUENCE: 76
attcgcagat cttccagacg                                           20

<210> SEQ ID NO 77
<211> LENGTH: 23
<212> TYPE: DNA
<213> ORGANISM: Artificial Sequence
<220> FEATURE:
<223> OTHER INFORMATION: Tea rbcL

<400> SEQUENCE: 77
tccattgtgg gtaatgtatt tgg                                    23

<210> SEQ ID NO 78
<211> LENGTH: 20
<212> TYPE: DNA
<213> ORGANISM: Artificial Sequence
<220> FEATURE:
<223> OTHER INFORMATION: Tea rbcL

<400> SEQUENCE: 78
tttcaacttg gatgccatga                                        20

<210> SEQ ID NO 79
<211> LENGTH: 20
<212> TYPE: DNA
<213> ORGANISM: Artificial Sequence
<220> FEATURE:
<223> OTHER INFORMATION: Tea rbcL

<400> SEQUENCE: 79
tctggaagat ctgcgaatcc                                        20

<210> SEQ ID NO 80
<211> LENGTH: 20
<212> TYPE: DNA
<213> ORGANISM: Artificial Sequence
<220> FEATURE:
<223> OTHER INFORMATION: Tea rbcL

<400> SEQUENCE: 80
caggggacga ccatacttgt                                        20

<210> SEQ ID NO 81
<211> LENGTH: 20
<212> TYPE: DNA
<213> ORGANISM: Artificial Sequence
<220> FEATURE:
<223> OTHER INFORMATION: Tea rbcL

<400> SEQUENCE: 81
cgcctcatgg catccaagtt                                        20

<210> SEQ ID NO 82
<211> LENGTH: 21
<212> TYPE: DNA
<213> ORGANISM: Artificial Sequence
<220> FEATURE:
<223> OTHER INFORMATION: Tea rbcL

<400> SEQUENCE: 82
ccaccgcgga gacattcata a                                      21

<210> SEQ ID NO 83
<211> LENGTH: 29
<212> TYPE: DNA
<213> ORGANISM: Cinnamomum aromaticum

<400> SEQUENCE: 83

```
ccgtgcccgg gtgaccggcg cgcggtcgg                                    29

<210> SEQ ID NO 84
<211> LENGTH: 29
<212> TYPE: DNA
<213> ORGANISM: Cinnamomum burmannii

<400> SEQUENCE: 84
ccgtgcccga gcgatcggcg cgcggtcgg                                    29

<210> SEQ ID NO 85
<211> LENGTH: 29
<212> TYPE: DNA
<213> ORGANISM: Cinnamomum verum

<400> SEQUENCE: 85
ccgtgcccgg gtcatcggcg cgcggtcgg                                    29

<210> SEQ ID NO 86
<211> LENGTH: 38
<212> TYPE: DNA
<213> ORGANISM: Cinnamomum aromaticum

<400> SEQUENCE: 86
gtcgcgcccg caatccgccg cgcggtgcaa gcccgtgg                           38

<210> SEQ ID NO 87
<211> LENGTH: 37
<212> TYPE: DNA
<213> ORGANISM: Cinnamomum burmannii

<400> SEQUENCE: 87
gtcgcgcccg caatccgccg cgcggtgcca cccgtgg                            37

<210> SEQ ID NO 88
<211> LENGTH: 37
<212> TYPE: DNA
<213> ORGANISM: Cinnamomum verum

<400> SEQUENCE: 88
gcagcgcccg cattccgccg cgcggtgccg cccgtgg                            37

<210> SEQ ID NO 89
<211> LENGTH: 101
<212> TYPE: DNA
<213> ORGANISM: Panax quinquefolius

<400> SEQUENCE: 89
gcgcccgaag ccattaggcc gagggcacgt ctgcctgggc gtcacgcatc gcgtcgcccc    60
ccaacccatc actcctttgc gggagtcgag gcggaggggc g                      101

<210> SEQ ID NO 90
<211> LENGTH: 101
<212> TYPE: DNA
<213> ORGANISM: Panax ginseng

<400> SEQUENCE: 90
gcgcccgaag ccattaggcc gagggcacgt ctgcctgggc gtcacgcatc gcgtcgcccc    60
ccaacccatc actcccttgc gggagttgag gcggaggggc g                      101

<210> SEQ ID NO 91
```

```
<211> LENGTH: 101
<212> TYPE: DNA
<213> ORGANISM: Eleutherococcus senticosus

<400> SEQUENCE: 91
gcgcccgaag ccattaggcc gagggcacgt ctgcctgggc gtcacgcatc gcgtcgcccc      60
ccaaccctgc actccctcat gggagtcatg actgaggggc g                        101

<210> SEQ ID NO 92
<211> LENGTH: 101
<212> TYPE: DNA
<213> ORGANISM: Panax notoginseng

<400> SEQUENCE: 92
gcgcccgaag ccattaggcc gagggcacgt ctgcctgggc gtcacgcatc gcgtcgcccc      60
ccaacccatc attccctcgc gggagtcgat gcggaggggc g                        101

<210> SEQ ID NO 93
<211> LENGTH: 49
<212> TYPE: DNA
<213> ORGANISM: Petroselinum crispum

<400> SEQUENCE: 93
ccgtgccttg ctgcgcggct ggtgcaaaag tgagtctccg acgacggac                 49

<210> SEQ ID NO 94
<211> LENGTH: 49
<212> TYPE: DNA
<213> ORGANISM: Foeniculum vulgare

<400> SEQUENCE: 94
ccgtgccttg ttgtgcggct ggtgcaaaag cgagtctctg gcggtggac                 49

<210> SEQ ID NO 95
<211> LENGTH: 49
<212> TYPE: DNA
<213> ORGANISM: Apium graveolens

<400> SEQUENCE: 95
ccgtgccgtg ttgtgcggtt ggcgcaaaag cgagtctccg gcgacggac                 49

<210> SEQ ID NO 96
<211> LENGTH: 79
<212> TYPE: DNA
<213> ORGANISM: Ginkgo biloba

<400> SEQUENCE: 96
agtgccacct gaggaagcgg gagctgcagt agctgccgaa tcttccactg gtacatggac      60
cactgtttgg accgatgga                                                 79

<210> SEQ ID NO 97
<211> LENGTH: 79
<212> TYPE: DNA
<213> ORGANISM: Sophora japonica

<400> SEQUENCE: 97
agttccgcct gaagaagcag gtgccgcggt agctgctgaa tcttctactg gtacatggac      60
aactgtgtgg accgatggg                                                 79

<210> SEQ ID NO 98
<211> LENGTH: 79
```

```
<212> TYPE: DNA
<213> ORGANISM: Fagopyrum esculentum

<400> SEQUENCE: 98
agttccacca gaagaagcag gggccgcggt agctgccgaa tcttctactg gtacatggac    60
aactgtgtgg accgatgga                                                 79

<210> SEQ ID NO 99
<211> LENGTH: 83
<212> TYPE: DNA
<213> ORGANISM: Zingiber officinale

<400> SEQUENCE: 99
cgaactcgga agcggagggc ccctcgccgt gcgcagggga gcccgatgcg tcggagattc    60
ctcggaatca atcaatcaaa cga                                            83

<210> SEQ ID NO 100
<211> LENGTH: 83
<212> TYPE: DNA
<213> ORGANISM: Zingiber officinale

<400> SEQUENCE: 100
cgaactcgga agcggagggc ccctcgccgt gcgcagggga gcccgatgcg tcggagattc    60
ctcggaatca atcaatcaaa cga                                            83

<210> SEQ ID NO 101
<211> LENGTH: 87
<212> TYPE: DNA
<213> ORGANISM: Zingiber officinale

<400> SEQUENCE: 101
cgaactcgga agcggagggc ccctcgccgt gcgcagggga gcccgatgcg tcggagattc    60
ctcggaatca atcaatcaat caaacga                                        87

<210> SEQ ID NO 102
<211> LENGTH: 87
<212> TYPE: DNA
<213> ORGANISM: Zingiber officinale

<400> SEQUENCE: 102
cgaactcgga agcggagggc ccctcgccgt gcgcagggga gcccgatgcg tcggagattc    60
ctcggaatca atcaatcaat caaacga                                        87

<210> SEQ ID NO 103
<211> LENGTH: 72
<212> TYPE: DNA
<213> ORGANISM: Alpinia officinarum

<400> SEQUENCE: 103
tgaactcaga agcagatggc cctcagtgtg ctcggggagg ccaatgcatc ggagatgcct    60
caaatcaaat ga                                                        72

<210> SEQ ID NO 104
<211> LENGTH: 72
<212> TYPE: DNA
<213> ORGANISM: Alpinia officinarum

<400> SEQUENCE: 104
tgaactcaga agcagatggc cctcagcgtg ctcggggagg ccaatgcacc ggagatgcct    60
```
caaatcaaat ga                                                          72

<210> SEQ ID NO 105
<211> LENGTH: 72
<212> TYPE: DNA
<213> ORGANISM: Alpinia officinarum

<400> SEQUENCE: 105
tgaactcaga agcagatggc cctcagcgtg ctcggggagg ccaatgcatc ggagatgcct      60
caaatcaaat ga                                                          72

<210> SEQ ID NO 106
<211> LENGTH: 73
<212> TYPE: DNA
<213> ORGANISM: Alpinia galanga

<400> SEQUENCE: 106
taaactgaga agcaaagggc cctcggtgtg tgcggggagc ccaatgcgtc ggagaagcct      60
cgaaatcaaa tga                                                         73

<210> SEQ ID NO 107
<211> LENGTH: 73
<212> TYPE: DNA
<213> ORGANISM: Alpinia galanga

<400> SEQUENCE: 107
taaactgaga agcaaagggc cctcgctgtg tgcggggagc ccaatgcgtc ggagaagcct      60
cgaaatcaaa tga                                                         73

<210> SEQ ID NO 108
<211> LENGTH: 73
<212> TYPE: DNA
<213> ORGANISM: Alpinia galanga

<400> SEQUENCE: 108
taaactgaga agcaaagggc cctcgctgtg tgcggggagc ccaatgcgtc ggagaagctt      60
cgaaatcaaa tga                                                         73

<210> SEQ ID NO 109
<211> LENGTH: 67
<212> TYPE: DNA
<213> ORGANISM: Zingiber officinale

<400> SEQUENCE: 109
acctggagtt ccacccgaag aagcaggggc tgcggtagct gccgaatctt ctactggtac      60
atggaca                                                                67

<210> SEQ ID NO 110
<211> LENGTH: 67
<212> TYPE: DNA
<213> ORGANISM: Alpinia officinarum

<400> SEQUENCE: 110
acctggagtt ccacccgaag aagcaggggc tgcggtagca gccgaatcct ctactggtac      60
atggaca                                                                67

<210> SEQ ID NO 111
<211> LENGTH: 67
<212> TYPE: DNA
<213> ORGANISM: Alpinia galanga

```
<400> SEQUENCE: 111
acctggagtt ccacccgaag aagcaggagc tgcggtagca gccgaatcct ctactggtac    60
atggaca                                                              67

<210> SEQ ID NO 112
<211> LENGTH: 87
<212> TYPE: DNA
<213> ORGANISM: Zingiber officinale

<400> SEQUENCE: 112
tggagagacc gtttcctatt ttgtgctgaa gcacttttta aagcgcaggc cgaaacaggt    60
gaaattaaag gacattactt gaatgct                                        87

<210> SEQ ID NO 113
<211> LENGTH: 87
<212> TYPE: DNA
<213> ORGANISM: Alpinia officinarum

<400> SEQUENCE: 113
tggagagacc gtttcgtatt ttgtgctgaa gcactttata aagcgcaggc cgaaacaggt    60
gaaattaaag ggcattactt gaatgct                                        87

<210> SEQ ID NO 114
<211> LENGTH: 87
<212> TYPE: DNA
<213> ORGANISM: Alpinia galanga

<400> SEQUENCE: 114
tggagagacc gtttcgtatt ttgtgctgaa gcaatttata aagcgcaggc cgaaacaggt    60
gaaattaaag ggcattactt taatgct                                        87

<210> SEQ ID NO 115
<211> LENGTH: 37
<212> TYPE: DNA
<213> ORGANISM: Ziziphus jujuba var spinosa

<400> SEQUENCE: 115
ccatcccaac ctcgacctcg aggcgaagag ggggcgg                             37

<210> SEQ ID NO 116
<211> LENGTH: 31
<212> TYPE: DNA
<213> ORGANISM: Ziziphus jujuba var spinosa

<400> SEQUENCE: 116
ccatcccaac ctcgaggcga agaggggcg g                                    31

<210> SEQ ID NO 117
<211> LENGTH: 35
<212> TYPE: DNA
<213> ORGANISM: Ziziphus mauritiana

<400> SEQUENCE: 117
ccccaacctc cgcctcggaa gggaagaggg ggcgg                               35

<210> SEQ ID NO 118
<211> LENGTH: 34
<212> TYPE: DNA
<213> ORGANISM: Ziziphus mauritiana
```

```
<400> SEQUENCE: 118
cccaacctcc gcctcggaag ggaagagggg gcgg                                 34

<210> SEQ ID NO 119
<211> LENGTH: 34
<212> TYPE: DNA
<213> ORGANISM: Ziziphus mauritiana

<400> SEQUENCE: 119
cccaacctcc tcctcggaag ggaagagggg gcgg                                 34

<210> SEQ ID NO 120
<211> LENGTH: 29
<212> TYPE: DNA
<213> ORGANISM: Hovenia dulcis

<400> SEQUENCE: 120
cccaacctcg accccgaggg cgggtgggc                                       29

<210> SEQ ID NO 121
<211> LENGTH: 88
<212> TYPE: DNA
<213> ORGANISM: Angelica sinensis

<400> SEQUENCE: 121
cgcgaatccg cgtcatctta gtgagctcaa ggacccttag gcggcacaca ctttgtgcac     60
ttcgaatgtg accccaggtc aggcggga                                        88

<210> SEQ ID NO 122
<211> LENGTH: 88
<212> TYPE: DNA
<213> ORGANISM: Angelica sinensis

<400> SEQUENCE: 122
cgcgaatccg cgtcatctta gtgagctcaa ggacccttag gcggcacaca ctttgtgcac     60
ttcgaatgtg accccaggtc aggcggga                                        88

<210> SEQ ID NO 123
<211> LENGTH: 88
<212> TYPE: DNA
<213> ORGANISM: Angelica pubescentis

<400> SEQUENCE: 123
cgcgaatcct cgtcatctta gcgagctcca ggacccttag gtagcacata ctctgtgcgc     60
ttcgactgtg accccaggtc aggcggga                                        88

<210> SEQ ID NO 124
<211> LENGTH: 88
<212> TYPE: DNA
<213> ORGANISM: Angelica pubescentis

<400> SEQUENCE: 124
cgcgaatcct cgtcatctta gcgagctcca ggacccttag gtagcacata ctctgtgcgc     60
ttcgactgtg accccaggtc aggcggga                                        88

<210> SEQ ID NO 125
<211> LENGTH: 88
<212> TYPE: DNA
<213> ORGANISM: Angelica dahuricae

<400> SEQUENCE: 125
```
cgtgaatcct tgtcatctta gagagctcca ggacccttag gcagcacgta ctctgtgcgc    60
ttcgactgtg accccaggtc aggcggga                                      88

<210> SEQ ID NO 126
<211> LENGTH: 88
<212> TYPE: DNA
<213> ORGANISM: Angelica dahuricae

<400> SEQUENCE: 126
cgtgaatcct tgtcatctta gagagctcca ggacccttag gcagcacgta ctctgtgcgc    60
ttcgactgtg accccaggtc aggcggga                                      88

<210> SEQ ID NO 127
<211> LENGTH: 67
<212> TYPE: DNA
<213> ORGANISM: Angelica sinensis

<400> SEQUENCE: 127
ttacaaaggg cgctgctacg aaatcgagcc cgttgctgga gaagaaaatc aatatatcgc    60
ttatgta                                                             67

<210> SEQ ID NO 128
<211> LENGTH: 67
<212> TYPE: DNA
<213> ORGANISM: Angelica pubescentis

<400> SEQUENCE: 128
ttacaaaggg cgctgctacg gaatcgagcc cgttgctgga gaagaaaatc aatttatcgc    60
ttatgta                                                             67

<210> SEQ ID NO 129
<211> LENGTH: 67
<212> TYPE: DNA
<213> ORGANISM: Angelica dahuricae

<400> SEQUENCE: 129
ttacaaaggg cgctgctacg gaatcgagcc cgttgctgga gaagaaaatc aatttatcgc    60
ttatgta                                                             67

<210> SEQ ID NO 130
<211> LENGTH: 84
<212> TYPE: DNA
<213> ORGANISM: Schisandra chinensis

<400> SEQUENCE: 130
gcgcccgagg ccacctggcc aagggcacgc ctgcctgggc gtcacgcttt gcgacgctcc    60
cctccctccc attctccttt ttgg                                          84

<210> SEQ ID NO 131
<211> LENGTH: 84
<212> TYPE: DNA
<213> ORGANISM: Schisandra sphenanthera

<400> SEQUENCE: 131
gcgcccgagg ccacctggcc aagggcacgc ctgcctgggc gtcacgcttt gcgtcgctcc    60
cctccctccc attctccctt tttg                                          84

<210> SEQ ID NO 132

<210> SEQ ID NO 132
<211> LENGTH: 38
<212> TYPE: DNA
<213> ORGANISM: Schisandra chinensis

<400> SEQUENCE: 132
ccttcccctc tcattgctac cttgtatgac acgccttg                            38

<210> SEQ ID NO 133
<211> LENGTH: 38
<212> TYPE: DNA
<213> ORGANISM: Schisandra sphenanthera

<400> SEQUENCE: 133
ccttcccctc tcattgctac cttgtatgac atgctttg                            38

<210> SEQ ID NO 134
<211> LENGTH: 26
<212> TYPE: DNA
<213> ORGANISM: Schisandra chinensis

<400> SEQUENCE: 134
attgacaatt gagtagtgtt ttgttc                                         26

<210> SEQ ID NO 135
<211> LENGTH: 26
<212> TYPE: DNA
<213> ORGANISM: Schisandra sphenanthera

<400> SEQUENCE: 135
attgacaatt gagtagtgtt ttattc                                         26

<210> SEQ ID NO 136
<211> LENGTH: 43
<212> TYPE: DNA
<213> ORGANISM: Schisandra chinensis

<400> SEQUENCE: 136
tacaaaatac aaaattatga atagtcgaaa tggaatcttt tgg                      43

<210> SEQ ID NO 137
<211> LENGTH: 44
<212> TYPE: DNA
<213> ORGANISM: Schisandra sphenanthera

<400> SEQUENCE: 137
tacaaaataa aaaattttg aatagtcgaa atggaatctt tttg                      44

<210> SEQ ID NO 138
<211> LENGTH: 82
<212> TYPE: DNA
<213> ORGANISM: Astragalus membranaceus

<400> SEQUENCE: 138
ttacctccat tgttggtaat gtatttggat tcaaggcttt gcgcgctcta cgtttggagg    60
atttgcgaat ccctactgct ta                                             82

<210> SEQ ID NO 139
<211> LENGTH: 38
<212> TYPE: DNA
<213> ORGANISM: Lepidium meyenii

<400> SEQUENCE: 139
cgttcccctc acaaaatttt gcgagtgcgg gacggaag                            38

<210> SEQ ID NO 140
<211> LENGTH: 35
<212> TYPE: DNA
<213> ORGANISM: Raphanus sativus

<400> SEQUENCE: 140
cgtcccccca tcctctcgag gatataggac ggaag                           35

<210> SEQ ID NO 141
<211> LENGTH: 35
<212> TYPE: DNA
<213> ORGANISM: Brassica rapa

<400> SEQUENCE: 141
cgtcccccca tcctctcgag gatatgggat ggaag                           35

<210> SEQ ID NO 142
<211> LENGTH: 35
<212> TYPE: DNA
<213> ORGANISM: Brassica rapa

<400> SEQUENCE: 142
cgtcccccca tcctctcgag gatatgggac ggaag                           35

<210> SEQ ID NO 143
<211> LENGTH: 99
<212> TYPE: DNA
<213> ORGANISM: Matricaria chamomilla

<400> SEQUENCE: 143
ttctttgttt tgtgtcgtcg gtcgcaagga taagctctct aaaaacccca atgtgttgtc    60
ttaggatgac gcttcgaccg cgaccccagg tcaggcggg                           99

<210> SEQ ID NO 144
<211> LENGTH: 99
<212> TYPE: DNA
<213> ORGANISM: Matricaria chamomilla

<400> SEQUENCE: 144
ttctttgttt tgtgtcgtcg gtcgcaagga taagctctgt aaaaacccca atgtgttgtc    60
ttaggatgac gcttcgaccg cgaccccagg tcaggcggg                           99

<210> SEQ ID NO 145
<211> LENGTH: 99
<212> TYPE: DNA
<213> ORGANISM: Matricaria chamomilla

<400> SEQUENCE: 145
ttctttgttt tgtgtcgtcg gtcgcaagga taagctctct aaaaacccca atgtgtcgtc    60
ttaggatgac gcttcgaccg cgaccccagg tcaggcggg                           99

<210> SEQ ID NO 146
<211> LENGTH: 96
<212> TYPE: DNA
<213> ORGANISM: Tanacetum parthenium

<400> SEQUENCE: 146
ttctttgttc tgtgttagtc gcaaggaaaa actcttcaaa taccctaatg tgttgtcttc    60
ggatgacgct tcgaccgcga ccccaggtca ggcggg                              96

```
<210> SEQ ID NO 147
<211> LENGTH: 96
<212> TYPE: DNA
<213> ORGANISM: Tanacetum vulgare

<400> SEQUENCE: 147
ttctttgttc tgtgttagtc gcaaggaaaa actcttcaaa taccccaatg tgttatctta    60
ggatgacgct tcgaccgcga ccccaggtca ggcggg                              96

<210> SEQ ID NO 148
<211> LENGTH: 99
<212> TYPE: DNA
<213> ORGANISM: Chamaemelum nobile

<400> SEQUENCE: 148
ttctttgttt tgtgtcgcac gttgctagga agcactctct aaataaccca ttgtgttgtc    60
ttaggatgac gcttcgaccg cgaccccagg tcaggcggg                           99

<210> SEQ ID NO 149
<211> LENGTH: 99
<212> TYPE: DNA
<213> ORGANISM: Chamaemelum nobile

<400> SEQUENCE: 149
ttctttgttt tgtgtcgcac gtcgctagga agcactctct aaataaccca ttgtgttgtc    60
ttaggatgac gcttcgaccg cgaccccagg tcaggcggg                           99

<210> SEQ ID NO 150
<211> LENGTH: 99
<212> TYPE: DNA
<213> ORGANISM: Chamaemelum nobile

<400> SEQUENCE: 150
ttctttgttt tgtgtcgcac gttgctagga agcactctct aaataaccca ttgtgttgtc    60
ttaggatgac gcttcgaccg cgacctcagg tcaggcggg                           99

<210> SEQ ID NO 151
<211> LENGTH: 98
<212> TYPE: DNA
<213> ORGANISM: Chrysanthemum indicum

<400> SEQUENCE: 151
tcttttgttt cgtgctgttg ctcgcaaggt aaactcttta aaaccccaa tgtgccgtct     60 cttgacgacg cttcgaccgc gaccccaggt caggcggg                            98

<210> SEQ ID NO 152
<211> LENGTH: 98
<212> TYPE: DNA
<213> ORGANISM: Chrysanthemum x morifolium

<400> SEQUENCE: 152
tcttttgttt cgtgctgttg ctcgcaaggt aaactcttta aaaccccaa tgtgtcgtct     60 cttgacgacg cttcgaccgc gaccccaggt caggcggg                            98
```